US010662227B2

(12) United States Patent
Barrangou et al.

(10) Patent No.: US 10,662,227 B2
(45) Date of Patent: May 26, 2020

(54) BIFIDOBACTERIA CRISPR SEQUENCES

(75) Inventors: Rodolphe Barrangou, Madison, WI (US); Philippe Horvath, Saint-Gervais-les-3-Clochers (FR); Dennis A. Romero, Oregon, WI (US); Lindsay L. Traeger, Madison, WI (US)

(73) Assignee: DUPONT NUTRITION BIOSCIENCES APS, Copenhagen (DK)

( * ) Notice: Subject to any disclaimer, the term of this patent is extended or adjusted under 35 U.S.C. 154(b) by 196 days.

(21) Appl. No.: 13/127,934

(22) PCT Filed: Nov. 6, 2009

(86) PCT No.: PCT/US2009/063497
§ 371 (c)(1),
(2), (4) Date: Aug. 26, 2011

(87) PCT Pub. No.: WO2010/054154
PCT Pub. Date: May 14, 2010

(65) Prior Publication Data
US 2011/0300538 A1   Dec. 8, 2011

Related U.S. Application Data

(60) Provisional application No. 61/112,673, filed on Nov. 7, 2008.

(51) Int. Cl.
*C12Q 1/68* (2018.01)
*C07K 14/195* (2006.01)

(52) U.S. Cl.
CPC .............. *C07K 14/195* (2013.01); *C12Q 1/68* (2013.01)

(58) Field of Classification Search
None
See application file for complete search history.

(56) References Cited

U.S. PATENT DOCUMENTS 5,474,796 A * 12/1995 Brennan ................. 427/2.13
2006/0199190 A1 * 9/2006 Russell et al. ............ 435/6
2008/0124725 A1    5/2008 Barrangou et al.

FOREIGN PATENT DOCUMENTS

| WO | WO 2007/025097 A2 | 3/2007 |
| WO | 07/136815 | 11/2007 |
| WO | WO 2007/136815 | 11/2007 |

OTHER PUBLICATIONS

Zinedine et al. World Journal of Dairy and Food sciences vol. 2 2007 p. 28.*
Mayo et al. (Current Genomics May 2008 vol. 9 p. 169).*
Horvath et al., "Comparative analysis of CRISPR loci in lactic acid bacteria genome," *International Journal of Food Microbiology*, vol. 131, No. 1, p. 62-70 (May 2008 abstract).
Haft et al., "A guild of 45 CRISPR-associated (cas) protein families and multiple CRISPR/Cas subtypes exist in prokaryotic genomes," *Plos Computational Biology*, vol. 1, No. 6, p. 474-482 (2005).
Barrangou et al., "Comparison of the Complete Genome Sequences of *Bifidobacterium animalis* subsp. *lactis* DSM 10140 and B1-04," Journal of Bacteriology, vol. 191, No. 3, p. 4144-4151 (2009).
Grissa et al, "CRISPRFinder: a web tool to identify clustered regularly interspaced short palindromic repeats," *Nucleic Acids Research*, vol. 35, p. W52-57 (2007).
Grissa et al., "The CRISPRdb database and tools to display CRISPRs and to generate dictionaries of spacers and repeats," *BMC Bioinformatics*, vol. 8, p. 1-10 (2007).
Kim et al., "Genome Sequence of the Probiotic Bacterium *Bifidobacterium animalis* subsp. *lactis* AD011," *Journal of Bacteriology*, vol. 191, No. 2, p. 678-679 (2009).
Altschul S F, et al., Basic local alignment search tool, J. Mol. Biol., 215:403-410, (1990).
Altschul S F, et al., Local alignment statistics, Meth. Enzymol., 266:460-480 (1996).
Barrangou, et al., "CRISPR Provides Acquired Resistance Against Viruses in Prokaryotes," Science 315:1709-12 (Mar. 2007).
Beloglazova N, et al., A novel family of sequence-specific endoribonucleases associated with the clustered regularly interspaced short palindromic repeats, J. Biol. Chem., 2008, 283: 20361-20371; p. 1-21.
Brouns, et al., "Small CRISPR RNAs Guide Antiviral Defense in Prokaryotes," Science 321: 960-964 (2008).
Deveau H, et al., Phage response to CRISPR-encoded resistance in *Streptococcus thermophilus*, J. Bacteriol. 190(4)1 390-1400 (Feb. 2008).
Devereux J, et al., A comprehensive set of sequence analysis programs for the VAX, Nucl. Acid Res., 12:387-395 (1984).
Feng DF and Doolittle RF, Progressive sequence alignment as a prerequisite to correct phylogenetic trees, J. Mol. Evol., 25:351-360 (1987).
Godde JS and Bickerton A, The repetitive DNA elements called CRISPRs and their associated genes: evidence of horizontal transfer among prokaryotes, J. Mol. Evol., 2006, vol. 62, p. 718 (p. 1-10).
Higgins DG and Sharp PM, Fast and sensitive multiple sequence alignments on a microcomputer, CABIOS, 1989, 5:151-153.
Horvath P, et al., Diversity, activity, and evolution of CRISPR loci in *Streptococcus thermophilus*, J. Bacteriol., Feb. 2008, vol. 190, No. 4, p. 1401-1412.
Jansen R, et al., "Identification of a novel family of sequence repeats among prokaryotes," OMICS 6:23-33 (2002).
Jansen R, et al., "Identification of genes that are associated with DNA repeats in prokaryotes," Molecular Microbiology 43:1565-1575 (2002).
Karlin S, et al., Applications and statistics for multiple high-scoring segments in molecular sequences, Proc. Natl. Acad. Sci. USA, 1993, vol. 90, p. 5873-5877.

(Continued)

*Primary Examiner* — Katherine D Salmon

(57) ABSTRACT

The invention relates to CRISPR sequences found in bifidobacteria and their uses.

6 Claims, 12 Drawing Sheets

Specification includes a Sequence Listing.

(56) References Cited

OTHER PUBLICATIONS

Kriegler M, Gene Transfer and Expression: a Laboratory Manual (1990).
Makarova KS, et al., A putative RNA-interference-based immune system in prokaryotes: computational analysis of the predicted enzymatic machinery, functional analogies with eukaryotic RNAi, and hypothetical mechanisms of action, Biol. Direct2006 1: e60; p. 1-26.
Mojica FJM, et al., "Intervening sequences of regularly spaced prokaryotic repeats derive from foreign genetic elements," Journal of Molecular Evolution 60:174-182 (2005).
Needleman SB and Wunsch CD, A general method applicable to the search for similarities in the amino acid sequence of two proteins, J. Mol. Biol., 1970, vol. 48 p. 443-453.
Pearson WR and Lipman JD, Improved tools for biological sequence comparison, Proc. Natl. Acad. Sci. USA, 1988, vol. 85, p. 2444-2448.
Pourcel C, et al., "CRISPR elements in Yersinia pestis acquire new repeats by preferential uptake of bacteriophage DNA and provide additional tools for evolutionary studies," Microbiology 151 :653-663 (2005).
Russell WM & Klaenhammer TR, Efficient system for directed integration into the Lactobacillus acidophilus and Lactobacillus gasseri chromosomes via homologous recombination, Appl. Environ. Microbiol., 2001, v67, p. 4361-4364.
Sambrook, et al., Molecular Cloning: A Laboratory Manual, 2nd edition, 1989, Cold Spring Harbor Laboratory Press.
Smith TF and Waterman MS, Comparison of Biosequences, Advanced Applied Mathematics, 2:482-489 (1981).
Sonnhammer, E.L. Durbin, R. "A dot-matrix program with dynamic threshold control suited for genomic DNA and protein sequence analysis," Gene 167: GC1-10 (1996).
Sorek, et al., "CRISPR—a widespread system that provides acquired resistance against phages in bacteria and archaea," Nature Reviews Microbiology, AOP, published online Dec. 24, 2007; doi:10.1038/nrmicro1793; p. 181-186.
Horvath, et al., Comparative analysis of CRISPR loci in lactic acid bacteria genomes, Intl. J. Food Microbiol., 131(1):62-70, (2008).
Barrangou, et al., Comparison of the complete genome sequences of *Bifidobacterium animalis* subsp *lactis* DSM 10140 and BI-04, J. Bacteriol., 191(13):4144-4151 (2009).
Grissa, et al., CRISPRFinder: a web tool to identify clustered regularly interspersed short palindromic repeats, Nuc Acids Res., 35(31):W52-W57 (2007).
Kim, et al., Genome sequence of the probiotic bacterium *Bifidobacterium animalis* subsp. *lactis* AD011, J. Bacteriol., 191(2): 678-379 (2008).
Briczinski, E. P., et al., "Technical Note: A Rapid Pulsed-Field Gel Electrophoresesis Method for Analysis of Bifidobacteria," *J. Dairy Science* (2006) vol. 89, p. 2424-2427.

* cited by examiner

Bala1 CRISPR locus (SEQ ID NO: 1):

ctatcccgtgcgagggctgcatcatgcagcataaagcggggaatctctcgcatcaatactttgtaagg
atttgttgagtttgtgtagataaatcagtcgtttgtatcacgtcaatttgtctacctctcgcaaaagc
gcttatcagactatgtgtatcagtctgtattatggctactATCTCCGAAGTCTCGGCTTCGGAGCTTC
ATTGAGGGgacgatatggcgctcagcgtggcggagtgggaggcggATCTCCGAAGTCTCGGCTTCGGA
GCTTCATTGAGGGaagaccggcaccgaacgcgacttcaccatgacctcATCTCCGAAGTCTCGGCTTC
GGAGCTTCATTGAGGGcccaccacaacggcaacggcggaggaacacgcgccgaaATCTCCGAAGTCT
CGGCTTCGGAGCTTCATTGAGGGaagcccaactcaatcacacgcatcaaagcgaacaATCTCCGAAGT
CTCGGCTTCGGAGCTTCATTGAGGGgtattcgccgttcgagaggaatgagaggatgctgtcagATCTC
CGAAGTCTCGGCTTCGGAGCTTCATTGAGGGtcgccattggagacgcgacgcaggatactatccgATC
TCCGAAGTCTCGGCTTCGGAGCTTCATTGAGGGacgacaagccgccgccaccgatattcacctgcgaA
TCTCCGAAGTCTCGGCTTCGGAGCTTCATTGAGGGggccgcttcggtgacgggctggtttttccacca
cacgcATCTCCGAAGTCTCGGCTTCGGAGCTTCATTGAGGGaatcccagccgcaaggtctgatgccgc
ctgaaatATCTCCGAAGTCTCGGCTTCGGAGCTTCATTGAGGGcactggtggtgcgaatacgccgaaa
cggtggaatggATCTCCGAAGTCTCGGCTTCGGAGCTTCATTGAGGGattgagattgatacccgtggc
gccgctgatgagacATCTCCGAAGTCTCGGCTTCGGAGCTTCATTGAGGGaatccctcggcccatgat
tcgtcacgtgggatcacATCTCCGAAGTCTCGGCTTCGGAGCTTCATTGAGGGaaacaggtcaatcag
cggcgcagggaggagacgaaATCTCCGAAGTCTCGGCTTCGGAGCTTCATTGAGGGgagtgaacaact
cactgtgcgaaccatcgaaccgttATCTCCGAAGTCTCGGCTTCGGAGCTTCATTGAGGGcggttgag
cagccacgtggtgatactgctcgcgccaATCTCCGAAGTCTCGGCTTCGGAGCTTCATTGAGGGcttg
catccaacgcgcacagcattgcatacgggtatagATCTCCGAAGTCTCGGCTTCGGAGCTTCATTGAG
GGatcatcctcacggaaatagtgagcatcctcgagaacctgATCTCCGAAGTCTCGGCTTCGGAGCTT
CATTGAGGGggccgcgatagtccacgaggcgaacgaaggcgttgcATCTCCGAAGTCTCGGCTTCGGA
GCTTCATTGAGGGgctcaagacactcaccgaccagctcaagaagaccgaATCTCCGAAGTCTCGGCTT
CGGAGCTTCATTGAGGGcgcgatcgtcaccgactgcactgtgttcgcactgtcATCTCCGAAGTCTCG
GCTTCGGAGCTTCATTGAGGGgcgacaccgaacgccgccgccacagtcgggatggcATCTCCGAAGTC
TCGGCTTCGGAGCTTCATTGAGGAagggccagcaacgtcgtggagatccatcaggaggcATCTCCGAA
GTTTTGGCTTCGGAGCTTCATTGAGGAatgtactccgatttttatctaagc

FIG. 1

Bala1 CRISPR Sequences

23 Repeat Sequences (R1-R23)

R1  ATCTCCGAAGTCTCGGCTTCGGAGCTTCATTGAGGG
R2  ATCTCCGAAGTCTCGGCTTCGGAGCTTCATTGAGGG
R3  ATCTCCGAAGTCTCGGCTTCGGAGCTTCATTGAGGG
R4  ATCTCCGAAGTCTCGGCTTCGGAGCTTCATTGAGGG
R5  ATCTCCGAAGTCTCGGCTTCGGAGCTTCATTGAGGG
R6  ATCTCCGAAGTCTCGGCTTCGGAGCTTCATTGAGGG
R7  ATCTCCGAAGTCTCGGCTTCGGAGCTTCATTGAGGG
R8  ATCTCCGAAGTCTCGGCTTCGGAGCTTCATTGAGGG
R9  ATCTCCGAAGTCTCGGCTTCGGAGCTTCATTGAGGG
R10 ATCTCCGAAGTCTCGGCTTCGGAGCTTCATTGAGGG
R11 ATCTCCGAAGTCTCGGCTTCGGAGCTTCATTGAGGG
R12 ATCTCCGAAGTCTCGGCTTCGGAGCTTCATTGAGGG
R13 ATCTCCGAAGTCTCGGCTTCGGAGCTTCATTGAGGG
R14 ATCTCCGAAGTCTCGGCTTCGGAGCTTCATTGAGGG
R15 ATCTCCGAAGTCTCGGCTTCGGAGCTTCATTGAGGG
R16 ATCTCCGAAGTCTCGGCTTCGGAGCTTCATTGAGGG
R17 ATCTCCGAAGTCTCGGCTTCGGAGCTTCATTGAGGG
R18 ATCTCCGAAGTCTCGGCTTCGGAGCTTCATTGAGGG
R19 ATCTCCGAAGTCTCGGCTTCGGAGCTTCATTGAGGG
R20 ATCTCCGAAGTCTCGGCTTCGGAGCTTCATTGAGGG
R21 ATCTCCGAAGTCTCGGCTTCGGAGCTTCATTGAGGG
R22 ATCTCCGAAGTCTCGGCTTCGGAGCTTCATTGAGGA
R23 ATCTCCGAAGTTTTGGCTTCGGAGCTTCATTGAGGA

22 Spacer Sequences (S1-S22)

S1  GACGATATGGCGCTCAGCCGTGGCGGAGTGGGAGGCGG
S2  AAGACCGGCACCGAACGCGACTTCACCATGACCTC
S3  GCCCACCACAACGGCAACGGCGGAGGAACACGCGCCGAA
S4  AAGCCGAACTCAATCACACGCATCAAAGCGAACA
S5  GTATTCGCCGTTCGAGAGGAATGAGAGGATGCTGTCAG
S6  TCGCCATTGGAGACGCGACGCAGGATACTATGGC
S7  ACGACAAGCCGCCGCCACCGATATTCACCTGCGA
S8  GGCCGCTTCGGTGACGGGCTGGTTTTTCCACCACACGC
S9  AATCCCAGCCGCAAGGTCTGATGCCGCCTGAAAT
S10 CACTGGTGGTGCGAATACGCCGAAACGGTGGAATGG
S11 ATTGAGATTGATACCCGTGGCGCCGCTGATGAGAC
S12 AATCCCTCGGCCCATGATTCGTCACGTGGGATCAC
S13 AAACAGGTCAATCAGCGGCGCAGGGAGGAGACGAA
S14 GAGTGAACAACTCACTGTGCGAACCATCGAACCGTT
S15 CGGTTGAGCAGCCACGTGGTGATACTGCTCGCGCCA
S16 CTTGCATCCAACGCGCACAGCATTGCATACGGGTATAG
S17 ATCATCCTCACGGAAATAGTGAGCATCCTCGAGAACCTG
S18 GGCCGCGATAGTCCACGAGGCGAACGAAGGCGTTGC
S19 GCTCAAGACACTCACCGACCAGCTCAAGAAGACCGA
S20 CGCGATCGTCACCGACTGCACTGTGTTCGCACTGTC
S21 GCGACACCGAACGCCGCCGCCACAGTCGGGATGGC
S22 AGGGCCAGCAACGTCGTGGAGATCCATCAGGAGGC

FIG. 2

Cas1 Enzyme (SEQ ID NO: 155):

MKYAENNAMKRGEGLEDTLPISLICDFIFCPRRAWLEIQGEKIESLQMERGFHDHRAVDDANGGRGDTDYRAVNV
NHQGWGLSGRLDAVRLNEDNGVIIREYKATPVRRSMDVTHAMRIQLALQAACMEDMGYRVDGTEIFFTSHHRIVP
VELRKSDYEEAYGSVQEVRKLIECETAPLPFEDDPRCMRCSHAGICLPEERAHNIPEHRIMVKVPDHAVTHLATP
GARAYLKSGRMHVSKNGDEITSVPLDSIQALQIHGNVDVSSGLMRELMWRNIPILWCSGTGRLMGWSVSSYGPNG
ETRVAQHVASHEGRLDLAREFISAKIHNQIVLLRRSDKNNNVLFDMKHIEKSVVNANRIQDILSLEGQAAALYFS
QFHHLISVNKRNEWPWLERMRHPAPDPLNALLDYTYSLLLSDCIRAIVSCGLDAHAGFLHSSKRNKPALALDLME
EFRAPIADSVVQTVVNNGEIKRNGFANVMGSVRLRDETRKTLIGAYERRMATELKHPVYAYRASWRRIVEIQARM
VLGRLEGSLERYRGIRVR

*FIG. 5A*

Cas2 Enzyme (SEQ ID NO: 156):

MNNLMQRYIIAYDIKDDSRRIRVSKLLQSYGNRLQYSVFLMEMREVRLVRMEERLHTLINGAEDSVVIARLDDAK
TSESIVFIGSRNYEDVRVPTVI

*FIG. 5B*

Csb1 - Putative CRISPR-associated Csb Family Protein (SEQ ID NO: 157):

MRKLTVQDLNEAAKIGGSNALTEVTSLAPAAGMGSIVAPAKYTAGNGSTYVYEKRWVNDECVDTVLIDSRTSQAN
RLEDYISRAIEVGHPIFSKMPQVRVRYEMIPGDESSVRYFDDVQLPHRAVDAHIRIAEFSESDKVKYMAARNSSL
EDLSAMLAISPVTVMFGCWDSTRNKNQLRIPASFNGEIYAVLADQTHESPIHRAGARIDPVAAGVHLTKNEAKKI
AERIKGTMNDKKLSKFASSGDGSTIVIGAIPPSTDANALDGIAVRSITRTHVLSFSMLRAMRFGKGPEGDEAIRV
LLAAALINAMVGSNAELHLRENCFLVEADEPKTVLDRRGGKHDDLEMLTLEDADELLAQAYAQAQKKAGIDWHGQ
IITVQGDPAVIESASAADDDDR

*FIG. 5C*

Csb2 - Putative CRISPR-associated Csb Family Protein (SEQ ID NO: 158):

MTFAIRIHFLLASYQGASEYGEKESFPTPMRLYQAMVSAAHTVFSSENSQGMLDKRLNAALEWLESNPPEAIRFP
EIVSQSPTSHNAIAYRRKADKAPKAERARSAVMYRTDEQGDMILEWKNGPDDEECSTIADLCWEIPFLGGAGSPV
RITVEEGFDFPLPDSYMLRPESQSLMEVERARELPCPAPGLHQELMEHYTQANPHPASKIPKDSSTKKDTEVRSE
KRLQCVHRSTYSPQKQAKSAVQLPWTRMIIIPARVESNASAWNPRDDELTAWCVALHRLLVRRWGTDVSPYLTGR
WSTDSMVKRPANNIAIQVLRKDYASLIADQRIAESLPAFILMIPSEMDAGELRKLGTLVRSLANSRIYYSHSKPA
LRLGNPIPGEGVHLWSKPRDGMHRIWSPMPFSVNETQAEKSPAGQSRSWTAECNLAVSIGHVFRNVFRGQIAEKR
GRGKYWDLIDAVTAGDSFVRILAARTVARPDMGDYVHRMREGFMITASTGLIAFENVIKDEILAIGQSRHFGGGL
LIPMDCPESCFTTKGQPKWR

*FIG. 5D*

Cas3 Enzyme (SEQ ID NO: 159):

MEMNATTPNEMLVELYDLFVESLHQGRKPYLWQTRLMREVVNNGQWMKLISAPTGSGKTAVIDVHLFVNALAGLA
ALDDIPLPKELNHLLKSLSLDAVPRRMAVTVNRRGIVDDQYLEASAACARINDVASLDDDTESEILKLIAVGLYA
RQYSELMDRQWTFDQLAFQCQEQGKVVCSAQRLRGGLDDKADMRVWRYKPLECQILCGTPDMIGSRLLFSGYGVS
DAAKPIEAALLAYDAVIVVDEAQLSRQFAYTAQQIPRIEACIRQGEPLPVSPLQVVVTTATPSGENISNLQDEQS
ICGVEEADFKIDLELRRRLRTPRPIQVLSVDDKQIATCMAKESIALQERLGGVVVCFVNTVPRASEVVRRLREAL
GKDAGDNAVRAFVGPMRDYERDQFVQRLDSTEPLYDAIRGDQSAITQTGLKFVVATQTLEAGIDADFSGMISELA
PAASLVQRAGRVNRRGLRPEGPVVICCQNSGKIRGPYMKEDLTAAQMWLESLPVEGLTAWSSVLQPPAPAQLERM
VLQRLEWWDVENLSHTSEDVFAEHRAAGRPYPADVDLWLRDDLADRVTPDVAVVIRTLPQDDYLAQRLLATTPPD
SRELFPVTSYAMLDALQNKLKGRRAFIMRTNSSENGNAVHLLDGQADSDPTLRSGDVLIVDDGARVFSEGIPMLD
PFSKDDKHSKKLQDEITSPGDVFNKCQQSMAVLHANREKQPALYEELSEVLRAETDTDETVEAEYQGIDVSKYPN
LQEALNSCAINNHCFRIAFVDGFIDGDSSDSSVFIVLQSSDAADGDQLQEIGRFNRQGPVLLDGPGSHQESVGSR
AELFAAKLGFDSRLVADIRTAGLHHDDGKKDPRFQTLLRYRMPNVPAEPLAKSMYRSSSWERAKRIELRLDGWRH
EQRSAAECWALDSESLQAHDKELVTRLAGTSHGHGRSMFPMNAQQVIPDAIIQTVSEENGDGSQTIHAIRSAAEE
LFDAGYWQSIMERTNERYGLWGIAFLETLLRAADVTISMEGR

FIG. 5E

Csb3 - Putative CRISPR-associated Csb Family Protein (SEQ ID NO: 160):

MSVLRIPADYDDAFSHMLGFGLASILEDAVEDRICRLWWSGRHTLMVETNDEITEMECAHIVRAHAERWHKSQWL
NARGSYAGKGKTVATLSPRIGTVAGREEWVALERDRRDAIDSLRTTLDERYIGALGEPSYWSLNRTKATPEIQQK
FGASLWEMTPRNRGNEFVTNRLLKLASIITARTAEKVHSGLFGLTNVDELAGTEDSHTPTGLKVPSRTDNARAWC
ALFGFSNCPVYRSVHYETSPTAGFIRHDSGGGPSWHVVLPLTEKSWTLAKYRSVIRSYALDYVGENALHLDQDSL
SDSTVALYAELCRWLRDQGLRYCMLFQRHGTQAKSPEYWLLRGQLIRL

FIG. 5F

CRISPRo9a locus (SEQ ID NO: 25)

atctggtacaccaccgcgttcgcccaccacgggttcggcgtcgcgccgttcgtacgcacggaatcgggaagcaca
ggcctattcattgtggtcatggaagctcctttgcctttgaataacaaccgccaacactatagagatggctccata
gtaggcacccctgaattaattgcctagcgtagtatgcggacgggcgtgtgggaaagtaattcc GCGGTCACATGCACGGGAATCTTCGcaaaatcgaccatatacggcgtttgc ←#1
GCGGCATACTTTACGGAAGTCTCCGcaaggaatgccatgctggagcctcttt ←#2
GCGGTCGGTCATGCGGAAGCATCCGtaaaccatgccgcggcggagtctgcaa ←#3
ATGATGTATCTTACGGAACGCTCCGagaaccatgccagcaaaagacgttttt ←#4
GCGGTCCGTCTCAAGGAAACTTCCGaaaaccatgccacaaagaagcgctatt ←#5
GCGGCGCATCTTACGGAAGCTTCCGaaaaacacggcgcaaacgggtacccct ←#6
GCGGCATATCTCACGGAAGACTCCGcacaatgaaccgcgaagagaacaatct ←#7
GCGGATCAGTTTGCGGAAGACTCCGagaaacaaaccgttttgagaccaccgc ←#8
GCGGTCGGTCATGCGGAAGGTTCCGagtaatggggcgccacagcggcaatct ←#9
GTGGCACGTCGTACGGAAGGTTCCGagaaacacaccaaggaggaatccagaa ←#10
ATGGCATATCTTACGGAAGCTTCCG aaaaacaagccacaaacaaagcgcaaaacagcacttccaagcgcccataggcgctgaatacggtggacaacggcg
aagttatccacaaattccaaatcgggattgcacgacattcgacactctcctaccgtcgaaagcatgaagatagat
tcgcaaatcgagcgactcctcgacgagtcccagaacgcacaccgatgcgcggtgacgaccgac

*FIG. 6*

CRISPRo9b locus (SEQ ID NO: 26)

aatggacgcatgatcgtcgccgaatacgacggcatgacgaaatacggcaatgaccgcaagaccatcgcaaaccac
gtgcaccgggagaaactgcgcgacgaagcgctgcggcaacacggcgtcaccgcgatcatccatttcgattatgag
gatttgctcaatcccaacgaactcattgccaggctcgtcgccgccggtgtgccgtaccgccgctgagcatgcagc
ggatctggtc GCGGCATGGTATGCGGAAGATTCTGagaaccgtgccgcaaacgtagactttt ←#1
GCGGTCGATCATGCGGAAGACTCCGtaaaccgtgcctcaaaaggcatcccgc ←#2
GCGGCACGTCTTACGGGAAGTTCCGagaaaccggccatcggacagtctggaa ←#3
ACTGCACTTCCTAAGGGCGCCTCCAtgaaactggctgcgaaaggagcttat ←#4
GCGGCATGGCTTACGGAAGGTTCCGagagtcgtaccgcaaatggagacttcc ←#5
GCGGTCAGTCTTACGGAAGGTTCCGtgaaagcgactatattcaggtcacttt ←#6
GCGGTCGAATATACGGACGACTCCGaaaaacagaccacgaaacggggtctgt ←#7
GCGGTACAGCTTACGGAAGACTCCG agagctgtgccgaaaatacacgcgggcgccggattatgtgagagtctgcaatatgcgcagctcgcactcgccata
atgcagcgtgagccgcaggtcttcgccgacgctcagatgcacgcgctcgccggtctgcggatcgaacaccgtgag
aggagattccgtcgcgcgaatgtgggcgtctgcggggcatcggcgttcaatccgacgaacag

*FIG. 7*

CRISPRo91 locus (SEQ ID NO: 27)

tgcttcacaatgtccaggaagtctttgtcctgcacatgcagataggtgctgaaaccatctgttcgccgcattttc
aacataggcataccaggacactcctctggagttagacctggttcacagtagctgaaaatccagtatggtccatac
tccaccacagagatgatctggagatgcgattgcatctcggccgccttgcgcaatgcttcctgaatgcccatacca
caccgcccacagcatgaacgcttaactacatggagcgaagtctgcggaacctgtgcgatcttctcttcacaaga
agagtcaaaacacagctcccaccgtcccttttacgcagaagcgatttcgggagattagcgttcgccgccgttcc
gcagccgcgcaccaactgccccgcacatcagaactcttcctcgcaatcattgcagtgatagctcggcgtcgggtg
gaaaatgtcgatgtcgcagccgcccagcaccaccttgccctcagcgagctcacgctgcagttcctcagtgaacgc
aggcataccatgcagaatctgcgccacatgccgcgagccacaccgtgggcacaccacctccgccgattccacatt
ttccgcatccatgtctgcgtaatctcccatattcgccattctcgtcgcctcctcggttccgcaaacagcatagg
cacgcctttcgcattctcagatttcctcaccgctcttcccatcttctcaagtatctatatttccttcctctctg
aattttctcgacataacagagtcaaaatcacacccagtcgtccgctctgcaagaagagcggtaccccgagccagc
GAGGCACGTTTCACGGAAACATCCGcataaccgaccaccaagtcacgcagat  ←#1
GTGGCTCGTCTTTCGGAAGCTTCCGaacgatatgtcgtctgcagacttcccc  ←#2
GCAGCACATTCCACGGAATCTTCCGtaagatatgccattcacagaccattct  ←#3
GCGGCACAGCTCACGGAAACATCCGaagggacgaccgcgcagacccgttcc  ←#4
ACGGCACAACGTACGGAAGCTTCCGtaagatacgtcattctcagaccactct  ←#5
GCGGCACAGCTCACGGACGCTTCCGcaaaaccggccgccaaagcgatatct  ←#6
ACGGCACAGCTCACGGAAACATCCGcaatctatgccgcaaaatgcgcacatc  ←#7
GCGACCTGATTCATGGAAGCATCCG
cgtaatcgaccacagaaccgcggctgtatgccccaacccgtagcgcacctccttatctgcgtaaaaagagtcaaa
taatctttctcaccgactctttttacgcaaacaaagccatacacatctcacgccggagaatgagccaatctcag
tcagtcgacaacgacgccgggtttgccaatctcgtcgagccgataggcaatctccgctttcgatccctcttccgc
cacaattttcaccgtgctgcttttcgcattcacattgctcat

FIG. 8

CRISPRo164 locus (SEQ ID NO: 28)

gcggcacgagatgctcggtacgcacgccggcgcccacctgtgcgcgcacgccgtcatctcccaccgtgtacgcga
gcgcgtcccaatcgattgtcgtcacgaacagctcgccgttcacggtgaaggcgacatgattgcccagaccgtcca
ccgagtacgcaacgatcccggtggcgctctccctcgcacgttcacgacgcgcacgctcggcagcaggcacgtcgt
cgctgccagtgtgttcacgagctcaccgcgttcacgagctccacttcggcatacgcgtcttccccgcagattg
ccagccacagcgaattctcggtgtcctgctcgcccgcggaccgtaggaacagcatgcgcgatccgtcgccgatga
gcttgggagagcgcggcgccccgcatgtgaaccgcaccgttttcgctttgcgcactgggtattcttcgattgcag
attccatcccgcacctctcgtctcatcggatcatctattcgttcccact CTATCCTGCTTCACGGAACCTTCCGtaaaacaggtcgcagactccccttccc ← #1
GCGGCACCTCCCACGGAACCTTCCGcaataccgaccactggcgactctcccg ← #2
GCGGCACAGCTCACGGAAGCTCCCGtaaatctgaccactggaagccccatcg ← #3
GCGGCACAGTTTCCGGAACCATCCGaaaatcagaccacagatgaccttcccc ← #4
GCGGCACATTGCACGGAAACATCCGaaagactgaccacggcgacactgattt ← #5
ACGGCACAGCTTGCGGAAACATCCGcagattcggccacaacggcacccattt ← #6
ACGGCATGGTTCACGGAAACATCCGaaaaccatgccacggcagcgctgattt ← #7
ACGGCACAGCATACGGAACCATCCGtaagatctgccgcctaaggacacatct ← #8
GCAGACCACTCCACGGAACCTTCCGaaaaccagaccatctccaaggctctcc ← #9
GCGGCACCGCTCACGGAAGCATCCG caatacagaccgcaaatacatcggccgaacgattgcggattcctgtgggtccggcgcatagtaggcaatgtggaa
accgcgggaacaaggtggggccgtatgcgtgcagtgaaacggcaaaccgttgcaatccatacgctcccagaggaa
aacgcggcggaccgatgcgcctgaaaattcacacggttgatatataagcgtaggataggtaaggatagaaagggt
aactatgagcgttcttgatcgttttgagaaaagcgtggagggtgcggtcaacggagtgttcgcgaagttcggctc
caaagacctgcagcccgtcgatctctccagcgcgcttgagcgcgaaatcgacgccgaggccatgccggtcggccg
agaccgcaccgtggcgccgaacgagtaccgtttcaaactgagcacacccgatttcgaccgcatcgaaagctgggg
ttccgaggccatggccaatgagctggccgacaatctcacgcagtacgcgaagagccaacactatgcatttgtggg
cccggtcgtcgttatttcgaagaggacctgcaactgaccaaaggcaacttcaagctcacgtccgaatccgtgca
gggcaacgccgtaccggtcaccactgacgagcaggccgaggactgcccgatgctcgaagtcaacaacaaccaata
cctgctcaccaaagacaagacgattctgggtcgcggctcgggctgcgacattgtgattgacgaccccggcatctc
ccgcaaacacctggagatcgacatcacggacaacggtgtgatcgcccgcgacttgggctccacgaacggcacgta
tgtggagggccatcaggttcccgccgcgacgctgctcgatggcaacacgatcacgatcggccgcacccgcatcct
gtactgggcctcctcacaagaccagaggtgagcgtagcgggattttccatgattaccgaacttacctttgcggt
actgaaatacgcgttcctcattctgttatggctg

FIG. 9

CRISPRo228 locus (SEQ ID NO: 29)

gtcaatctatctccgcggtaatcaatgatctatggacgaatgcccggtattttccaaaagaaacggagggcgttc
caaaacgcggcaccgccggtatccaaaagatggacgcgatgcgggcgtgcgtggagatttcggtaagatgagatt
tcagttttgggggacaaaatctccaacacataggggattacagacgccaccgcccgagcgggccaacacggcgcgac
cggcgcggcggcagacaacatcaagcatgggcatgggctaggaggcccacgccgaacacaaataaaaggagtgtg
ccacatggcagcacagatctggtacgaagacgacggcgatctttcggttctcgacggcaagaaggtcgcaatcat
cggttacggctcgcagggccacgcgcatgcgctcaacctgcgtgactccggtgtcgacgtcgtcgtcggcctgcg
tccgaactcgaagtccgtggaattcgccaaggagcagggtctggaagtcaagagcgttccggaagccgctgccga
ggccgacgtcatcatgatcctggcccctgaccagtaccagaagggaatctgggagaacgacatcgagccgaacat
caagccgggcgccgccctggccttcgcacacggcttcaacatccactacggctacatcaagccgagcgaggacca
cccggtcttcatggtcgccccgaagggcccaggccacatcgtccgccgtgagtatgtcgcaggccgtggcgtccc
ggttgtgaccgcagtcgagcaggatccgcgcggcgacggctgggatctcgcactggcttacgcgaaggccctcgg
tgcactgcgcgccggcgccatcaagaccacgttcaaggaagagaccgaaaccgatctgttcggcgagcagaacgt
gctgctcggcggcgtgaacaagctcgtcgaaatgggcttcgaggtactcaccgacgcggctaccagccggagat
cgcctacttcgaggtgtgccacgagctcaagatgatcgtcgacctcatgaacgaaggcggcctgaacaaggatcg
ctggagctgctccgacaccgctcagtacggcgactacgtcagcaccgtcatcgacgagcataccgtgagcgcat
gcagtaccacctgcagcgcattcaggacggctccttcgccaaggagttcatggacgaccaggctgccggcgcccc
gaagttcaagcagctgcaggaggagtactccaacgtccgcatcgaagaggtcggcccgaagctgcgcgccatgtt
ctcctggaacaacgacgccgcgaaggacgccgacgaagccaactccttcaccggcaagatcgcccgcgccaggt
tcagtgagccgcgtgcggtgcgtccgcgcatgaagccgtgagcttcgcatctgtcaaggtggggcatgcataggc
atgccccacctttttgcgttcctgcattgagcggccttctgcactgagcgttctccgcc
GTGGCGCAGTTTGCGGAAGTTTCCGTgaaccgcgccgcaaagcaactcgcgc    ← #1
GCGGTAGTTTTCGCGGATGCTTCCGTttgtttgaccgcaaatgagggcaaaa     ← #2
GTGGTAATTCTTTCGGATGATTCCGTaagctgtgccgcggaggtgtctgcaa     ← #3
ACGGCATGGTTTTCGGATGGTTCCGTgtgtttggccgccgatagacgcagtg     ← #4
ACGGCATATCTTTCGGACGCGTCCGTgtgctatgccggggcgcgggctgtac     ← #5
GTAGCAGATTTCGCGGATGCTTCCGTaagctgtgccgcggagcggtctgcaa     ← #6
ACGGCATATCGTACGGAAGACTCCGTgaaatagaccgcgtatgcccgcatgc     ← #7
ATGGTGGATTACCCGGAAGTTTCCGA gaaacgagccgcagtcatagctgcggctgcccgagacgcgcgccggtgaccgcagtgatctcggcaaccacggca
gccgcggcatacaaccggagcataggcggcaatgaccgggctacttggcg

FIG. 10

CRISPRo245 locus (SEQ ID NO: 30)

aggaatcaggttatagaactggaatacgaagccgatgtcgttgcgccggtacgtcactagatcatggtgattaag
gtcggtgatgtcgcggccgcccacgatcacgcgtcccgaggtggcggtatccatgccgccgagaatattcagcgc
agtcgtcttgccggcgccggactggccaaggatcacgctgagctcgccttcgtcggcggcgaagctcgcaccgtc
gagcgcgcggatggaggaggaaccggcagggtactccttgaccacatcattgaactcgatgtatgccatggccac
ctccatctatacaaattgcacgtcatcgcacagcatacatatagattatgcgaaaaccaatctggagtacagt
ggccgccccgcgtgctgcccgccaat
GCGGTGCAACATACGGAAGCATCCGtgggatgtgccactaaccaccccgcca    ← #1
ACGGCACAGCTTTCGGAAGCATCCGagaaacgtgccacaaaggaatctaaa     ← #2
ATGGCACAGCCTACGGAAGCATCCGcacaacggaccgcaaaccaccccctgca   ← #3
GCGGCACAGCATACGGACGCATCCGagagatgggccagaaaccaccccatca    ← #4
GAGGCACATCTCACGGAAGCATCCGagaaccaaaccgcaggccgtcttcccc    ← #5
GCAGCACAGCGTACGGAAGCATCCGagaaacgtactgccagaaggctccaaa    ← #6
ATGGCATGCCTCTCGGAGGTATCCGagaaacgcgccacggaatggtctgaaa    ← #7
ACAGCATAGCTTTCGGAAGCATCCGcaaaaccgaccgcgaagaagtctgaaa    ← #8
ACGGCATGCCATACGGAAGCATCCG
caaaaccgaccacacagcggccgacggcaacgcctacttgcgcgtggagtcgagcacggtcttcgcgtcgcgctt
cgccgaggcgcgcgaggtgatcgcatacgcggcgaacaacacggcgagccagatcacaccggcgatgagcgcaat
gcggtagct

*FIG. 11*

CRISPRo327 locus (SEQ ID NO: 31)

cgctgttctgcgcgctgcttcccgaacgtcgctagcgtactgcgttatgggaatggcatggcgttcggaggcttc
cgtggaaaccgccaatctgtaatctggaaatggcagtttacgcggaaatgtctgcgcaaactgccgttcaatgcg
cgcgtgctcggcgtgaacaagaaacgcacgggcgacacggtgcgcgatactggaactatgttagtttccgcagat
tcaacaccatccccgaacagtatgccaagaacgcgcccgatgacgcgcgcgtggacggcgtgccctgcgtctcg
ttcccgttctacatcgaccatctcaacccggccgccaagtatttgcactgggaattcagcgacccggattccatt
ccggtatgcggattcgaatggatccactggaccatggcgaatctgccggtcgccgcgctcatgttcgacccgtcc
gacgcgcacgccttgcagattccgccggatttctcgcgccgcgtcaccgcgatgatcccggaggccgtgcagggc
cgcaattcgcaggcgtcgccgctgtacgggcaggatcagcggaatctgcagctcgtcgcacactacaccggcccg
cagccaccggacaaggaccacggttatgtactgcagatctggggcaccacctcgccgatcgccggactcgaacag
ggcttctggctcaacgagatgctgcacggcctcgagcattcgcaggtcgtcgacggcggcggcatcacgctgatc
ggcaagtgctgagctctgcctc GCAGTCCGTTTTTCGGAAGCATCCGtgcgttatgccgcagtgaggtccctct ← #1
GCGGTCTGTTTTGCGGAGTTTTCCGtatgctgtgccgcggtgggtcagtttc ← #2
TTGGTCGTTCTTTCGGAAGCTTCCGtgtaacggtacgcgggagtggcattcc ← #3
GCGGTTCGTTTTTCGGATGCTTCCGtatgactgaccgcagattagctgattg ← #4
GCGGTCCGCCTTACGGATGCTTCCGtatgccaggccatgggggagtcaatct ← #5
GTGGCGTATCTTTCGGAACCTTCCGtgtaatcgaccgcagaagtgctgcctg ← #6
GCGGCATGTCTTGCGGAAGCATCCGcgcgattgaccgcggagggggcgattt ← #7
GCGGCCCAGCTTTCGGAACCTTCCGcgtaacagaccgcggggagggcaatct ← #8
GCGGCATATTTCACGGAAGCTTCCGtaaaacgggccgcagatatgtcgtgca ← #9
GTGGTTCGTTTCACGGAGTCTTCCG tataacaggccgtgaatggggcgatctgcaaaccacataggcgcccgcatattcgcccacatatccacctacgga
ataattggccgcccagcactgccggtgcgcggcaaagcgcggtagaacactaaaggagcgaagagaaaccaattc
gtgaaatcgaggaagcaaaatggcatgcactacaattctggtgggccgcggcgcgagttatgacgggtcgacgat
catcgcgcgcaatgaagacgacgagcccggctcgttcaacaacaagaagctcatcatcgtgcggcctgaagacca
gccgcgcacctacacaagcgtgaacggtcacctgacgatcgagctgcccgacgatccgctgcagtattccgagac
cccgaattcgttcacgagcgacggcgtgtggggcgaggccggtatcaacgaggcgaacgtggcgatgacggccac
cgagacgatcacgtcgaacgcgcgcgcgctcggcgcagacccgctcgtgccgtacacgccggcgatcggcaagcc
cggcgacgcgaattacgtgcccgcagtggccggcggcattggcgaggaggatctcgtcacaatcgtgctgccgta
cattcacaccgctcgcgagggcgtggagcgcttgggctcgctgctcgaggaatatggcacgtacgaaagcaacgg
cattggcttctccgattcgcatgaggtgtggtggatcgagacggtgggcggtcatcattgg

FIG. 12

BIFIDOBACTERIA CRISPR SEQUENCES

CLAIM FOR PRIORITY

This application claims priority under 35 USC 371 to International Application No. PCT/US2009/063497, filed on Nov. 6, 2009, which claims priority to U.S. Provisional Application No. 61/112,673, filed on Nov. 7, 2008, each of which is hereby incorporated by reference in its entirety.

FIELD OF THE INVENTION

The present invention relates to the CRISPR loci of *Bifidobacterium animalis* ssp. *lactis* and uses for these sequences.

BACKGROUND OF THE INVENTION

A CRISPR (Clustered Regularly Interspaced Short Palindromic Repeats) is a distinctive DNA locus (i.e., an array or cluster of DNA sequences) found in the genomes of many bacteria and archaea (for recent review see e.g., Sorek et al., "CRISPR—a widespread system that provides acquired resistance against phages in bacteria and archaea," Nature Reviews Microbiology, AOP, published online 24 Dec. 2007; doi:10.1038/nrmicro1793).

Recently, it has been shown that CRISPR sequences can function as a type of "immune system" that help bacteria defend against phage infections (see e.g., Barrangou et al., "CRISPR Provides Acquired Resistance Against Viruses in Prokaryotes," *Science* 315:1709-12 (March 2007); Deveau et al., *J. Bacteriol.* 190(4):1390-1400 (February 2008); Horvath et al., *J. Bacteriol.* 190(4):1401-12 (February 2008)). At least eight distinct CRISPR loci have been identified in the genomes of lactic acid bacteria (see Horvath et al., "Comparative analysis of CRISPR loci in lactic acid bacteria genomes," Int. J. Food Microbiol., Epub Jul. 15, 2008).

Furthermore, it has been shown that phage resistance in bacteria can be modified by introducing CRISPR sequences into the bacterial genome. For example, removal or addition of particular CRISPR sequences from *S. thermophilus* strains resulted in a modified phage-resistance phenotype (see e.g., Barrangou et al. 2007 supra; Deveau et al., 2008 supra). Intl Publ. No. WO 2007/025097 A2, published Mar. 1, 2007 (which is hereby incorporated by reference herein) discloses inter alia the use of CRISPR loci to modulate the resistance of a bacterial strain against an exogenous nucleic acid (e.g., phage infection).

The structure of a CRISPR locus includes a number of short repeating sequences referred to as "repeats." The repeats occur in clusters and up to 249 repeats have been identified in a single CRISPR locus (see e.g., Sorek et al., 2007, supra) and are usually regularly spaced by unique intervening sequences referred to as "spacers." Typically, CRISPR repeats vary from about 24 to 47 bp in length and are partially palindromic (see Sorek et al., 2007, supra). The repeats are generally arranged in clusters (up to about 20 or more per genome) of repeated units (see Sorek et al., 2007, supra). The spacers are located between two repeats and typically each spacer has a unique sequences are from about 20-72 bp in length (see Sorek et al., 2007, supra). Many spacers are identical to or have high homology with known phage sequences. It has been shown that the insertion of a spacer sequence from a specific phage into a bacterial CRISPR can confer resistance to that phage (see e.g., Barrangou et al., "CRISPR Provides Acquired Resistance Against Viruses in Prokaryotes," *Science* 315:1709-12 (March 2007).

In addition to repeats and spacers, a CRISPR locus also includes a leader sequence and often a set of two to six associated cas genes. The leader sequence typically is an AT-rich sequence of up to 550 bp directly adjoining the 5' end of the first repeat (see Sorek et al., 2007, supra). New repeat-spacer unit is almost always added to the CRISPR locus between the leader and the first repeat (see e.g., Sorek et al., 2007, supra). However, it has been found acquisition of phage resistance also can occur associated with new spacer addition and concomitant spacer deletion away from the CRISP leader sequence (see e.g., Deveau et al., supra).

It is believed that the proteins encoded by the associated cas genes act as a bacterial "immune system" that confer resistance against phages. It has been suggested that the array of repeat-spacer sequence are transcribed into a long RNA and the repeats assume a secondary structure which the cas proteins recognize and process to form small RNAs that function via an RNA-interference-like mechanism (see Sorek et al., 2007, supra). Brouns et al. (2008) have reported that a complex of five cas proteins (CasA, CasB, CasC, CasD, and CasE) in the *E. coli* K12 CRISPR/cas system referred to as "Cascade" cleave a CRISPR RNA precursor in each repeat and retains the cleavage product containing a virus-derived sequence. It is proposed that assisted by the Cas3 helicase, these mature CRISPR RNAs then serve as small guide RNAs that enable Cascade to interfere with virus proliferation. (see e.g., Brouns et al., "Small CRISPR RNAs Guide Antiviral Defense in Prokaryotes," *Science* 321: 960-964 (2008)).

CRISPR sequences are among the most rapidly evolving genomic structures in bacteria. Because of this, and their relative sequence simplicity (i.e., repeat-spacer-repeat) CRISPR sequences provide an ideal genomic system for detecting, typing and tracking specific strains of bacteria. Methods for using CRISPR sequences to detect, type, and track bacterial strains have been disclosed in e.g., U.S. published application 2006/01990190 A1, published Sep. 7, 2006, which is hereby incorporated by reference herein.

A CRISPR locus also provides a very convenient, durable, natural and easy to detect genomic tagging system that does not impact other physiological properties of the tagged prokaryote. Methods for using known phage to induce a CRISPR tag (e.g., addition of a repeat-spacer unit) in a bacterial strain have been disclosed in e.g., U.S. published application 2008/0124725 A1, published May 29, 2008, which is hereby incorporated by reference herein.

SUMMARY OF THE INVENTION

In some embodiments, the invention provides an isolated nucleic acid comprising a sequence of a bifidobacteria CRISPR locus selected from the group consisting of Balal Balal (SEQ ID NO: 1), CRISPRo9a (SEQ ID NO: 25), CRISPRo9b (SEQ ID NO: 26), CRISPRo91 (SEQ ID NO: 27), CRISPRo164 (SEQ ID NO: 28), CRISPRo228 (SEQ ID NO: 29), CRISPRo245 (SEQ ID NO: 30), and CRISPRo327 (SEQ ID NO: 31).

In some embodiments the invention provides, an isolated nucleic acid comprising a Balal Balal repeat sequence selected from SEQ ID NO: 2 and sequence variants thereof. In some embodiments, the sequence variants of SEQ ID NO: 2 can be selected from: substitution of C for T at position 12, substitution of C for T at position 14, and substitution of G for A at position 36.

In some embodiments the invention provides, an isolated nucleic acid comprising a Bala1 Bala1 spacer sequence selected from SEQ ID NOs: 3-24. In some embodiments, the Bala1 Bala1 spacer sequence is selected from SEQ ID NOs: 13, 14, and 15.

In some embodiments the invention provides, an isolated nucleic acid comprising a Bala1 repeat-spacer unit sequence, wherein the repeat sequence comprises SEQ ID NO:2 and a Bala1 spacer sequence selected from SEQ ID NOs: 3-24.

In some embodiments the invention provides an isolated nucleic acid comprising a CRISPRo repeat sequence selected from SEQ ID NOs: 32-42, 53-60, 68-75, 83-92, 102-109, 117-125, and 134-143. In other embodiments, the invention provides an isolated nucleic acid comprising a CRISPRo spacer sequence selected from SEQ ID NOs: 43-52, 61-67, 76-82, 93-101, 110-116, 126-133, and 144-152.

In some embodiments, the invention provides an isolated nucleic acid comprising a CRISPRo repeat-spacer unit sequence, wherein the repeat sequence is selected from SEQ ID NOs: 32-42, 53-60, 68-75, 83-92, 102-109, 117-125, and 134-143, and the spacer sequence is selected from SEQ ID NOs: 43-52, 61-67, 76-82, 93-101, 110-116, 126-133, and 144-152.

In other embodiments, the invention also provides isolated nucleic acids comprising a sequence capable of hybridizing under stringent conditions to any of the above-described isolated Bala1 or CRISPRo nucleic acid sequences.

In some embodiments of the invention, any of the above-described isolated Bala1 or CRISPRo nucleic acid sequences can be incorporated in a vector. Thus, the invention provides a vector comprising a CRISPR locus selected from the group consisting of Bala1 (SEQ ID NO: 1), CRISPRo9a (SEQ ID NO: 25), CRISPRo9b (SEQ ID NO: 26), CRISPRo91 (SEQ ID NO: 27), CRISPRo164 (SEQ ID NO: 28), CRISPRo228 (SEQ ID NO: 29), CRISPRo245 (SEQ ID NO: 30), and CRISPRo327 (SEQ ID NO: 31).

In other embodiments, the invention provides a vector comprising any of the following sequences: a Bala1 repeat sequence selected from SEQ ID NO: 2 and sequence variants thereof; a Bala1 spacer sequence selected from SEQ ID NOs: 3-24; and a Bala1 repeat-spacer unit sequence, wherein the repeat sequence is selected from SEQ ID NO: 2 and variants thereof, and the spacer sequence is selected from SEQ ID NOs: 3-24.

In other embodiments, the invention provides a vector comprising any of the following CRISPRo sequences: a CRISPRo repeat sequence selected from SEQ ID NOs: 32-42, 53-60, 68-75, 83-92, 102-109, 117-125, and 134-143; a CRISPRo spacer sequence selected from SEQ ID NOs: 43-52, 61-67, 76-82, 93-101, 110-116, 126-133, and 144-152; and a CRISPRo repeat-spacer unit sequence, wherein the repeat sequence is selected from SEQ ID NOs: 32-42, 53-60, 68-75, 83-92, 102-109, 117-125, and 134-143, and the spacer sequence is selected from SEQ ID NOs: 43-52, 61-67, 76-82, 93-101, 110-116, 126-133, and 144-152.

In some embodiments, the invention provides a recombinant strain of bacteria with altered phage resistance comprises any of the following Bala1 sequences: a Bala1 repeat sequence selected from SEQ ID NO: 2 and variants thereof; a Bala1 spacer sequence selected from SEQ ID NOs: 3-24; and a Bala1 repeat-spacer unit sequence, wherein the repeat sequence is selected from SEQ ID NO: 2 and variants thereof, and the spacer sequence is selected from SEQ ID NOs: 3-24.

In some embodiments, the invention provides a recombinant strain of bacteria with altered phage resistance comprises any of the following CRISPRo sequences: a CRISPRo repeat sequence selected from SEQ ID NOs: 32-42, 53-60, 68-75, 83-92, 102-109, 117-125, and 134-143; a CRISPRo spacer sequence selected from SEQ ID NOs: 43-52, 61-67, 76-82, 93-101, 110-116, 126-133, and 144-152; and a CRISPRo repeat-spacer unit sequence, wherein the repeat sequence is selected from SEQ ID NOs: 32-42, 53-60, 68-75, 83-92, 102-109, 117-125, and 134-143, and the spacer sequence is selected from SEQ ID NOs: 43-52, 61-67, 76-82, 93-101, 110-116, 126-133, and 144-152.

In some embodiments of the above recombinant strains, the bacteria is a bifidobacteria, and in one embodiment, *B. lactis*.

In some embodiments, the present invention provides methods for preparing a recombinant bacteria strain with altered phage resistance, wherein the methods comprise: (a) transforming bacteria with a nucleic acid comprising a Bala1 spacer sequence selected from SEQ ID NOs: 3-24; (b) contacting the transformed bacteria with a phage; and (c) isolating transformed bacteria that exhibit altered resistance to the phage. In some embodiments, the recombinant bacteria strain has increased phage resistance (e.g., complete resistance), and in other embodiments phage resistance is decreased (e.g., no resistance to phage infection). In some embodiments of the method, the nucleic acid comprises a Bala1 or CRISPRo locus having the sequence selected from: Bala1 (SEQ ID NO: 1), CRISPRo9a (SEQ ID NO: 25), CRISPRo9b (SEQ ID NO: 26), CRISPRo91 (SEQ ID NO: 27), CRISPRo164 (SEQ ID NO: 28), CRISPRo228 (SEQ ID NO: 29), CRISPRo245 (SEQ ID NO: 30), and CRISPRo327 (SEQ ID NO: 31). In other embodiments of the method, the nucleic acid comprises a sequence selected from: a Bala1 repeat sequence (SEQ ID NO: 2 and variants thereof), a Bala1 spacer sequence (SEQ ID NOs: 3-24), and a Bala1 repeat-spacer unit sequence, and a Bala1 repeat-spacer unit sequence, wherein the repeat sequence is selected from SEQ ID NO: 2 and variants thereof, and the spacer sequence is selected from SEQ ID NOs: 3-24. In other embodiments of the method, the nucleic acid comprises a sequence selected from a CRISPRo repeat sequence selected from SEQ ID NOs: 32-42, 53-60, 68-75, 83-92, 102-109, 117-125, and 134-143; a CRISPRo spacer sequence selected from SEQ ID NOs: 43-52, 61-67, 76-82, 93-101, 110-116, 126-133, and 144-152; and a CRISPRo repeat-spacer unit sequence, wherein the repeat sequence is selected from SEQ ID NOs: 32-42, 53-60, 68-75, 83-92, 102-109, 117-125, and 134-143, and the spacer sequence is selected from SEQ ID NOs: 43-52, 61-67, 76-82, 93-101, 110-116, 126-133, and 144-152.

In some embodiments, the present invention provides methods for strain typing, strain detecting, and/or strain tracking, wherein the methods comprise: (a) amplifying genomic DNA from a strain of interest using at least one primer pair, wherein said genomic DNA comprises at least a portion of a sequence of a CRISPR locus; (b) detecting an amplicon generated in step (a), whereby said detected amplicon indicates the particular strain of interest. In some embodiments of the method, detecting an amplicon is carried out using a method selected from: measurement of relative size by gel electrophoresis (e.g., agarose gels) or mass spectrometric analysis; hybridization to probes of known sequence (e.g., immobilized probes on a microarray); and sequencing (e.g., determination of partial or complete sequence of the amplicon. In some embodiments of the method, each primer of the pair is complementary to at least a portion of a sequence of a CRISPR locus. In some embodiments, one primer of the pair is complementary to the first repeat and the other primer of the pair is complementary to the terminal repeat of the CRISPR locus, whereby the amplicon generated comprises all of the CRISPR locus, or at least a portion of every repeat and spacer of the CRISPR locus. In some embodiments, the primer pair comprises SEQ ID NO: 153 and 154.

In some embodiments of the methods for strain typing, strain detecting, and/or strain tracking, each primer of a pair is complementary to a portion of genomic DNA such that the primer pair amplifies at least a portion of a CRISPR locus. Typically, said portions of genomic DNA will comprise sequences directly adjacent to and/or part of the CRISPR locus sequence. In some embodiments of the methods, each primer of a pair is complementary to at least a portion of a repeat sequence of the CRISPR locus, whereby amplification generates an amplicon comprising at least one spacer sequence of the CRISPR locus. In some embodiments of the methods, primer pair sequences are selected wherein each primer is complementary to at least a portion of a different end (i.e., either 5' or 3') of the CRISPR locus repeat sequence, whereby amplification generates a plurality of amplicons having sequences of a plurality of the spacers located between the repeats of the CRISPR locus. In such an embodiment, the plurality of amplicons are detected by sequencing or hybridization to a plurality of probes complimentary to the spacer sequences. In one embodiment of the method, the plurality of amplicons is hybridized to a plurality of immobilized probes (e.g., a microarray), whereby the plurality of spacer sequences detected indicates the specific strain of interest.

In some embodiments of the methods for strain typing, strain detecting, and/or strain tracking, the complementary sequence of the CRISPR locus is a repeat sequence selected from SEQ ID NOs: 2, 32-42, 53-60, 68-75, 83-92, 102-109, 117-125, and 134-143. In other embodiments of the method, each primer of a pair is complementary to at least a portion of a spacer sequence of the CRISPR locus, and in some embodiments, each primer of a pair is complementary to at least a portion of a different spacer sequence, whereby the amplicon generated comprises at least one repeat sequence located between the two spacer sequences. In some embodiments of the method, one primer of the pair is complementary to the spacer sequence adjacent to the first repeat of the CRISPR locus. In some embodiments, one primer of the pair is complementary to the spacer sequence adjacent to the first repeat of the CRISPR locus and the other primer of the pair is complementary to the spacer sequence adjacent to the terminal repeat of the CRISPR locus, whereby the amplicon generated comprises all of, or at least a portion of every spacer in the CRISPR locus.

In some embodiments of the methods for strain typing, strain detecting, and/or strain tracking, the CRISPR locus is selected from the group consisting of: Bala1 (SEQ ID NO: 1), CRISPRo9a (SEQ ID NO: 25), CRISPRo9b (SEQ ID NO: 26), CRISPRo91 (SEQ ID NO: 27), CRISPRo164 (SEQ ID NO: 28), CRISPRo228 (SEQ ID NO: 29), CRISPRo245 (SEQ ID NO: 30), and CRISPRo327 (SEQ ID NO: 31).

In some embodiments, the present invention provides a kit for strain typing, strain detecting, and/or strain tracking, wherein the kit comprises a packaged assembly of: (a) a container of an amplification reagent composition comprising a DNA polymerase, an amplification buffer, and at least one primer pair, wherein each primer of the pair is complementary to a portion of genomic DNA such that the primer pair is capable of amplifying at least a portion of a repeat or spacer sequence of a CRISPR locus; and (b) a container of a detection reagent composition comprising a probe capable of hybridizing under stringent conditions to at least a portion of the CRISPR locus amplified by the primer pair. In some embodiments, each primer pair of the kit is complementary to at least a portion of a repeat or spacer sequence of a CRISPR locus. In some embodiments, each primer of the pair in the kit is complementary to a portion of genomic DNA such that the primer pair is capable of amplifying at least a portion of a CRISPR locus selected from the group consisting of: Bala1 (SEQ ID NO: 1), CRISPRo9a (SEQ ID NO: 25), CRISPRo9b (SEQ ID NO: 26), CRISPRo91 (SEQ ID NO: 27), CRISPRo164 (SEQ ID NO: 28), CRISPRo228 (SEQ ID NO: 29), CRISPRo245 (SEQ ID NO: 30), and CRISPRo327 (SEQ ID NO: 31). In some embodiments, the primer pair comprises SEQ ID NO: 153 and 154.

In some embodiments, the invention provides a method for tagging a bifidobacterial strain comprising: (a) exposing a parent bifidobacterial strain to a phage; (b) selecting a phage insensitive mutant; and (c) comparing a CRISPR locus sequence or a portion thereof from the parent strain and the phage insensitive mutant strain, whereby the presence of an additional repeat-spacer unit in the CRISPR locus sequence of the phage insensitive mutant indicates that the strain is tagged. In some embodiments of the method of strain tagging, the CRISPR locus is selected from the group consisting of: Bala1 (SEQ ID NO: 1), CRISPRo9a (SEQ ID NO: 25), CRISPRo9b (SEQ ID NO: 26), CRISPRo91 (SEQ ID NO: 27), CRISPRo164 (SEQ ID NO: 28), CRISPRo228 (SEQ ID NO: 29), CRISPRo245 (SEQ ID NO: 30), and CRISPRo327 (SEQ ID NO: 31).

In some embodiments, the invention provides an isolated nucleic acid encoding a cas gene of the Bala1 CRISPR locus. In some embodiments, the cas gene of the Bala1 CRISPR locus encodes an amino acid sequence selected from group consisting of SEQ ID NOs: 155, 156, 157, 158, 159, and 160. In one embodiment, the amino acid sequence selected is any one of SEQ ID NOs: 156, 158, and 159.

In some embodiments, the invention provides an isolated nucleic acid comprising a nucleic acid sequence comprising two or more cas genes, wherein the cas genes encode two or more amino acid sequences selected from group consisting of SEQ ID NOs: 155, 156, 157, 158, 159, and 160. In one embodiment, the isolated nucleic acid comprises all six cas genes of the Bala1 CRISPR locus.

BRIEF DESCRIPTION OF THE DRAWINGS

FIG. 1 depicts the nucleotide sequence of the Bala1 locus of the *B. lactis* BI-04 genome (SEQ ID NO: 1). The 23 repeats of 36 bp each, which begin at position 1290, are depicted as bolded letters. The 22 spacers correspond to the lower case letter sequences located between each pair of repeats. The underlined portions correspond to the PCR primer sites of Primer 1 and Primer 2 used to generate an 874 bp amplicon as described in Example 1.

FIG. 2 depicts the 23 repeats (R1-R23) of the Bala1 locus sequence of SEQ ID NO: 1 aligned with each of the 22 spacers (S1-S22).

FIG. 5 depicts amino acid sequences of six Cas proteins located downstream from Bala1 CRISPR repeat-spacer region as shown in schematic of FIG. 3. (A) Cas1 enzyme sequence; (B) Cas2 enzyme sequence; (C) Csb1 protein sequence encoding a putative CRISPR-associated csb gene located directly downstream from cas2; (D) Csb2 protein sequence encoding a putative CRISPR-associated csb gene located directly downstream from csb1; (E) Cas3 enzyme sequence; and (F) Csb3 protein sequence a putative CRISPR-associated csb gene located directly downstream from cas3.

FIG. 6 depicts the sequence of the CRISPRo9a locus. The spacing of the lines of nucleotides have been adjusted so that each of the eleven 25 bp repeats (bolded capitals) are aligned, and sequential numbers added to indicate each of the ten spacers based on its order of occurrence in the sequence.

FIG. 7 depicts the sequence of the CRISPRo9b locus. The spacing of the lines of nucleotides have been adjusted so that each of the eight 25 bp repeats (bolded capitals) is aligned, and each of the seven spacers is indicated with a sequential number based on its order of occurrence in the sequence.

FIG. 8 depicts the sequence of the CRISPRo91 locus. The spacing of the lines of nucleotides have been adjusted so that each of the eight 25 bp repeats (bolded capitals) is aligned and each of the seven spacers is indicated with a sequential number based on its order of occurrence in the sequence.

FIG. 9 depicts the sequence of the CRISPRo164 locus. The spacing of the lines of nucleotides have been adjusted so that each of the ten 25 bp repeats (bolded capitals) aligned, and each of the nine spacers is indicated with a sequential number based on its order of occurrence in the sequence.

FIG. 10 depicts the sequence of the CRISPRo228 locus. The spacing of the lines of nucleotides have been adjusted so that each of the eight 25 bp repeats (bolded capitals) aligned, and each of the seven spacers is indicated with a sequential number based on its order of occurrence in the sequence.

FIG. 11 depicts the sequence of the CRISPRo245 locus. The spacing of the lines of nucleotides have been adjusted so that each of the nine 25 bp repeats (bolded capitals) aligned, and each of the eight spacers is indicated with a sequential number based on its order of occurrence in the sequence.

FIG. 12 depicts the sequence of the CRISPRo327 locus. The spacing of the lines of nucleotides have been adjusted so that each of the ten 25 bp repeats (bolded capitals) aligned, and each of the nine spacers is indicated with a sequential number based on its order of occurrence in the sequence.

DETAILED DESCRIPTION OF THE INVENTION

I. Overview

Figure 3:
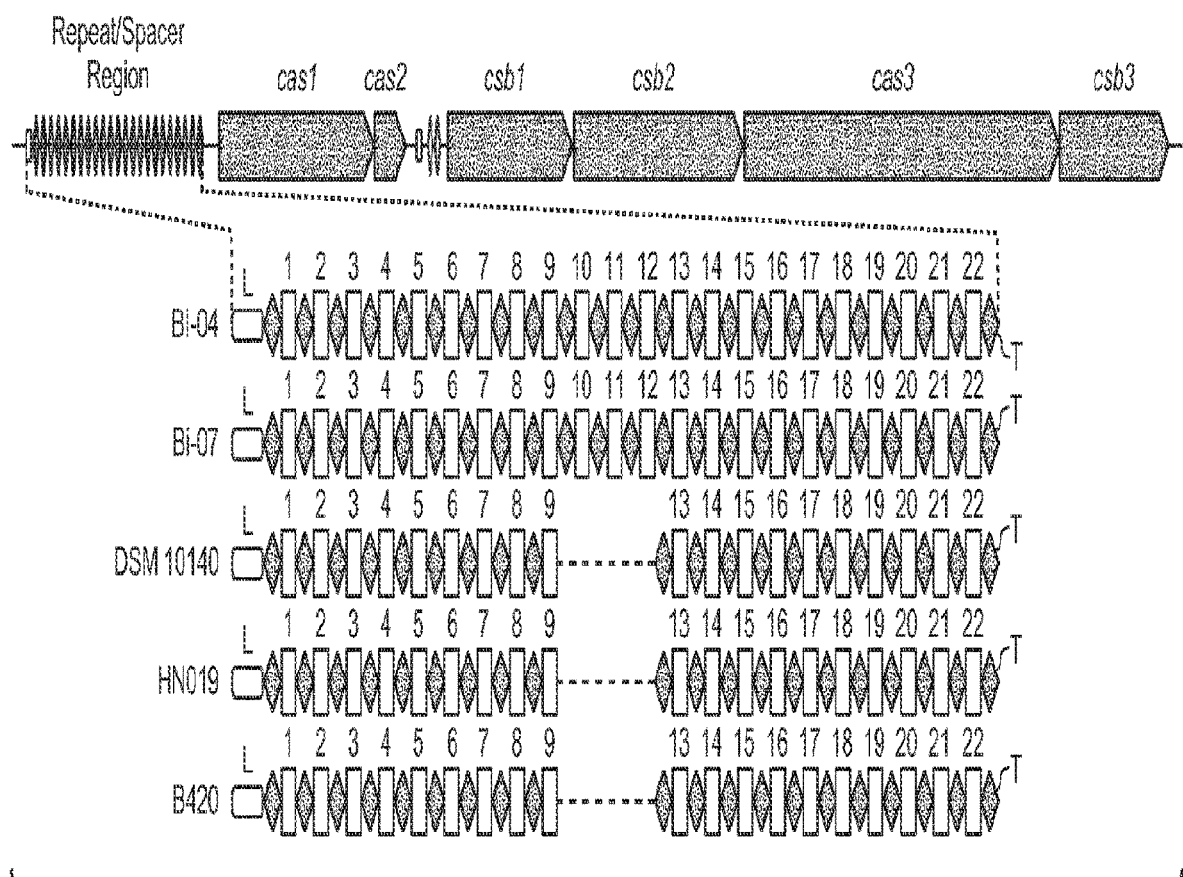
FIG. 3 depicts a schematic comparison of the Bala1 CRISPR locus from the genome of *B. lactis* BI-04 and four other *B. lactis* strains (Bi-07, DSM10140, B420, and HN019). The Bala1 CRISPR locus as it appears in the *B. lactis* genome with six downstream cas genes is shown at the top. The repeat-spacer regions of BI-04 and DSM10140 are shown in expanded view just below with repeats represented as black diamonds and spacers as numbered boxes. The CRISPR locus leader is shown as a white box labeled "L" and the terminal repeat is shown as a black diamond annotated with a "T". The 22 repeat-spacer units of the Bala1 CRISPR locus for the five strains are all depicted. The three repeat-spacer units (which include spacers S10, S11, and S12) that are missing from the DSM10140, B420, and HN019 strains are clearly shown as a gap.

The present invention relates to the CRISPR loci found in *Bifidobacterium animalis* ssp. *lactis* species (referred to herein as "*B. lactis*") and the use of the nucleic acid sequences of these loci in various applications including engineering of phage resistance, strain typing and tracking, and strain tagging.

At least two distinct families of CRISPR loci have been identified in the *B. lactis* BI-04BL-04 genome: "Bala1" and "CRISPRo." The Bala1 locus is accompanied by cas genes, has highly conserved repeats, and is present only once in the BI-04BI-04 genome. In contrast, the CRISPRo locus is not accompanied by cas genes, has degenerate repeats (i.e., repeat sequences having some variability), and is present in at least seven different locations in the BI-04BI-04 genome.

The present invention provides nucleic acid compositions, methods, and kits that utilize nucleic acid sequences of the Bala1 and CRISPRo loci disclosed herein.

II. Definitions

All patents and publications, including all sequences disclosed within such patents and publications, referred to herein are expressly incorporated by reference. Unless defined otherwise herein, all technical and scientific terms used herein have the same meaning as commonly understood by one of ordinary skill in the art to which this invention belongs (See e.g., Singleton et al., DICTIONARY OF MICROBIOLOGY AND MOLECULAR BIOLOGY, 2D ED., John Wiley and Sons, New York [1994]; and Hale and Marham, THE HARPER COLLINS DICTIONARY OF BIOLOGY, Harper Perennial, NY [1991], both of which provide one of skill with a general dictionary of many of the terms used herein). Any methods and materials similar or equivalent to the various embodiments described herein can be used in the practice or testing of the present invention.

It is intended that every maximum (or minimum) numerical limitation disclosed in this specification includes every lower (or higher) numerical limitation, as if such lower (or higher) numerical limitations were expressly written herein. Moreover, every numerical range disclosed in this specification is intended include every narrower numerical range that falls within such broader numerical range, as if such narrower numerical ranges were all expressly written herein.

As used herein, the singular "a", "an" and "the" includes the plural reference unless the context clearly dictates otherwise. Thus, for example, reference to a "host cell" includes a plurality of such host cells.

As used herein the phrase "at least" when used in combination with a list of values or terms is meant to apply to each value or term in the list. For example, the phrase "at least 85%, 90%, 95% and 99% sequence identity" is used to denote at least 85%, at least 90%, at least 95% and/or at least 99% sequence identity.

As used herein the term "comprising" and its cognates are used in their inclusive sense; that is, equivalent to the term "including" and its corresponding cognates.

Unless otherwise indicated, nucleic acids are written left to right in 5' to 3' orientation; amino acid sequences are written left to right in amino to carboxyl orientation, respectively. The headings provided herein are not limitations of the various aspects or embodiments of the invention that can be had by reference to the specification as a whole. Accordingly, the terms defined immediately below are more fully defined by reference to the Specification as a whole.

As used herein when describing proteins and genes that encode them, the term for the gene is generally italicized. The term for the protein is generally not italicized and the first letter is generally capitalized.

As used herein, the terms "isolated" and "purified" are used to refer to a molecule (e.g., an isolated nucleic acid) or other component that is removed from at least one other component with which it is naturally associated.

As used herein, "derived from" encompasses "originated from," "obtained from," or "isolated from."

As used herein, "bacteria" refers to any of the prokaryotic microorganisms that exist as a single cell or in a cluster or aggregate of single cells.

As used herein, "bifidobacteria," refers to any of the species of Gram-positive, anaerobic, branched rod-shaped bacteria that commonly make up gut flora and are referred to as members of genus *Bifidobacterium* including but not limited to: *B. angulatum; B. animalis; B. asteroides; B. bifidum; B. bourn; B. breve; B. catenulatum; B. choerinum; B. coryneforme; B. cuniculi; B. dentium; B. gallicum; B. gallinarum; B indicum; B. longum; B. magnum; B. merycicum; B. minimum; B. pseudocatenulatum; B. pseudolongum; B. psychraerophilum; B. pullorum; B. ruminantium; B. saeculare; B. scardovii; B. simiae; B. subtile; B. thermacidophilum; B. thermophilum; B. urinalis; B. sp.*

As used herein, "*B. lactis*" refers to *Bifidobacterium animalis* ssp. *lactis*.

As used herein, the term "CRISPR locus" refers to the DNA segment which includes all of the CRISPR repeats and spacers, starting with the first nucleotide of the first CRISPR repeat and ending with the last nucleotide of the last (terminal) CRISPR repeat. Typically, each spacer sequence in a CRISPR locus is located between two repeats and consequently, a locus includes one more repeat than spacer sequence.

As used herein, the terms "CRISPR repeat," "repeat sequence," or "repeat" have the conventional meaning as used in the art—i.e., multiple short direct repeating sequences, which show very little or no sequence variation within a given CRISPR locus.

As used herein, "CRISPR spacer," "spacer sequence," or "spacer" refer to the non-repetitive sequences that are located between the repeats of a CRISPR locus.

In some embodiments of the present invention, a "spacer" refers to the nucleic acid segment that is flanked by two repeats. CRISPR spacer sequences often have significant homology to naturally occurring phage or plasmid sequences. Typically, spacers are located between two identical or nearly identical repeat sequences. Thus, spacers often are identified by sequence analysis of the DNA segments located between two CRISPR repeats.

As used herein, the term "cas gene" has its conventional meaning as used in the art where it refers to the one or more genes that are coupled to, associated with, close to, or in the vicinity of a CRISPR locus. Typically, the cas genes associated with a CRISPR locus are encoded by nucleotides located 5' to the CRISPR leader sequence. A comprehensive review of the cas protein family is presented by Haft et al. (Haft et al., Comput. Biol., 1, 6 e60 [2005]; see also, Brouns et al. (2008) supra).

As used herein, a "CRISPR leader," "leader sequence," or "leader" refers to the non-coding sequence located directly upstream of the 5' end of the CRISPR locus. Typically, the CRISPR leader sequence is located between the first nucleotide of the first repeat in the CRISPR locus and the stop codon of the last cas gene.

As used herein, "CRISPR trailer" refers to the non-coding sequence located directly downstream of the 3' end of the CRISPR locus—i.e., right after the last nucleotide of the last CRISPR repeat. This last CRISPR repeat is also referred to as a "terminal repeat."

As used herein, the term "bacteriophage" or "phage" has its conventional meaning as understood in the art—i.e., a virus that selectively infects one or more bacterial species.

As used herein, the terms "tagged bacteria," "tagged bacterium," and "labeled bacteria" are all used interchangeably to refer to a bacteria that has been exposed to a phage and in which one or more CRISPR loci or a portion thereof have been modified in such a way that the bacteria are resistant to the phage. As described in further detail herein, in some embodiments, the tagged bacteria are exposed to more than one phage (e.g., either iteratively, sequentially or simultaneously), such that more than one genomic modifications accumulate within its CRISPR loci in such a way that it becomes insensitive to each of the phages to which it has been exposed.

As used herein, the terms "altered" or "altering" used in the context of a cell's resistance to a nucleic acid may refer to suppressing, reducing, decreasing, inducing, conferring, restoring, elevating, increasing or otherwise affecting the resistance of a cell to a target nucleic acid.

As used herein, the term "resistance to a target nucleic acid" means that resistance conferred against any entity that comprises or produces the target nucleic acid or a transcription product thereof (e.g., a cell, a phage, plasmids, "naked" DNA). The types of entities are not limited to living entities, such as cells and phage, but also include non-living entities e.g., plasmids, or transposable elements. Thus, in some embodiments, the CRISPR sequences of the present invention can provide resistance against any amino-acid containing entity and even free or "naked" nucleic acid sequences that include a target nucleic acid. Resistance can be measured in terms of the survival of the resistant cell or in terms of the prevention of the maintenance and/or survival of the incoming nucleic acid (e.g., prevention of the target nucleic acids replication and/or transcription and/or expression). Resistance is not intended to indicate that foreign DNA is necessarily precluded from entering into the resistant cell (i.e., penetration through the cell membrane). Furthermore, the term "resistance" is not meant to imply that a cell is 100% resistant to a target nucleic acid or a transcription product thereof, but includes cells that are tolerant of the target nucleic acid or a transcription product thereof.

As used herein, "amplification" refers to the production of additional copies of a nucleic acid sequence. Amplification is used in many of the applications of CRISPR sequences (see e.g., Mojica et al., "Intervening sequences of regularly spaced prokaryotic repeats derive from foreign genetic elements," Journal of Molecular Evolution 60:174-182 (2005); and Pourcel et al., "CRISPR elements in *Yersinia pestis* acquire new repeats by preferential uptake of bacteriophage DNA and provide additional tools for evolutionary studies," Microbiology 151:653-663 (2005)) including the embodiments disclosed herein (e.g., strain detecting, typing, tracking, and tagging). In the embodiments of the present invention, amplification typically is carried out using the "polymerase chain reaction" ("PCR") method well-known to those in the art. In addition, other amplification methods, including but not limited to ligase chain reaction ("LCR") and isothermal amplification methods find use in the present invention. Well-known isothermal amplification methods useful in the present invention include, but are not limited to, strand displacement amplification (SDA), Q-beta-replicase, nucleic acid-based sequence amplification (NASBA), and self-sustained sequence replication.

As used herein, "primer" refers to an oligonucleotide, which is naturally occurring (e.g., from a purified restriction digest) or produced synthetically, which is capable of acting as a point of initiation of synthesis (e.g., for an amplification) when placed under conditions in which synthesis of a primer extension product which is complementary to a nucleic acid strand (e.g., an amplicon) is induced (i.e., at a suitable temperature, pH, and in the presence of nucleotides and an inducing agent such as DNA polymerase). PCR primers can be made up of ribonucleotides, deoxyribonucleotides, or synthetic analogs thereof, and typically are at least about 10 nucleotides in length, and most typically at least about 20 nucleotides in length. Methods for designing and conducting PCR are well known in the art, and include, but are not limited to methods using paired primers, nested primers, single specific primers, degenerate primers, gene-specific primers, vector-specific primers, partially mismatched primers, etc.

In various embodiments of the present invention, pairs of primers are used in PCR to amplify all or a portion of a CRISPR locus. In some embodiments, the primer can be single stranded, e.g., for maximum efficiency in amplification, however in other embodiments, the primer can be double-stranded. In some embodiments, the primer can be an oligodeoxyribonucleotide. Generally, the primer must be an oligonucleotide that is sufficiently long to prime the synthesis of extension products in the presence of the inducing agent. The selected length of the primer used in embodiments of the present invention will depend on factors, including temperature, source of primer, and the particular application.

As used herein, "recombinant" used in reference to a cell, nucleic acid, or protein, refers to a cell, nucleic acid, or protein modified by the introduction of a nucleic acid or protein (either native or heterologous) using a vector, or is derived from a cell so modified. Thus, a "recombinant strain of bacteria" refers to a bacterial strain that has been modified by using a vector to introduce of a nucleic acid (e.g., a CRISPR spacer sequence) or protein.

As used herein, the term "vector" refers to any nucleic acid molecule into which another nucleic acid molecule (e.g., a CRISPR repeat-spacer unit sequence) can be inserted and which can be introduced into and replicate within cells. Thus, the term refers to any nucleic acid construct (and, if necessary, any associated delivery system) capable of use for transferring of genetic material between different host cells. Many prokaryotic vectors are commercially available for the production of recombinant strains of bacteria. Selection of appropriate vectors is within the knowledge of those having skill in the art.

As used herein, the term "plasmid" refers to a circular double-stranded (ds) DNA construct that can be used as a vector for introducing DNA into a cell. Plasmids act as extrachromosomal self-replicating genetic element in many bacteria and some eukaryotes. In some embodiments, one or more plasmids can be integrated into the genome of the host cell into which it is introduced.

As used herein, "host," "host cell," or "host strain" refer to a cell that can replicate and/or express a DNA sequence introduced into the cell. In some embodiments of the present invention, the host cells are bifidobacteria.

As used herein, the term "corresponding parent strain" refers to the strain from which a recombinant strain is derived (e.g., the originating and/or wild-type strain). In some embodiments, the corresponding parent strain can be a strain that itself has been engineered or modified.

As used herein, "nucleic acid" refers to a nucleotide or polynucleotide sequence, and fragments or portions thereof, as well as to DNA and RNA of genomic or synthetic origin which may be double-stranded or single-stranded, whether representing the sense or antisense strand.

As used herein, "homologous sequence" refers to a nucleotide or polypeptide sequence having at least about 60%, at least about 70%, at least about 80%, at least about 85%, at least about 88%, at least about 90%, at least about 92%, at least about 94%, at least about 95%, at least about 96%, at least about 97%, at least about 98%, at least about 99%, or even greater sequence identity to a subject nucleotide or amino acid sequence when optimally aligned for comparison. In some embodiments, homologous sequences have between about 80% and 100% sequence identity, in some embodiments between about 90% and 100% sequence identity, and in some embodiments, between about 95% and 100% sequence identity.

Sequence homology can be determined using standard techniques known in the art (see e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]). Useful algorithms for determining sequence homology include: PILEUP and BLAST (Altschul et al., J. Mol. Biol., 215:403-410, [1990]; and Karlin et al., Proc. Natl. Acad. Sci. USA 90:5873-5787 [1993]). PILEUP uses a simplification of the progressive alignment method of Feng and Doolittle (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps.

A particularly useful BLAST program is the WU-BLAST-2 program (See, Altschul et al., Meth. Enzymol., 266:460-480 [1996]). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. An amino acid sequence % identity value is determined by the number of matching identical residues divided by the total number of residues of the "longer" sequence in the aligned region. The longer sequence is the one having the most actual residues in the aligned region (gaps introduced by WU-Blast-2 to maximize the alignment score are ignored).

As used herein, the term "hybridization" refers to the process by which a nucleic acid strand binds with another strand through complementary (e.g., Watson-Crick) base pairing between the strands.

As used herein, "selectively hybridizable" refers to two nucleic acids having sequences that specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° C. below the Tm; "intermediate stringency" at about 10-20° C. below the Tm of the probe; and "low stringency" at about 20-25° C. below the Tm. Functionally, maximum stringency conditions may be used to identify sequences having strict identity or near-strict identity with the hybridization probe; while an intermediate or low stringency hybridization can be used to identify or detect polynucleotide sequence homologs.

Moderate and high stringency hybridization conditions are well known in the art. An example of high stringency conditions includes hybridization at about 42° C. in 50% formamide, 5×SSC, 5×Denhardt's solution, 0.5% SDS and 100 μg/ml denatured carrier DNA followed by washing two times in 2×SSC and 0.5% SDS at room temperature and two additional times in 0.1×SSC and 0.5% SDS at 42° C. An example of moderate stringent conditions include an overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denatured sheared salmon sperm DNA, followed by washing the filters in 1×SSC at about 37-50° C. Those of skill in the art know how to adjust the temperature, ionic strength, etc. as necessary to accommodate factors such as probe length and the like.

As used herein, the term "introducing" (and in past tense, "introduced") used in the context of "introducing a nucleic acid sequence into a cell," refers to any method suitable for transferring the nucleic acid sequence into the cell, including but not limited to transformation, electroporation, nuclear microinjection, transduction, transfection, (e.g., lipofection mediated and DEAE-Dextrin mediated transfection), incubation with calcium phosphate DNA precipitate, high velocity bombardment with DNA-coated microprojectiles, *agrobacterium* mediated transformation, and protoplast fusion.

In various embodiments of the present invention, an exogenous nucleic acid (e.g., a construct or vector) comprising a CRISPR locus sequence or at least a portion thereof are introduced into cells of a bacterial strain. Methods of transforming bacterial cells with nucleic acids resulting in integration into the genome via e.g., homologous recombination are well documented in the art, for example see Sambrook et al (Molecular Cloning: A Laboratory Manual, 2nd edition, 1989, Cold Spring Harbor Laboratory Press) and Ausubel et al., Current Protocols in Molecular Biology (1995), John Wiley & Sons, Inc. Transformed cells may be cultured under conditions well-known for the replication and/or expression of an integrated nucleic acid sequence in a bacterium.

As used herein "an incoming sequence" refers to a DNA sequence that is being introduced into a host cell. The incoming sequence can be a DNA construct, can be a CRISPR sequence, can encode one or more proteins of interest (e.g., a recombinant version of a native protein), and can include flanking sequences such as a promoter and terminator around a protein of interest. For example, the incoming sequence can include Bala1 repeat-spacer unit.

As used herein, a "flanking sequence" or "flanking region" refers to any sequence that is either upstream or downstream of the sequence being discussed (e.g., any spacer has repeats as flanking sequences). In some embodiments, a flanking sequence is present on only a single side (either 3' or 5'), and in other embodiments, it is on each side of the sequence being flanked.

As used herein, the term "integrated" used in reference to a nucleic acid sequence means incorporated into the chromosomal DNA of a host cell. In one embodiment of the present invention, a recombinant CRISPR spacer sequence native to a bacterial species is inserted in a plasmid, used to transform a bacterial cell that does not have that spacer in its endogenous CRISPR loci genome, and the spacer is integrated into the transformed cell's genomic DNA.

III. General Methods and Embodiments of the Inventions

In some aspects, the present invention relies on routine techniques and methods used in the field of genetic engineering and molecular biology. The following resources include descriptions of general methodology useful in accordance with the invention: Sambrook et al., MOLECULAR CLONING: A LABORATORY MANUAL (2nd Ed., 1989); Kreigler, GENE TRANSFER AND EXPRESSION; A LABORATORY MANUAL (1990) and Ausubel et al., Eds. CURRENT PROTOCOLS IN MOLECULAR BIOLOGY (1994). These general references provide definitions and methods known to those in the art. However, it is not intended that the present invention be limited to any particular methods, protocols, and reagents described, as these may vary.

A. The CRISPR Loci of *B. lactis*

1. Identification and Analysis of CRISPR Loci in the *B. lactis* Bl-04 Genome Sequence Various methods for identifying CRISPR loci are known in the art. For example, Jansen et al. describe a computer-based approach in which nucleotide sequences are searched for CRISPR motifs using the PATSCAN program at the server of the Mathematics and Computer Science Division at the Argonne National Laboratory, Argonne, Ill., USA (see e.g., Jansen et al., "Identification of a novel family of sequence repeats among prokaryotes," OMICS 6:23-33 (2002); Jansen et al., "Identification of genes that are associated with DNA repeats in prokaryotes," Molecular Microbiology 43:1565-1575 (2002)). An exemplary algorithm that can be used for identifying CRISPR motifs was p1=a . . . bc . . . dp1 c . . . dp1 c . . . d p1, where a and b were the lower and upper size limit of the repeat and p1 and c and d were the lower and upper size limit of the spacer sequences. The values of a, b, c and d may be varied from about 15 to about 70 bp at increments of about 5 bp. In some embodiments, CRISPR loci are identified using dotplots (e.g., by using the Dotter computer program).

The *B. lactis* Bl-04 genome was sequenced by a combination of Sanger sequencing and pyrosequencing. The resulting three contigs were annotated using the ERGO™ bioinformatics software suite (Integrated Genomics, Chicago, Ill.). The complete draft sequence was segmented into sequence files of 50 kbp. Each individual 50 kbp segment and repeated sequences were visualized using Dotter software (see e.g., Sonnhammer, E. L. Durbin, R. "A dot matrix program with dynamic threshold control suited for genomic DNA and protein sequence analysis," *Gene* 167: GC1-GC10 (1995)). Areas of repeated sequence were analyzed at high resolution in Dotter and fitting the profile of a CRISPR locus were investigated further to determine whether a repeat sequence was present. Potential CRISPR loci were annotated manually by searching a text file of the sequence for non-contiguous repeats. For each candidate CRISPR locus, the candidate repeats were further aligned using CLUSTALW and analyzed using WebLogo. Once a CRISPR locus and its repeats were identified, the spacers were defined as those sequences located between two consecutive repeats.

As described further below, a total of eight CRISPR loci were identified: a CRISPR locus with associated cas genes, called "Bala1"; and a set of seven CRISPR loci that appear to be related referred to as "CRISPRo."

In one embodiment, it is contemplated that the *B. lactis* BI-04 genome CRISPR sequences provided by the present invention can be used to identify CRISPR loci, repeats and spacers in other species of bifidobacteria and other related bacteria. Any suitable method for analyzing sequence similarity known in the art may be used with the CRISPR sequences disclosed herein to analyze bacterial genomes and identify related CRISPR sequences. For example, analysis may be performed using NCBI BLAST with a microbial genomes database and GenBank, as known in the art.

2. The Bala1 Locus

In some embodiments, the present invention provides compositions (e.g., isolated nucleic acids and vectors), methods, and kits comprising nucleotide sequences of the Bala1 locus of the *B. lactis* BI-04 genome.

The Bala1 locus comprises the 2 kb nucleotide sequence (SEQ ID NO: 1) depicted in FIG. 1. As shown in FIGS. 2 and 3, the Bala1 locus comprises a set of 23 repeats of 36 bp and 22 unique spacers, numbered S1-S22, which vary in length from 34 bp to 39 bp.

The Bala1 CRISPR locus was subjected to amplification by PCR in several bifidobacterial species, including the *B. animalis* subsp. *animalis* type strain. This locus was present exclusively in *B. animalis* subsp. *lactis* strains, suggesting it is sub-species specific.

Figure 4:
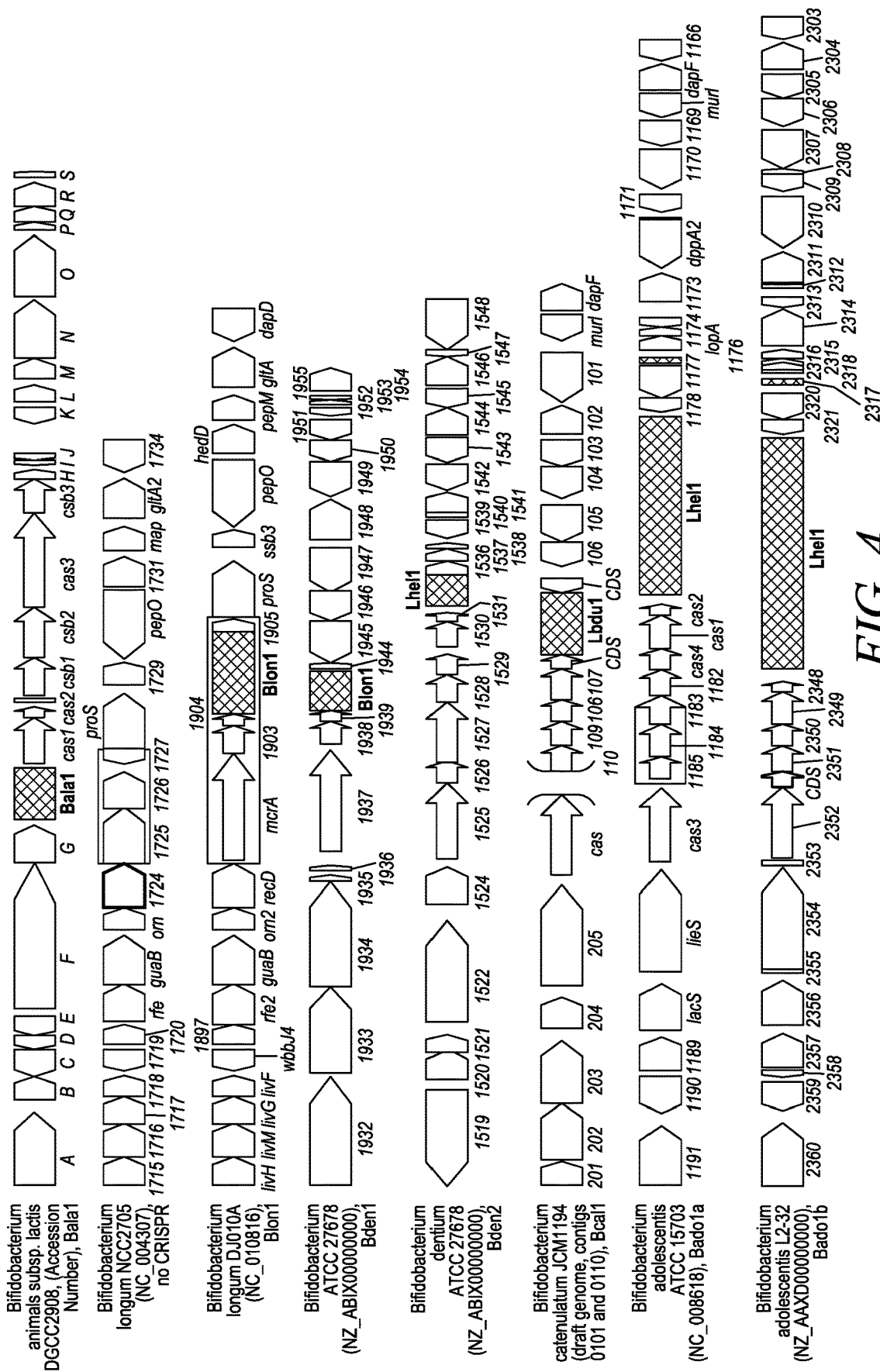
FIG. 4 depicts a schematic comparison of the Bala1 CRISPR locus of *B. lactis* BI-04 with the CRISPR loci found in seven other Bifidobacteria genomes and genome drafts (*B. longum* NCC2705, *B. longum* DJ010A, *B. dentium* ATCC 27678 Bden1, *B. dentium* ATCC 27678 Bden2, *B. catenlatum* JCM1194 Bcat1, *B. adolescentis* ATCC 15703 Bado1a, *B. adolescentis* L2-32 Bado1b). The repeat-spacer regions are shown as black boxes, cas genes are represented by narrow arrows while other genes are represented by box arrows. Rectangles around arrows indicate that these genes are deleted in another strain of the same species.

The Bala1 CRISPR locus is the fourth CRISPR family identified in bifidobacteria. The other bifidobacteria with identified CRISPR loci are Blon1 (*B. longum*), Lhel1 (*B. adolescentis*), and Ldbu1 (*B. catenulatum*) (see Horvath et al., J. Bacteriol., 2008, supra). A comparison of the *B. lactis* BI-04 genome structure surrounding the CRISPR loci has been compared to seven other bifidobacteria genomes is shown in FIG. 4. Bala1 is different from the other CRISPR loci previously identified in bifidobacteria, both in terms of the CRISPR repeat-spacer region (as shown in FIG. 3) and the presence of six downstream cas genes.

As described in the various embodiments disclosed herein, the sequences of the Bala1 locus can be used different applications including but not limited to: strain typing, strain tracking, strain tagging using phage, and engineering of strain resistance against incoming nucleic acids.

Also, in some embodiments of the invention, the sequences of the Bala1 locus can be used for methods of strain typing, detecting, tracking and/or tagging, as described in greater detail below.

3. Bala1 Repeats

There are 23 repeats of 36 bp each in the Bala1 CRISPR locus (SEQ ID NO: 1). These repeat sequences are depicted as bolded capital letters in the depiction of the locus sequence of FIG. 1. The 23 Bala1 repeat sequences (R1-R23) are depicted separately in FIG. 2.

The Bala1 repeat 36 bp consensus nucleotide sequence: ATCTCCGAAGTCTCGGCTTCGGAGCTTCATTGAGGG (SEQ ID NO: 2). This consensus repeat sequence is conserved in the first 21 repeats (R1-R21). The last two repeats (R22 and R23), however, each have SNPs (G for A substitution) at the 3' end, position 36 of SEQ ID NO:2.

Repeat R36 also has T for C substitutions at positions 12 and 14 of SEQ ID NO:2. The results of consensus sequence analysis, using the WebLogo program of the University of California, of the 36 bp repeats showed a high degree of conservation of the sequence (data not shown). A minor variation in the Bala1 repeat at positions 12 (C for T substitution), 14 ((C for T substitution), and 36 (G for A substitution) were observed.

In one embodiment, the present invention provides an isolated nucleic acid composition comprising the Bala1 repeat sequence (SEQ ID NO: 2). In another embodiment the present invention provides an isolated nucleic acid composition comprising a variant of the Bala1 repeat sequence (SEQ ID NO: 2), wherein the variation comprises one or more substitutions selected from the group consisting of: T substitution at position 12, T substitution at position 14, and A substitution at position 36.

4. Bala1 Spacers

The 22 Bala1 spacers identified correspond to the lower case letter sequences located between each pair of repeats.

The Bala1 locus (SEQ ID NO: 1) includes 22 spacers of between 34 and 39 bp. Each of the 22 Bala1 spacers is located between a pair of the Bala1 repeats. As depicted in FIG. 2, the spacer sequence corresponds to the lower case letters located after each set of capital letters corresponding to the 36 bp repeat sequence.

A WebLogo consensus sequence analysis of the 22 Bala1 spacers showed a low degree of conservation indicating the relative distinctiveness of each sequence. Little, if any, consensus among the 22 Bala1 spacer sequences was found. Thus, each Bala1 spacer sequence is highly distinct, unlike the repeats, or some of the CRISPRo locus spacers.

TABLE 1 (below) provides a summary listing the sequences of the 22 Bala1 spacers shown in FIG. 2.

TABLE 1

Summary of Bala1 spacers

| | Bala1 spacers |
|---|---|
| S1 | GACGATATGGCGCTCAGCGTGGCGGAGTGGGAGGCGG (SEQ ID NO: 3) |
| S2 | AAGACCGGCACCGAACGCGACTTCACCATGACCTC (SEQ ID NO: 4) |
| S3 | GCCCACCACAACGGCAACGGCGGAGGAACACGCGCCGAA (SEQ ID NO: 5) |
| S4 | AAGCCGAACTCAATCACACGCATCAAAGCGAACA (SEQ ID NO: 6) |
| S5 | GTATTCGCCGTTCGAGAGGAATGAGAGGATGCTGTCAG (SEQ ID NO: 7) |
| S6 | TCGCCATTGGAGACGCGACGCAGGATACTATGGC (SEQ ID NO: 8) |
| S7 | ACGACAAGCCGCCGCCACCGATATTCACCTGCGA (SEQ ID NO: 9) |
| S8 | GGCCGCTTCGGTGACGGGCTGGTTTTTCCACCACACGC (SEQ ID NO: 10) |
| S9 | AATCCCAGCCGCAAGGTCTGATGCCGCCTGAAAT (SEQ ID NO: 11) |
| S10 | CACTGGTGGTGCGAATACGCCGAAACGGTGGAATGG (SEQ ID NO: 12) |
| S11 | ATTGAGATTGATACCCGTGGCGCCGCTGATGAGAC (SEQ ID NO: 13) |

TABLE 1-continued

Summary of Bala1 spacers

| | Bala1 spacers |
|---|---|
| S12 | AATCCCTCGGCCCATGATTCGTCACGTGGGATCAC (SEQ ID NO: 14) |
| S13 | AAACAGGTCAATCAGCGGCGCAGGGAGGAGACGAA (SEQ ID NO: 15) |
| S14 | GAGTGAACAACTCACTGTGCGAACCATCGAACCGTT (SEQ ID NO: 16) |
| S15 | CGGTTGAGCAGCCACGTGGTGATACTGCTCGCGCCA (SEQ ID NO: 17) |
| S16 | CTTGCATCCAACGCGCACAGCATTGCATACGGGTATAG (SEQ ID NO: 18) |
| S17 | ATCATCCTCACGGAAATAGTGAGCATCCTCGAGAACCTG (SEQ ID NO: 19) |
| S18 | GGCCGCGATAGTCCACGAGGCGAACGAAGGCGTTGC (SEQ ID NO: 20) |
| S19 | GCTCAAGACACTCACCGACCAGCTCAAGAAGACCGA (SEQ ID NO: 21) |
| S20 | CGCGATCGTCACCGACTGCACTGTGTTCGCACTGTC (SEQ ID NO: 22) |
| S21 | GCGACACCGAACGCCGCCGCCACAGTCGGGATGGC (SEQ ID NO: 23) |
| S22 | AGGGCCAGCAACGTCGTGGAGATCCATCAGGAGGC (SEQ ID NO: 24) |

The Bala1 CRISPR locus was identified in both the BI-04 and DSM 10140 genomes. As shown in FIG. 3, polymorphism was observed in terms of the content of the repeat-spacer region. Specifically, although the content was identical both at the leader and the trailer end of the CRISPR locus, three consecutive internal repeat-spacer units were unique to BI-04.

The Bala1 CRISPR locus was sequenced in three additional *B. lactis* strains (Bi-07, B420, and HN019). As shown in FIG. 3, a comparative analysis of the Bala1 CRISPR locus the five different *B. lactis* strains (BI-04, Bi-07, DSM10140, B420, and HN019) reveals that only BI-04 and Bi-07 include 23 repeats and 22 spacers. The genomes of *B. lactis* strains DSM10140, B420, and HN019 do not include spacers S10 (SEQ ID NO:12), S11 (SEQ ID NO:13), and S12 (SEQ ID NO:14). The presence of these three extra repeat-spacer regions also is confirmed by the Dotter plot comparison of the BI-04 and DSM10140 repeat-spacer regions which show a three unit gap between the two.

Similarity to known phage sequences and to metagenomic-derived sequences has been identified for some of the Bala1 CRISPR spacers. S3 has homology with *Streptomyces* phage phi-BT1 AJ550940 and roseovirus NZ_AAMV01000012.1. S17 has homology with frog virus AY548484.1. S19 has homology with human gut metagenome BABA01032251.1. S20 has homology with a phage capsid protein in *Chromohalobacter salexigens* CP000285.1 and with marine metagenome AACY021620797.1. Additionally, S8 has homology with Human gut metagenome BABC01001407.1.

Interestingly, the GC content of the Bala1 CRISPR locus was approximately 49.74%, while that of the genome is 60.19%, suggesting that it may have been acquired laterally from a low-GC microbe, as previously discussed for CRISPR loci (see Godde and Bickerton, 2006; Horvath et al., "Comparative analysis of CRISPR loci in lactic acid bacteria genomes," Int. J. Food Microbiol., Epub Jul. 15, 2008).

In some embodiments, the present invention provides an isolated nucleic acid composition comprising a Bala1 spacer having a sequence selected from the group consisting of SEQ ID NOs: 3-24.

In some embodiments, the present invention provides an isolated nucleic acid comprising a Bala1 repeat sequence linked to a Bala1 spacer sequence in 5' to 3' orientation, wherein the Bala1 repeat sequence is SEQ ID NO: 2 or a variant sequence thereof, and wherein the Bala1 spacer sequence is selected from the group consisting of SEQ ID NOs: 3-24. In one embodiment, the variant of the Bala1 repeat sequence (SEQ ID NO: 2) comprises one or more substitutions selected from the group consisting of: T substitution at position 12, T substitution at position 14, and A substitution at position 36.

5. Bala1 Associated Cas Genes

Typically, four cas genes named cas1 to cas4 are located in the vicinity of a CRISPR locus. The most common arrangement of these genes is cas3-cas4-cas1-cas2. Although not all cast-4 genes are associated with all CRISPR loci, they are all found in multiple subtypes. The Cas3 protein has been predicted to be a HD-nuclease fused to a DEAD-box helicase and has been proposed to assist the Cascade proteins in inhibiting virus proliferation (see e.g., Brouns et al. (2008) supra) Cas4 resembles the RecB family of exonucleases and contains a cysteine-rich motif, suggestive of DNA binding. Cas1 has been predicted to be an integrase (see Brouns et al. (2008) supra; Makarova et al., *Biol. Direct* 1: e60 (2005)). Cas1 is generally highly basic and is the only Cas protein found consistently in all species that contain CRISPR loci. Cas2 is predicted to be an endoribonuclease gene (see Brouns et al. (2008) supra; Beloglazova et al., *J. Biol. Chem.* 283: 20361 (2008)).

As shown by the schematic depiction of the Bala1 locus in FIG. 3, six cas genes are located downstream of the repeat-spacer region, including the universal nuclease cast (COG1518, TIGR00287), the endonuclease cas2 (COG1343, TIGR01573) and the helicase cas3 (COG1203, TIGR02621). Three additional CRISPR-associated Csb family proteins (Csb1, Csb2, and Csb3) were also identified in locations adjacent the cas2 and cas3 genes as shown in FIG. 3. The amino acid sequences encoded by the three Bala1 Cas enzymes and three Csb proteins are shown in FIG. 5 (SEQ ID NOs: 155-160).

These three unassigned cas genes have not been characterized previously, including in other *Bifidobacterium* CRISPR loci (see Horvath et al., 2008 IJFM), but contain cas-type conserved elements (such as cas_GSU0053 and cas_GSU0054). These six cas genes likely are involved in phage resistance conferred by the Bala1 spacer and repeat sequences. The six Bala1 CRISPR locus cas genes have no known homolog in the genome of *B. longum* (see FIG. 4).

In some embodiments, the invention provides an isolated nucleic acid encoding a cas gene of the Bala1 CRISPR locus, wherein the cas gene encodes a Cas protein amino acid sequence as shown in FIG. 5. Thus, the amino acid sequences can be selected from group consisting of SEQ ID NOs: 155, 156, 157, 158, 159, and 160. In one embodiment, the amino acid sequence selected is any one of three Cas proteins of SEQ ID NOs: 156, 158, and 159.

In some embodiments, the invention provides an isolated nucleic acid capable of encoding the full complement of six Bala1 cas genes. Thus, the isolated nucleic acid can comprise the nucleic acid sequences of two or more cas genes, wherein the cas genes encode two or more amino acid sequences selected from group consisting of SEQ ID NOs: 155, 156, 157, 158, 159, and 160. In one embodiment, the isolated nucleic acid comprises all six cas genes of the Bala1 CRISPR locus.

6. The CRISPRo Loci

Homologies were determined between the typical repeats in each identified CRISPR locus in the BI-04 genome. The homology between the repeats of seven CRISPR loci was high enough to define them as the "CRISPRo" loci subset. Based on their degeneracy, it appears that the seven CRISPRo loci are derived from a single CRISPR ancestor.

In some embodiments, the present invention provides compositions (e.g., isolated nucleic acids and vectors), methods, and kits comprising nucleotide sequences of the seven CRISPRo loci of the *B. lactis* BI-04 genome.

The CRISPRo loci do not comprise cas genes. In some embodiments of the invention, each of the seven CRISPRo loci can be used for methods of strain typing, detecting, tracking and/or tagging, as described in greater detail below.

The seven CRISPRo loci are named according to their location on the BI-04 genome. Specifically, the number that appears at the end of the work indicates the approximate location in terms of kilobases (kb). Hence, the seven CRISPRo loci are: CRISPRo9a, CRISPRo9b, CRISPRo91, CRISPRo164, CRISPRo228, CRISPRo245, and CRISPRo327.

The nucleotide sequences of the seven CRISPRo loci with their repeat and spacer subsequences aligned are depicted in FIGS. 6-12. The CRISPRo loci sequence identifiers are as follows: CRISPRo9a (SEQ ID NO: 25), CRISPRo9b (SEQ ID NO: 26), CRISPRo91 (SEQ ID NO: 27), CRISPRo164 (SEQ ID NO: 28), CRISPRo228 (SEQ ID NO: 29), CRISPRo245 (SEQ ID NO: 30), and CRISPRo327 (SEQ ID NO: 31).

The seven CRISPRo loci each have from 8 to 11 repeats and from 7 to 10 corresponding spacer sequences. The nucleotide sequences of the repeats and spacers found in the seven CRISPRo loci are listed in Table 2 below.

TABLE 2

Summary of 7 CRISPRo loci repeats and spacers

| | CRISPRo9a repeats | CRISPRo9a spacers |
|---|---|---|
| #1 | GCGGTCACATGCACGGGAATCTTCG (SEQ ID NO: 32) | caaaatcgaccatatacggcgtttgc (SEQ ID NO: 43) |
| #2 | GCGGCATACTTTACGGAAGTCTCCG (SEQ ID NO: 33) | caaggaatgccatgctggagcctcttt (SEQ ID NO: 44) |
| #3 | GCGGTCGGTCATGCGGAAGCATCCG (SEQ ID NO: 34) | taaaccatgccgcggcggagtctgcaa (SEQ ID NO: 45) |
| #4 | ATGATGTATCTTACGGAACGCTCCG (SEQ ID NO: 35) | agaaccatgccagcaaaagacgttttt (SEQ ID NO: 46) |
| #5 | GCGGTCCGTCTCAAGGAAACTTCCG (SEQ ID NO: 36) | aaaaccatgccacaaagaagcgctatt (SEQ ID NO: 47) |
| #6 | GCGGCGCATCTTACGGAAGCTTCCG (SEQ ID NO: 37) | aaaaacacggcgcaaacgggtacccct (SEQ ID NO: 48) |
| #7 | GCGGCATATCTCACGGAAGACTCCG (SEQ ID NO: 38) | cacaatgaaccgcgaagagaacaatct (SEQ ID NO: 49) |
| #8 | GCGGATCAGTTTGCGGAAGACTCCG (SEQ ID NO: 39) | agaaacaaaccgttttgagaccaccgc (SEQ ID NO: 50) |
| #9 | GCGGTCGGTCATGCGGAAGGTTCCG (SEQ ID NO: 40) | agtaatgggcgccacagcggcaatct (SEQ ID NO: 51) |
| #10 | GTGGCACGTCGTACGGAAGGTTCCG (SEQ ID NO: 41) | agaaacacaccaaggaggaatccagaa (SEQ ID NO: 52) |
| #11 | ATGGCATATCTTACGGAAGCTTCCG (SEQ ID NO: 42) | |
| | CRISPRo9b repeats | CRISPRo9b spacers |
| #1 | GCGGCATGGTATGCGGAAGATTCTG (SEQ ID NO: 53) | agaaccgtgccgcaaacgtagactttt (SEQ ID NO: 61) |
| #2 | GCGGTCGATCATGCGGAAGACTCCG (SEQ ID NO: 54) | taaaccgtgcctcaaaaggcatcccgc (SEQ ID NO: 62) |
| #3 | GCGGCACGTCTTACGGGAAGTTCCG (SEQ ID NO: 55) | agaaaccggccatcggacagtctggaa (SEQ ID NO: 63) |
| #4 | ACTGCACTTCCTAAGGGCGCCTCCA (SEQ ID NO: 56) | tgaaactggctgcgaaaggagcttat (SEQ ID NO: 64) |
| #5 | GCGGCATGGCTTACGGAAGGTTCCG (SEQ ID NO: 57) | agagtcgtaccgcaaatggagacttcc (SEQ ID NO: 65) |

TABLE 2-continued

Summary of 7 CRISPRo loci repeats and spacers

| | | |
|---|---|---|
| #6 | GCGGTCAGTCTTACGGAAGGTTCCG (SEQ ID NO: 58) | tgaaagcgactatattcaggtcacttt (SEQ ID NO: 66) |
| #7 | GCGGTCGAATATACGGACGACTCCG (SEQ ID NO: 59) | aaaaacagaccacgaaacggggtctgt (SEQ ID NO: 67) |
| #8 | GCGGTACAGCTTACGGAAGACTCCG (SEQ ID NO: 60) | |

| | CRISPRo91 repeats | CRISPRo91 spacers |
|---|---|---|
| #1 | GAGGCACGTTTCACGGAAACATCCG (SEQ ID NO: 68) | cataaccgaccaccaagtcacgcagat (SEQ ID NO: 76) |
| #2 | GTGGCTCGTCTTTCGGAAGCTTCCG (SEQ ID NO: 69) | aacgatatgtcgtctgcagacttcccc (SEQ ID NO: 77) |
| #3 | GCAGCACATTCCACGGAATCTTCCG (SEQ ID NO: 70) | taagatatgccattcacagaccattct (SEQ ID NO: 78) |
| #4 | GCGGCACAGCTCACGGAAACATCCG (SEQ ID NO: 71) | aagggacgaccgcgcagacccccgttcc (SEQ ID NO: 79) |
| #5 | ACGGCACAACGTACGGAAGCTTCCG (SEQ ID NO: 72) | taagatacgtcattctcagaccactct (SEQ ID NO: 80) |
| #6 | GCGGCACAGCTCACGGACGCTTCCG (SEQ ID NO: 73) | caaaaccggccgccaaagcgatatct (SEQ ID NO: 81) |
| #7 | ACGGCACAGCTCACGGAAACATCCG (SEQ ID NO: 74) | caatctatgccgcaaaatgcgcacatc (SEQ ID NO: 82) |
| #8 | GCGACCTGATTCATGGAAGCATCCG (SEQ ID NO: 75) | |

| | CRISPRo164 repeats | CRISPRo164 spacers |
|---|---|---|
| #1 | CTATCCTGCTTCACGGAACCTTCCG (SEQ ID NO: 83) | taaaacaggtcgcagactccccttccc (SEQ ID NO: 93) |
| #2 | GCGGCACCTCCCACGGAACCTTCCG (SEQ ID NO: 84) | caataccgaccactggcgactctcccg (SEQ ID NO: 94) |
| #3 | GCGGCACAGCTCACGGAAGCTCCCG (SEQ ID NO: 85) | taaatctgaccactggaagccccatcg (SEQ ID NO: 95) |
| #4 | GCGGCACAGTTTCCGGAACCATCCG (SEQ ID NO: 86) | aaaatcagaccacagatgaccttcccc (SEQ ID NO: 96) |
| #5 | GCGGCACATTGCACGGAAACATCCG (SEQ ID NO: 87) | aaagactgaccacggcgacactgattt (SEQ ID NO: 97) |
| #6 | ACGGCACAGCTTGCGGAAACATCCG (SEQ ID NO: 88) | cagattcggccacaacggcacccattt (SEQ ID NO: 98) |
| #7 | ACGGCATGGTTCACGGAAACATCCG (SEQ ID NO: 89) | aaaaccatgccacggcagcgctgattt (SEQ ID NO: 99) |
| #8 | ACGGCACAGCATACGGAACCATCCG (SEQ ID NO: 90:) | taagatctgccgcctaaggacacatct (SEQ ID NO: 100) |
| #9 | GCAGACCACTCCACGGAACCTTCCG (SEQ ID NO: 91) | aaaaccagaccatctccaaggctctcc (SEQ ID NO: 101) |
| #10 | GCGGCACCGCTCACGGAAGCATCCG (SEQ ID NO: 92) | |

| | CRISPRo228 repeats | CRISPRo228 spacers |
|---|---|---|
| #1 | GTGGCGCAGTTTGCGGAAGTTTCCGT (SEQ ID NO: 102) | gaaccgcgccgcaaagcaactcgcgc (SEQ ID NO: 110) |
| #2 | GCGGTAGTTTTCGCGGATGCTTCCGT (SEQ ID NO: 103) | ttgtttgaccgcaaatgagggcaaaa (SEQ ID NO: 111) |
| #3 | GTGGTAATTCTTTCGGATGATTCCGT (SEQ ID NO: 104) | aagctgtgccgcggaggtgtctgcaa (SEQ ID NO: 112) |

TABLE 2-continued

Summary of 7 CRISPRo loci repeats and spacers

4  ACGGCATGGTTTTCGGATGGTTCCGT  gtgtttggccgccgatagacgcagtg
    (SEQ ID NO: 105)            (SEQ ID NO: 113)

5  ACGGCATATCTTTCGGACGCGTCCGT  gtgctatgccggggcgcgggctgtac
    (SEQ ID NO: 106)            (SEQ ID NO: 114)

6  GTAGCAGATTTCGCGGATGCTTCCGT  aagctgtgccgcggagcggtctgcaa
    (SEQ ID NO: 107)            (SEQ ID NO: 115)

7  ACGGCATATCGTACGGAAGACTCCGT  gaaatagaccgcgtatgcccgcatgc
    (SEQ ID NO: 108)            (SEQ ID NO: 116)

8  ATGGTGGATTACCCGGAAGTTTCCGA
    (SEQ ID NO: 109)

| CRISPRo245 repeats | CRISPRo245 spacers |

1  GCGGTGCAACATACGGAAGCATCCG   tgggatgtgccactaaccaccccgcca
    (SEQ ID NO: 117)            (SEQ ID NO: 126)

2  ACGGCACAGCTTTCGGAAGCATCCG   agaaacgtgccacaaaggaatctaaa
    (SEQ ID NO: 118)            (SEQ ID NO: 127)

3  ATGGCACAGCCTACGGAAGCATCCG   cacaacggaccgcaaaccaccccctgca
    (SEQ ID NO: 119)            (SEQ ID NO: 128)

4  GCGGCACAGCATACGGACGCATCCG   agagatgggccagaaaccaccccatca
    (SEQ ID NO: 120)            (SEQ ID NO: 129)

5  GAGGCACATCTCACGGAAGCATCCG   agaaccaaaccgcaggccgtcttcccc
    (SEQ ID NO: 121)            (SEQ ID NO: 130)

6  GCAGCACAGCGTACGGAAGCATCCG   agaaacgtactgccagaaggctccaaa
    (SEQ ID NO: 122)            (SEQ ID NO: 131)

7  ATGGCATGCCTCTCGGAGGTATCCG   agaaacgcgccacggaatggtctgaaa
    (SEQ ID NO: 123)            (SEQ ID NO: 132)

8  ACAGCATAGCTTTCGGAAGCATCCG   caaaaccgaccgcgaagaagtctgaaa
    (SEQ ID NO: 124)            (SEQ ID NO: 133)

9  ACGGCATGCCATACGGAAGCATCCG
    (SEQ ID NO: 125)

| CRISPRo327 repeats | CRISPRo327 spacers |

1  GCAGTCCGTTTTCGGAAGCATCCG    tgcgttatgccgcagtgaggtccctct
    (SEQ ID NO: 134)            (SEQ ID NO: 144)

2  GCGGTCTGTTTTGCGGAGTTTTCCG   tatgctgtgccgcggtgggtcagtttc
    (SEQ ID NO: 135)            (SEQ ID NO: 145)

3  TTGGTCGTTCTTTCGGAAGCTTCCG   tgtaacggtacgcgggagtggcattcc
    (SEQ ID NO: 136)            (SEQ ID NO: 146)

4  GCGGTTCGTTTTTCGGATGCTTCCG   tatgactgaccgcagattagctgattg
    (SEQ ID NO: 137)            (SEQ ID NO: 147)

5  GCGGTCCGCCTTACGGATGCTTCCG   tatgccaggccatgggggagtcaatct
    (SEQ ID NO: 138)            (SEQ ID NO: 148)

6  GTGGCGTATCTTTCGGAACCTTCCG   tgtaatcgaccgcagaagtgctgcctg
    (SEQ ID NO: 139)            (SEQ ID NO: 149)

7  GCGGCATGTCTTGCGGAAGCATCCG   cgcgattgaccgcggaggggcgattt
    (SEQ ID NO: 140)            (SEQ ID NO: 150)

8  GCGGCCCAGCTTTCGGAACCTTCCG   cgtaacagaccgcggggagggcaatct
    (SEQ ID NO: 141)            (SEQ ID NO: 151)

9  GCGGCATATTTCACGGAAGCTTCCG   taaaacgggccgcagatatgtcgtgca
    (SEQ ID NO: 142)            (SEQ ID NO: 152)

10 GTGGTTCGTTTCACGGAGTCTTCCG
    (SEQ ID NO: 143)

Generally, the CRISPRo repeats are all 25 bp (except CRISPRo which is 26 bp) and within each of the seven CRISPRo loci, the repeats exhibit a high degree of sequence consensus among the repeats is high but not as high as for the Bala1 repeats. Generally, the CRISPRo spacers are all 26 or 27 bp. WebLogo analysis showed (as for the Bala1 spacers) there is little consensus among the CRISPRo spacer sequences found in each of the seven loci.

A sequence consensus analysis of the CRISPRo repeats and spacers where the comparisons were carried out across all seven of the CRISPRo loci (data not shown). The CRISPRo repeats were found to have a high degree of homology in at least 10 of the 25 nucleotides (e.g., positions 3-4, 14-17, and 22-25) across all 7 loci. In contrast, the CRISPRo spacers show a high degree of homology in only about 2 of 27 nucleotides (e.g., positions 10-11) across all 7 loci.

A sequence consensus analysis of the combined CRISPRo repeat-spacer sequence across all 7 loci but not including the last repeat in each locus was performed with WebLogo (data not shown). Interestingly, a sequence motif including the first 31 bp, which includes the repeat sequences and a portion of the spacer sequence, is palindromic. It is believed that the palindromic character of this combined sequence may be critical to the functionality of the CRISPRo loci.

Thus, in another embodiment, the present invention provides an isolated nucleic acid comprising a CRISPRo repeat sequence linked to a CRISPRo spacer sequence in 5' to 3' orientation, wherein the CRISPRo repeat sequence is selected from group consisting of SEQ ID NOs: 32-42, 53-60, 68-75, 83-92, 102-109, 117-125, and 134-143, and wherein the CRISPRo spacer sequence is selected from the group consisting of SEQ ID NOs: 43-52, 61-67, 76-82, 93-101, 110-116, 126-133, and 144-152.

B. Engineering Altered Resistance to Nucleic Acids Using Recombinant *B. lactis* CRISPR Sequences CRISPR loci have been shown to provide resistance in prokaryotes against incoming nucleic acids. For example, it has been shown that specific spacer sequences in CRISPR locus confer or modify resistance in *S. thermophilus* strains against specific phage (see e.g., Barrangou et al., 2007 supra). The general methods disclosed to engineer altered resistance in *S. thermophilus* strains to phage can be used to engineer altered resistance in other bacterial strains having CRISPR loci.

Methods for altering bacterial resistance to exogenous nucleic acids (e.g., phage) by adding, deleting, and/or modifying sequences in endogenous CRISPR loci found in the bacteria also are disclosed in e.g., Russell & Klaenhammer, Appl. Environ. Microbiol. 67, 4361 (2001); and PCT publ. no. WO2007/025097 A2, published Mar. 1, 2007, which is hereby incorporated by reference herein. These methods can be used in the embodiments of the present invention.

Generally, the minimal genomic structure required to confer CRISPR associated resistance against a target nucleic acid (or expression product thereof) is at least one cas gene (or one Cas protein) and at least two CRISPR repeats flanking a spacer. Thus, in some embodiments, the present invention provides a method for altering (e.g., conferring or increasing) resistance of a cell against a target nucleic acid or a transcription product thereof, wherein the method comprises: (a) preparing a nucleic acid comprising at least one cas gene and at least two CRISPR repeats together with the CRISPR spacer, wherein the CRISPR spacer sequence is homologous (e.g., typically 100% identical) to a target nucleic acid sequence (e.g., a conserved sequence essential to the function or survival of the organism); and (b) transforming a cell with said nucleic acid, whereby the transformed cell is rendered resistant to said target nucleic acid or transcription product thereof. In some embodiments, the method further comprises (c) contacting the transformed bacteria with the target nucleic acid; and (d) isolating transformed bacteria that exhibit altered resistance to the target nucleic acid.

Methods of transforming bacterial cells with nucleic acids comprising CRISPR sequences such that transformation results in integration into the genome via e.g., homologous recombination are well documented in the art, for example see Sambrook et al (Molecular Cloning: A Laboratory Manual, 2nd edition, 1989, Cold Spring Harbor Laboratory Press) and Ausubel et al., Current Protocols in Molecular Biology (1995), John Wiley & Sons, Inc. Transformed cells may be cultured under conditions well-known for the replication and/or expression of an integrated nucleic acid sequence in a bacterium.

In some embodiments of the method, a CRISPR spacer previously has been identified that is associated with an organism's resistance to the target nucleic acid or a transcription product thereof. In such a situation, the method may be carried out using the known spacer sequence. In some embodiments of the present invention, the spacer sequence is selected from the group of *B. lactis* Bala1 spacers consisting of SEQ ID NOs: 3-24.

In prokaryotes where the genome already comprises a CRISPR locus and associated cas genes, CRISPR associated resistance can be altered by modifying the existing CRISPR sequences. In embodiments where the sequence of a resistance-associated CRISPR spacer is already known, the sequence of an existing CRISPR spacer in an organism can be modified so that it is homologous or identical to the resistance-associated CRISPR spacer. Alternatively, a repeat-spacer unit having the resistance-associated CRISPR spacer sequence can be inserted in the existing CRISPR locus, thereby altering the resistance of the organism. In other embodiments, where it is desired to decrease resistance, a known resistance-associated CRISPR spacer can be modified or deleted (as a repeat-spacer unit) from the existing CRISPR locus, thereby decreasing or completely removing the organism's resistance to the target nucleic acid.

The *B. lactis* Bala1 locus includes the typical CRISPR elements required for phage resistance, including associated cas genes, conserved repeats, and spacer sequences that exhibit homology to known phage sequences. For example, nucleotides 18-36 of Bala1 spacer S18 (SEQ ID NO: 20) have 100% identity with part of a gene sequence (ABE58753.1; GI: 91796614) found in the genome of phage, *C. salexigens*.

A homology analysis carried out on the CRISPRo spacer sequences identified at least one spacer in each of the seven CRISPRo loci that had significant homology to a known phage sequence.

TABLE 3

Phage sequence homology of CRISPRo spacers

| CRISPRo locus | spacer | spacer sequence (phage homologous sequence bolded) |
|---|---|---|
| 9a | #3 | taaaccatgccgcggcggagtctgcaa (SEQ ID NO: 45) |
| 9a | #4 | agaaccatgccagcaaaagacgttttt (SEQ ID NO: 46) |
| 9b | #3 | agaaaccggccatcggacagtctggaa (SEQ ID NO: 63) |
| 91 | #4 | aagggacgaccgcgcagaccccgttcc (SEQ ID NO: 79) |
| 164 | #9 | aaaaccagaccatctccaaggctctcc (SEQ ID NO: 101) |
| 228 | #7 | tgaaatagaccgcgtatgcccgcatgc (SEQ ID NO: 116) |
| 245 | #8 | caaaaccgaccgcgaagaagtctgaaa (SEQ ID NO: 133) |
| 327 | #9 | taaaacgggccgcagatatgtcgtgca (SEQ ID NO: 152) |

Based on the phage sequence homology of the CRISPRo spacers shown in Table 3, in some embodiments of the present invention these homologous spacer sequences may be used in the methods to engineer altered phage resistance in bacterial strains described herein.

The *B. lactis* CRISPR loci sequences disclosed herein provide a source of repeat and spacer sequences that can be used in the methods for engineering altered resistance in other bacterial strains. Additionally, knowledge of the Bala1 and CRISPRo loci provides the necessary CRISPR locus "platform" for engineering *B. lactis* and other bifidobacteria. For example, CRISPR spacers from other organisms with known CRISPR-associated resistance characteristics may be inserted or otherwise engineered in the *B. lactis* Bala1 or CRISPRo loci.

In one embodiment, the sequences of the *B. lactis* Bala1 locus and its associated cas genes can be used in accordance with the above-described methods to alter resistance in a *B. lactis* strain against incoming nucleic acids, notably protection against phage attacks. In some embodiments, altered phage resistance is engineered in a bacteria with an CRISPR locus by introducing (i.e., inserting using recombinant DNA techniques) a Bala1 or CRISPRo spacer into the CRISPR locus of the bacterial genome, wherein the Bala1 or CRISPRo spacer has a sequence selected from the group consisting of SEQ ID NOs: 3-24, 43-52, 61-67, 76-82, 93-101, 110-116, 126-133, and 144-152.

In some embodiments of the various methods disclosed herein, altered phage resistance is engineered in a bacterial strain with a CRISPR locus by introducing a Bala1 or a CRISPRo repeat-spacer unit into the CRISPR locus of the bacterial genome. In such an embodiment, the Bala1 repeat-spacer unit comprises a repeat sequence selected from SEQ ID NO: 2 and variants thereof, and the spacer sequence selected from SEQ ID NOs: 3-24; and the CRISPRo repeat-spacer unit comprises a repeat sequence selected from SEQ ID NOs: 32-42, 53-60, 68-75, 83-92, 102-109, 117-125, and 134-143, and a spacer sequence selected from SEQ ID NOs: 43-52, 61-67, 76-82, 93-101, 110-116, 126-133, and 144-152.

In some embodiments of the above-described methods, the *B. lactis* CRISPR spacer sequence introduced into the existing CRISPR locus of a bacterium comprises a sequence having at least 98% identity, at least 99% identity, or at least 100% identity to a target nucleic sequence of the phage to which resistance is desired. In some embodiments, the target nucleic acid sequence is conserved in the phage, and in some embodiments comprises a sequence essential to phage survival.

In the various embodiments of the methods disclosed herein for altering resistance in cells, the engineering of a CRISPR locus in the cell for which altered resistance is desired may include, but is not limited to, adding (e.g. inserting), deleting (e.g., removing), or modifying (e.g., mutating) sequence of CRISPR spacers in the cell such that the CRISPR locus of the cell has homology (e.g., increased homology after the engineering) to at least one CRISPR spacer of an organism with a known CRISPR-associated resistance (e.g., a *B. lactis* cell). Such engineering can result in a cell that was substantially sensitive to a target nucleic acid or a transcription product thereof being substantially resistant to the target nucleic acid or a transcription product thereof.

In some embodiments, the invention provides a method for altering the resistance of a cell against a target nucleic acid, wherein the cell comprises a CRISPR locus and associated cas genes, said comprising: (a) identifying one or more resistance-associated CRISPR spacers in an organism resistant to the target nucleic acid; and (b) modifying the sequence of at least one spacer in the CRISPR locus of the cell such that its sequence is homologous or identical to the sequence of the resistance-associated CRISPR spacer. In embodiments of the present invention, the method is carried out wherein the organism resistant to the target nucleic acid is a bifidobacteria (e.g., *B. lactis*) and the resistance-associated CRISPR spacers are selected from the Bala1 and CRISPRo spacers having SEQ ID NOs: 3-24, 43-52, 61-67, 76-82, 93-101, 110-116, 126-133, and 144-152

In some embodiments, the methods provide for decreasing or reducing the resistance of a cell comprising at least one or more cas genes or proteins and one or more, preferably, two or more CRISPR repeats against a target nucleic acid or a transcription product thereof. According to this embodiment, the method comprises the steps of: (a) identifying one or more CRISPR spacers in an organism that is substantially resistant to the target nucleic acid or a transcription product thereof; and (b) modifying the sequence of one or more CRISPR spacer(s) in the cell such that the CRISPR spacer(s) has a reduced degree of homology to the CRISPR spacer(s) in the organism.

The various embodiments of the methods for engineering altered resistance to a target nucleic acid disclosed herein, can be used in a number of applications: (i) engineering resistance to phage; (ii) engineering resistance to plasmid transfer; (iii) engineering resistance to mobile genetic elements; (iv) engineering resistance to antibiotic resistance genes; (v) engineering resistance to genes encoding virulence factors; and (vii) engineering resistance to novel sequences. The various *B. lactis* CRISPR loci sequences and the associated repeat and spacer sequences disclosed herein provide a platform for engineering altered resistance in *B. lactis* and related bifidobacteria with related CRISPR loci.

Generally, in embodiments for altering resistance to phage, particular CRISPR spacers derived from bacteriophage DNA are added within a CRISPR locus of the bacterial cell so as to provide resistance against this particular bacteriophage and prevent phage attack. Additionally, particular regions within the phage genome (host specificity proteins) can be targeted that provide particular phage-host recognition, or that are highly conserved within phage DNA, such as sequences from helicase or primase genes, head and tail structural proteins, or proteins with conserved domains (e.g., helicase, holing, lysine, and others) or conserved sequences amongst important phage genes. Thus, knowledge of particular phage sequences can be used to modify existing CRISPR spacer sequences (e.g., spacers found in Bala1 and CRISPRo loci) to alter resistance to these particular phage.

In some embodiments, engineering altered resistance to plasmid transfer in a bacterial strain can be carried out in accordance to the methods disclosed herein. Particular CRISPR spacers derived from plasmid DNA are added within the existing CRISPR locus so as to provide resistance against this particular plasmid, thus preventing transfer of foreign DNA into cells of the strain. In some embodiments, particular regions within the target plasmid DNA, such as sequences within the plasmid's origin of replication, are selected for addition to the CRISPR locus so as to provide immunity against the plasmid DNA.

In some embodiments, methods for altering resistance to mobile genetic element are carried out in the same way by adding CRISPR spacers derived from mobile genetic element DNA can be added within the existing CRISPR locus of the bacterial strain so as to provide resistance against mobile genetic elements such as transposable elements and insertion sequences. Such engineered resistance can prevent transfer of foreign DNA and genetic drift in the engineered bacterial strain. Specifically, particular regions within transposons and insertion sequences can be targeted as to provide immunity against mobile genetic elements. For example, targets can include conjugative transposons (Tn97<5), class II transposons (Tn501), or insertions sequences (IS2d).

In some embodiments, methods for altering resistance to antibiotic resistance genes are carried out by adding CRISPR spacers derived from antibiotic resistance encoding genes within an existing bacterial strain's CRISPR locus. Such altered resistance can prevent transfer of genes conferring resistance to antibiotics into the bacterial host, thus reducing the risk of acquiring antibiotic resistance markers. For example, targets can include vanR, a gene conferring resistance to vancomycin, or tetR, a gene conferring resistance to tetracycline, or targeting beta-lactamase inhibitors.

In some embodiments, CRISPR spacer sequences derived from genes encoding virulence factors can be added within a bacterium CRISPR locus as to provide resistance against the transfer of genes conferring virulence into the bacterium. For example, factors commonly contributing to virulence in microbial pathogens can be targeted, such as toxins, internalins and hemolysins, In some embodiments, novel spacer sequences can be synthesized de novo, engineered and integrated into a CRISPR locus within a selected bacterial host as to provide resistance to a particular identical and novel sequence present into an infecting DNA molecule.

C. Strain Detection, Strain Typing, and/or Strain Tracking Using *B. lactis* CRISPR Sequences In some embodiments of the present invention, the Bala1 and/or CRISPRo loci sequences and portions of these sequences (e.g., repeats, spacers, and combinations thereof) can be used for detecting, tracking, and/or typing the bacteria in which they are present. Methods for strain detection, typing, and tracking using CRISPR sequences that can be used in the embodiments of the present invention are disclosed in e.g., U.S. published application 2006/01990190 A1, published Sep. 7, 2006, which is hereby incorporated by reference herein.

The Bala1 locus and at least one of the seven CRISPRo loci disclosed herein have been identified in all *B. animalis* strains tested so far. Nevertheless, differences between the sequence Bala1 and CRISPRo loci found in the different *B. animalis* strains tested can be detected. Thus, in some embodiments of the present invention, the presence of these sequence differences is used to detect, type, and/or track the particular strains that differ in these sequences.

In some embodiments, a strain is detected and/or distinguished from another strain (i.e., typed) by amplifying a portion of a CRISPR locus sequence in the strain that has been determined to distinguish it. Methods for amplifying specific genomic sequences in bacteria are well-known in the art (e.g., PCR, LCR, isothermal methods). Generally, a CRISPR locus or a portion thereof from a known source bacterium (e.g., the parent bacterium) and the unknown bacterium are amplified and/or sequenced using any suitable method known in the art. The determined sequences and/or the determined amplicons (e.g., based on size) are compared to determine if they are the same or different.

In some embodiments of the present invention, the CRISPR locus or a portion thereof from the source (or known) bacterium and the unknown bacterium (e.g., the analyte sample) are compared by amplifying the CRISPR locus or a portion thereof and comparing the characteristics of the amplicons (e.g., agarose gel electrophoresis analysis of amplicon size). In other embodiments of the present invention, a CRISPR locus or a portion thereof from the known source bacterium and the unknown source bacterium are compared by sequencing the CRISPR locus or a portion thereof from each and comparing the sequences.

In some embodiments of the present invention, strain detecting, typing, and/or tracking is carried out by a method comprising: (a) amplifying genomic DNA from a strain of interest using at least one primer pair, wherein the genomic DNA comprises at least a portion of a sequence of a CRISPR locus; and (b) detecting an amplicon generated in step (a), whereby said detected amplicon indicates the strain type. In some embodiments, each primer of the pair is complementary to at least a portion of a sequence of a CRISPR locus.

Typically, PCR is used to amplify the genomic DNA obtained from the strain of interest. Using the CRISPR sequences disclosed herein, or sequences found in published bacterial genomes, it is straightforward to determine distinguishing CRISPR sequences (e.g., that differ in number of repeats or spacers) and design PCR primer pairs that can be used to amplify the regions that contain these sequences.

In some embodiments, bacteria are compared by amplifying and then sequencing the CRISPR locus or a portion thereof. For example both the 5' and 3' ends of the loci may be amplified and/or sequenced and are compared.

In some embodiments, one end (e.g., the 5' end) of the CRISPR loci are compared. In yet other embodiments, at least the last CRISPR repeat at the 3' end of the CRISPR locus and/or at least the last CRISPR spacer at the 3' end of the CRISPR locus and/or at least the first CRISPR repeat at the 5' end of the CRISPR locus and/or at least the first CRISPR spacer (e.g., the first CRISPR spacer core) at the 5' end of the CRISPR locus are compared. In some embodiments, at least the first CRISPR repeat at the 5' end of the CRISPR locus and/or at least the first CRISPR spacer (e.g., the first CRISPR spacer core) at the 5' end of the CRISPR locus are compared. In some additional embodiments, at least the last CRISPR spacer (e.g., the last CRISPR spacer core) at the 3' end of the CRISPR locus and/or at least the first CRISPR spacer (e.g., the first CRISPR spacer core) at the 5' end of the CRISPR locus are compared. In some further embodiments, at least the first CRISPR spacer (e.g., the first CRISPR spacer core) at the 5' ends of the CRISPR loci is compared.

In one embodiment of strain detecting, typing, and/or tracking, the distinguishing CRISPR feature is the number of repeat-spacer units found in the CRISPR locus. That is, one strain may have 12 repeats and 11 spacers, and another strain may have only 8 repeats and seven spacers. Amplification of the CRISPR regions of these two strains will result in PCR amplicons of greatly differing sizes. Detecting this amplicon and determining its size and how it differs from another strain provides one embodiment for strain typing.

Because CRISPR loci generally evolve by adding new repeat-spacer units to the 5' end of the repeat-spacer portion of the CRISPR locus, in some embodiments a method for detecting or typing a newly evolved strain includes generating an amplicon that includes the 3' end of the CRISPR leader. Thus, in some embodiments, the method of strain typing comprises using a primer designed to hybridize to a sequence comprising the 3' end of the CRISPR leader. In one embodiment, the primer hybridizes to the sequence comprising the 3' end of the CRISPR leader and the 5' end of the first repeat.

In one embodiment, changes in a strain can be tracked by amplifying samples of the strain over time. Changes in the fast evolving CRISPR sequences will manifest as changes in the size of the detected amplicon. For example, if new repeat-pairs are added to the 5' end of the CRISPR region, this will result in an increase in the size of the largest amplicon detected for a strain.

In one embodiment, this method of strain detecting, typing and/or tracking can be used to detect man-made changes to a CRISPR, e.g., engineering a phage resistance by introduction of a new spacer into an existing CRISPR locus. Thus, it is contemplated that the methods of strain detecting, typing and/or tracking can be used to monitor the strain tagging embodiments disclosed herein. For example, where a bifidobacterial strain is tagged with a CRISPR spacer following exposure to a phage, the incorporation of the new repeat-spacer unit can be monitored by the methods of strain detecting, typing and/or tracking described above.

Generally, in the strain detecting, typing, and tracking embodiments of the present invention, a PCR amplicon is generated using amplicons complementary to region of the Bala1 or CRISPRo loci sequences found in genomic samples from two *B. lactis* strains. A detected difference in the amplicons from the two samples (determined based on a difference in the sequence and/or size of the amplicons) is indicative of a difference in the number of repeat-spacer units present in the CRISPR loci from the two strains. Where the two bifidobacteria samples are found to be identical, it can be concluded that they are the same type. Where the two samples include an archival sample of a strain and a sample prepared after the bifidobacterial strain has undergone many generations in an industrial process, the comparison between the two track whether the strain has undergone changes due to phage exposure or other treatments. Where one sample is a parent strain and the other is the same parent strain after exposure to a phage, the comparison can confirm if the strain has been tagged with a CRISPR spacer.

D. Strain Tagging Using *B. Lactis* CRISPR Sequences

In some embodiments the present invention provides methods of tagging bacterial strains using the Bala1 and/or CRISPRo loci sequences, or portions of these sequences (e.g., repeats, spacers, and combinations thereof). Methods for strain tagging with CRISPR sequences useful in the embodiments of the present invention are disclosed in e.g., U.S. published application 2008/0124725 A1, published May 29, 2008 which is hereby incorporated by reference herein.

Typically, in the strain tagging embodiments, a bacterial strain to be tagged is exposed to a phage and the infection induces the addition of a CRISPR sequence (e.g., a repeat-spacer unit) to the CRISPR locus in the bacterial strain. This added repeat-spacer acts as a genetic tag (i.e., marker sequence) for that bacterial strain which can be detected using any of the well-known methods described above in the context of strain typing, detecting, and tracking (e.g., PCR, sequencing, immobilized probe hybridization).

Thus, in some embodiments the present invention provides a method for tagging a bifidobacterial strain comprising: exposing cells of a corresponding parent strain comprising at least a portion of a CRISPR locus to at least one exogenous nucleic acid sequence, thereby producing a tagged bacterial cell with a CRISPR locus comprising at least one more repeat-spacer unit than the corresponding parent strain cells.

In some embodiments, the present invention provides methods for tagging a bacterial strain comprising: (a) exposing a parent bacterial strain to a phage; (b) selecting a phage insensitive mutant; (c) comparing a CRISPR locus or a portion thereof from the parent strain and the phage insensitive mutant strain; and (d) selecting a tagged bacterial strain comprising an additional repeat-spacer unit in the CRISPR locus that is not present in the parent bacterial strain.

In alternative embodiments, the present invention provides methods for tagging the CRISPR locus of a bacterial strain using recombinant DNA techniques as known in the art rather than exposure to phage. For example, in some embodiments, synthetic oligonucleotides are produced and used to transform parent bacteria to produce CRISPR tagged bacteria.

The *B. lactis* CRISPR loci sequences disclosed herein provide a source of repeat and spacer sequences that can be used in the methods for tagging other bacterial strains. Additionally, the Bala1 and CRISPRo loci sequences disclosed herein provide target CRISPR loci that can be tagged with spacers from other sources. For example, CRISPR spacers from other organisms with may be inserted or otherwise engineered in the *B. lactis* Bala1 or CRISPRo loci. The knowledge of the Bala1 or CRISPRo loci sequence disclosed herein thereby provides the background for recognizing whether a strain has been tagged.

Thus, in some embodiments, the present invention provides a tagged bacterial strain, wherein the strain is not *B. lactis* and comprises a CRISPR locus comprising a Bala1 or CRISPRo spacer sequence selected from SEQ ID NOs: SEQ ID NOs: 3-24, 43-52, 61-67, 76-82, 93-101, 110-116, 126-133, and 144-152.

To infect cells, a phage injects or transfers its nucleic acid into the cell with the phage nucleic acid existing independently of the cell's genome. In some embodiments, infection results in the expression (i.e., transcription and translation) of the phage nucleic acid within the cell and continuation of the phage life cycle. Thus, in some embodiments of the present invention, following exposure to a phage, the bacterial strain not only is tagged but also gains resistance to further phage infection and/or multiplication when compared to the corresponding parent bacterial strain.

In some embodiments, the tagged bacterium is insensitive or substantially insensitive to further infection and/or multiplication by the phage. In additional embodiments, the tagged bacterium is insensitive or substantially insensitive to one or more of the mechanisms that the phage uses to infect and/or multiply in a bacterium. In still further embodiments, the tagged bacterium is insensitive or substantially insensitive to all of the mechanisms that the phage uses to infect and/or multiply in a bacterium. In yet additional embodiments, the tagged bacterium develops one or more mechanisms that attenuate, inactivate or destroy the phage during the infection cycle. Thus, in some embodiments, the present invention provides tagged strains selected by standard screening procedures that are known in the art to isolate phage insensitive mutants.

In further embodiments, the invention provides cell cultures comprising the tagged bacterial strains made according to the above methods.

The manner and method of carrying out the present invention may be more fully understood by those of skill in the art by reference to the following examples, which examples are not intended in any manner to limit the scope of the present invention or of the claims directed thereto.

EXAMPLES

The following Examples are provided in order to demonstrate and further illustrate specific embodiments and aspects of the present invention and are not to be construed as limiting the scope thereof.

In the experimental disclosure which follows, the following abbreviations apply: ° C. (degrees Centigrade); $H_2O$ (water); $dH_2O$ (deionized water); HCl (hydrochloric acid); aa (amino acid); bp (base pair); kb (kilobase pair); kD (kilodaltons); g (grams); µg (micrograms); mg (milligrams); µl (microliters); ml (milliliters); mm (millimeters); µm (micrometer); M (molar); mM (millimolar); µM (micromolar); MW (molecular weight); s (seconds); min(s) (minute/minutes); hr(s) (hour/hours); NaCl (sodium chloride); PBS (phosphate buffered saline [150 mM NaCl, 10 mM sodium phosphate buffer, pH 7.2]); PCR (polymerase chain reaction); SDS (sodium dodecyl sulfate); w/v (weight to volume); v/v (volume to volume); ATCC (American Type Culture Collection, Rockville, Md.); BD BioSciences (Previously CLONTECH Laboratories, Palo Alto, Calif.); Invitrogen (Invitrogen Corp., San Diego, Calif.); and Sigma (Sigma Chemical Co., St. Louis, Mo.).

Example 1

PCR Detection of the *B. lactis* Bala1 Locus

This example illustrates how PCR amplification can be used to detect the Bala1 locus in *B. lactis* strain of *Bifidobacterium* and distinguish that strain from other bifidobacterial strains having a Bala1 locus.

Based on the sequence of *B. lactis* Bala1 locus (SEQ ID NO: 1), a pair of PCR primers were designed.

Primer 1 is a 24-mer oligonucleotide having the sequence: 5'-TGAGGGaagccgaactcaatcaca-3' (SEQ ID NO: 153) Primer 1 is complementary to the antisense strand of the 24 bp Bala1 sequence spanning a portion of repeat R4 and a portion of the adjacent spacer S4 (see Table 1 above). The portion of Primer 1 overlapping with repeat R4 is shown in all capital letters.

Primer 2 is a 24-mer oligonucleotide having the sequence: 5'-ttggatgcaagCCCTCAATGAAGC-3' (SEQ ID NO: 154). Primer 2 is complementary to the 24 bp Bala1 sequence spanning a portion of repeat R16 and a portion of the adjacent spacer S16 (see Table 1 above). The portion of Primer 2 overlapping with repeat R16 is shown in all capital letters.

The pair of Primer 1 and Primer 2 is designed to generate an amplicon comprising the 12 Bala1 repeat-spacer units including all spacers from spacer S4 through spacer S15 (see FIG. 2 and Table 1). The size of the generated Bala1 amplicon is predicted to be 874 bp.

The Primer 1 and 2 pair was used in a PCR reaction with samples from four different strains of *B. lactis* (strains: BI-04, Bi-07, HN019, and B420), and four other bifidobacteria species: *B. bifidum* (Bb-06), *B. longum* (BI-05), *B. infantis* (Bi-08), and *B. breve* (Bb-03). In addition, a sample (Bb-02) containing a mixture of *B. bifidum* and *B. lactis* was amplified.

The samples were amplified under standard PCR conditions to generate labeled amplicons. The PCR mix (per 50 µl reaction) included: Eppendorf mastermix (20 µl); water (27 ul); Primer 1 (forward primer) (1 ul); Primer 2 (reverse primer) (1 ul); Template DNA (1 ul). Initial denaturation was carried out for 5 minutes at 95° C. Thermal cycling included: 30 cycles of: 30 s denaturation at 95° C. 30 s annealing at 58° C., and 1 min extension time 72° C. Final extension was carried out for 5 minutes at 72° C.

Following amplification, the PCR reaction mixtures were analyzed by agarose gel electrophoresis to determine the relative size of the labeled amplicons.

A single bright band was detected in the lanes of the agarose gel image corresponding to the BI-04 and Bi-07 strain samples consistent with the presence of an amplicon of approximately 870 bp which is predicted based on the *B. lactis* Bala1 sequence (SEQ ID NO: 1) and the design of Primers 1 and 2. In contrast, the lanes of the gel image containing the *B. lactis* strains HN019 and B420 did not have the 874 bp band but instead each had a single bright band consistent with a PCR amplicon of approximately 650 bp which is predicted based on their CRISPR sequences have three fewer spacers. Thus, as predicted, the observed amplicon sizes from strains HN019 and B420 correspond to 9 repeat-spacer units as opposed to the amplicons comprising 12 units for the BI-04 and Bi-07 strains.

The lane of the agarose gel containing the Bb02 sample (which was a mixture of BI-04 *B. lactis* and *B. bifidum*) also showed a single bright band consistent with an 874 bp amplicon as expected due to the presence of the BI-04 strain in the sample. However, the PCR reactions using the samples from the four other bifidobacteria species did not yield a detectable amplicon. This indicates that the sequences of any CRISPR loci found in these species is sufficiently different to preclude amplification using these primers.

The observed differences in the amplicons generated from the different *B. lactis* strains plainly illustrate the ability of this fundamental amplification-based method to be exploited for strain typing, detection and/or tracking.

One of ordinary skill will recognize that this method could also be easily applied in other embodiments of the invention including detecting whether specific repeat-spacer units have been incorporated into a strain's CRISPR locus in response to strain tagging or phage resistance alteration experiments as described elsewhere herein.

Those of skill in the art readily appreciate that the present invention is well adapted to carry out the objects and obtain the ends and advantages mentioned, as well as those inherent therein. The compositions and methods described herein are representative, exemplary embodiments, and are not intended as limitations on the scope of the invention.

While particular embodiments of the present invention have been illustrated and described, it will be apparent to those skilled in the art that various other changes and modifications can be made without departing from the spirit and scope of the invention. It is therefore intended to cover in the appended claims all such changes and modifications that are within the scope of this invention.

The invention illustratively described herein suitably may be practiced in the absence of any element(s) or limitation(s) which is not specifically disclosed herein. The terms and expressions which have been employed are used as terms of description and not of limitation, and there is no intention that in the use of such terms and expressions of excluding any equivalents of the features shown and described or portions thereof.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

All patents and publications are herein incorporated by reference to the same extent as if each individual publication was specifically and individually indicated to be incorporated by reference.

What is claimed is:

1. A method for strain typing Bifidobacteria wherein:
the method comprises:
(a) amplifying, using an at least one primer pair, a genomic DNA sequence from a CRISPR locus of a Bifidobacteria strain of interest, wherein said CRISPR locus consists of at least one Clustered Regularly Interspaced Short Palindromic Repeats (CRISPR) repeat(s) between two CRISPR spacer(s) wherein said at least one CRISPR repeat consists of:

SEQ ID NO: 2; or

SEQ ID NO: 2 comprising at least one mutation selected from the group consisting of:

substitution of Cytosine for Thymine at position 12,
substitution of Cytosine for Thymine at position 14, and
substitution of Guanine for Adenine at position 36 wherein each primer of the at least one primer pair is complementary to at least a portion of the repeat sequence consisting of SEQ ID NO: 2 or variant thereof, and to a portion of the adjacent spacer, and wherein each primer is selected to create an amplicon comprising at least one spacer sequence of the CRISPR locus; and (b) detecting the amplicon generated in step (a), whereby said detected amplicon indicates a Bifidobacteria strain type.

2. A method for strain typing Bifidobacteria wherein: the method comprises:

(a) amplifying, using an at least one primer pair, a genomic DNA sequence from a CRISPR locus of a Bifidobacteria strain of interest, wherein said CRISPR locus consists of at least two CRISPR spacer(s) surrounding one Clustered Regularly Interspaced Short Palindromic Repeats (CRISPR) repeat(s), wherein said at least one CRISPR repeat comprises:

SEQ ID NO: 2; or

SEQ ID NO: 2 comprising one or more mutations selected from the group consisting of:

substitution of Cytosine for Thymine at position 12,
substitution of Cytosine for Thymine at position 14, and
substitution of Guanine for Adenine at position 36 wherein each primer of the at least one primer pair is complementary to at least a portion of a different spacer sequence of the CRISPR locus, thereby creating an amplicon comprising at least one repeat sequence located between the two spacer sequences of the CRISPR locus; and (b) detecting the amplicon generated in step (a), whereby said detected amplicon indicates a Bifidobacteria strain type.

3. The method of claim 1 or 2, wherein the CRISPR locus is Bala1 comprising SEQ ID NO: 1.

4. The method of claim 1 or 2, wherein detecting the amplicon includes hybridizing the amplicon to an immobilized probe.

5. The method of claims 1 and 2, wherein the spacer sequence is selected from the group consisting of SEQ ID NOs: 3 to 24.

6. The method of claim 1 or 2, further comprising the step of:

(c) detecting the size of the amplicon.

* * * * *

SEQUENCE LISTING

<160> NUMBER OF SEQ ID NOS: 162

<210> SEQ ID NO 1
<211> LENGTH: 1819
<212> TYPE: DNA
<213> ORGANISM: Bifidobacterium animalis

<400> SEQUENCE: 1

```
ctatcccgtg cgagggctgc atcatgcagc ataaagcggg gaatctctcg catcaatact      60
ttgtaaggat ttgttgagtt tgtgtagata aatcagtcgt ttgtatcacg tcaatttgtc     120
tacctctcgc aaaagcgctt atcagactat gtgtatcagt ctgtattatg gctactatct     180
ccgaagtctc ggcttcggag cttcattgag gggacgatat ggcgctcagc gtggcggagt     240
gggaggcgga tctccgaagt ctcggcttcg gagcttcatt gagggaagac cggcaccgaa     300
cgcgacttca ccatgacctc atctccgaag tctcggcttc ggagcttcat tgaggggccc     360
accacaacgg caacggcgga ggaacacgcg ccgaaatctc cgaagtctcg gcttcggagc     420
ttcattgagg gaagccgaac tcaatcacac gcatcaaagc gaacaatctc cgaagtctcg     480
gcttcggagc ttcattgagg ggtattcgcc gttcgagagg aatgagagga tgctgtcaga     540
tctccgaagt ctcggcttcg gagcttcatt gagggtcgcc attggagacg cgacgcagga     600
tactatccga tctccgaagt ctcggcttcg gagcttcatt gagggacgac aagccgccgc     660
caccgatatt cacctgcgaa tctccgaagt ctcggcttcg gagcttcatt gaggggggccg     720 cttcggtgac gggctggttt ttccaccaca cgcatctccg aagtctcggc ttcggagctt     780
cattgaggga atcccagccg caaggtctga tgccgcctga aatatctccg aagtctcggc     840
ttcggagctt cattgagggc actggtggtg cgaatacgcc gaaacggtgg aatggatctc     900
cgaagtctcg gcttcggagc ttcattgagg gattgagatt gataccgtg gcgccgctga     960 tgagacatct ccgaagtctc ggcttcggag cttcattgag gaatccctc ggcccatgat    1020 tcgtcacgtg gatcacatc tccgaagtct cggcttcgga gcttcattga gggaaacagg    1080
tcaatcagcg gcgcagggag gagacgaaat ctccgaagtc tcggcttcgg agcttcattg    1140
aggggagtga acaactcact gtgcgaacca tcgaaccgtt atctccgaag tctcggcttc    1200
ggagcttcat tgagggcggt tgagcagcca cgtggtgata ctgctcgcgc caatctccga    1260
```

```
agtctcggct tcggagcttc attgagggct tgcatccaac gcgcacagca ttgcatacgg    1320
gtatagatct ccgaagtctc ggcttcggag cttcattgag ggatcatcct cacggaaata    1380
gtgagcatcc tcgagaacct gatctccgaa gtctcggctt cggagcttca ttgagggggc    1440
cgcgatagtc cacgaggcga acgaaggcgt tgcatctccg aagtctcggc ttcggagctt    1500
cattgagggg ctcaagacac tcaccgacca gctcaagaag accgaatctc cgaagtctcg    1560
gcttcggagc ttcattgagg gcgcgatcgt caccgactgc actgtgttcg cactgtcatc    1620
tccgaagtct cggcttcgga gcttcattga ggggcgacac cgaacgccgc cgccacagtc    1680
gggatggcat ctccgaagtc tcggcttcgg agcttcattg aggaagggcc agcaacgtcg    1740
tggagatcca tcaggaggca tctccgaagt tttggcttcg gagcttcatt gaggaatgta    1800
ctccgatttt tatctaagc                                                 1819

<210> SEQ ID NO 2
<211> LENGTH: 36
<212> TYPE: DNA
<213> ORGANISM: Bifidobacterium animalis

<400> SEQUENCE: 2
atctccgaag tctcggcttc ggagcttcat tgaggg                               36

<210> SEQ ID NO 3
<211> LENGTH: 37
<212> TYPE: DNA
<213> ORGANISM: Bifidobacterium animalis

<400> SEQUENCE: 3
gacgatatgg cgctcagcgt ggcggagtgg gaggcgg                              37

<210> SEQ ID NO 4
<211> LENGTH: 35
<212> TYPE: DNA
<213> ORGANISM: Bifidobacterium animalis

<400> SEQUENCE: 4
aagaccggca ccgaacgcga cttcaccatg acctc                                35

<210> SEQ ID NO 5
<211> LENGTH: 39
<212> TYPE: DNA
<213> ORGANISM: Bifidobacterium animalis

<400> SEQUENCE: 5
gcccaccaca acggcaacgg cggaggaaca cgcgccgaa                            39

<210> SEQ ID NO 6
<211> LENGTH: 34
<212> TYPE: DNA
<213> ORGANISM: Bifidobacterium animalis

<400> SEQUENCE: 6
aagccgaact caatcacacg catcaaagcg aaca                                 34

<210> SEQ ID NO 7
<211> LENGTH: 38
<212> TYPE: DNA
<213> ORGANISM: Bifidobacterium animalis

<400> SEQUENCE: 7
gtattcgccg ttcgagagga atgagaggat gctgtcag                             38
```

<210> SEQ ID NO 8
<211> LENGTH: 34
<212> TYPE: DNA
<213> ORGANISM: Bifidobacterium animalis

<400> SEQUENCE: 8
tcgccattgg agacgcgacg caggatacta tggc          34

<210> SEQ ID NO 9
<211> LENGTH: 34
<212> TYPE: DNA
<213> ORGANISM: Bifidobacterium animalis

<400> SEQUENCE: 9
acgacaagcc gccgccaccg atattcacct gcga          34

<210> SEQ ID NO 10
<211> LENGTH: 38
<212> TYPE: DNA
<213> ORGANISM: Bifidobacterium animalis

<400> SEQUENCE: 10
ggccgcttcg gtgacgggct ggttttttcca ccacacgc     38

<210> SEQ ID NO 11
<211> LENGTH: 34
<212> TYPE: DNA
<213> ORGANISM: Bifidobacterium animalis

<400> SEQUENCE: 11
aatcccagcc gcaaggtctg atgccgcctg aaat          34

<210> SEQ ID NO 12
<211> LENGTH: 36
<212> TYPE: DNA
<213> ORGANISM: Bifidobacterium animalis

<400> SEQUENCE: 12
cactggtggt gcgaatacgc cgaaacggtg aatgg         36

<210> SEQ ID NO 13
<211> LENGTH: 35
<212> TYPE: DNA
<213> ORGANISM: Bifidobacterium animalis

<400> SEQUENCE: 13
attgagattg atacccgtgg cgccgctgat gagac         35

<210> SEQ ID NO 14
<211> LENGTH: 35
<212> TYPE: DNA
<213> ORGANISM: Bifidobacterium animalis

<400> SEQUENCE: 14
aatccctcgg cccatgattc gtcacgtggg atcac         35

<210> SEQ ID NO 15
<211> LENGTH: 35
<212> TYPE: DNA
<213> ORGANISM: Bifidobacterium animalis

<400> SEQUENCE: 15
aaacaggtca atcagcggcg cagggaggag acgaa                              35

<210> SEQ ID NO 16
<211> LENGTH: 36
<212> TYPE: DNA
<213> ORGANISM: Bifidobacterium animalis

<400> SEQUENCE: 16
gagtgaacaa ctcactgtgc gaaccatcga accgtt                             36

<210> SEQ ID NO 17
<211> LENGTH: 36
<212> TYPE: DNA
<213> ORGANISM: Bifidobacterium animalis

<400> SEQUENCE: 17
cggttgagca gccacgtggt gatactgctc gcgcca                             36

<210> SEQ ID NO 18
<211> LENGTH: 38
<212> TYPE: DNA
<213> ORGANISM: Bifidobacterium animalis

<400> SEQUENCE: 18
cttgcatcca acgcgcacag cattgcatac gggtatag                           38

<210> SEQ ID NO 19
<211> LENGTH: 39
<212> TYPE: DNA
<213> ORGANISM: Bifidobacterium animalis

<400> SEQUENCE: 19
atcatcctca cggaaatagt gagcatcctc gagaacctg                          39

<210> SEQ ID NO 20
<211> LENGTH: 36
<212> TYPE: DNA
<213> ORGANISM: Bifidobacterium animalis

<400> SEQUENCE: 20
ggccgcgata gtccacgagg cgaacgaagg cgttgc                             36

<210> SEQ ID NO 21
<211> LENGTH: 36
<212> TYPE: DNA
<213> ORGANISM: Bifidobacterium animalis

<400> SEQUENCE: 21
gctcaagaca ctcaccgacc agctcaagaa gaccga                             36

<210> SEQ ID NO 22
<211> LENGTH: 36
<212> TYPE: DNA
<213> ORGANISM: Bifidobacterium animalis

<400> SEQUENCE: 22
cgcgatcgtc accgactgca ctgtgttcgc actgtc                             36

<210> SEQ ID NO 23
<211> LENGTH: 35
<212> TYPE: DNA
<213> ORGANISM: Bifidobacterium animalis

<400> SEQUENCE: 23

```
gcgacaccga acgccgccgc cacagtcggg atggc                          35

<210> SEQ ID NO 24
<211> LENGTH: 35
<212> TYPE: DNA
<213> ORGANISM: Bifidobacterium animalis

<400> SEQUENCE: 24
agggccagca acgtcgtgga gatccatcag gaggc                          35

<210> SEQ ID NO 25
<211> LENGTH: 970
<212> TYPE: DNA
<213> ORGANISM: Bifidobacterium animalis

<400> SEQUENCE: 25
atctggtaca ccaccgcgtt cgcccaccac gggttcggcg tcgcgccgtt cgtacgcacg    60
gaatcgggaa gcacaggcct attcattgtg gtcatggaag ctcctttgcc tttgaataac   120
aaccgccaac actatagaga tggctccata gtaggcaccc ctgaattaat tgcctagcgt   180
agtatgcgga cgggcgtgtg ggaaagtaat tccgcggtca catgcacggg aatcttcgca   240
aaatcgacca tatacggcgt ttgcgcggca tactttacgg aagtctccgc aaggaatgcc   300
atgctggagc tcttttgcgg tcggtcatgc ggaagcatcc gtaaaccatg ccgcggcgga   360
gtctgcaaat gatgtatctt acggaacgct ccgagaacca tgccagcaaa agacgttttt   420
gcggtccgtc tcaaggaaac ttccgaaaac catgccacaa gaagcgcta ttgcggcgca   480 tcttacggaa gcttccgaaa acacggcgc aaacgggtac ccctgcggca tatctcacgg   540
aagactccgc acaatgaacc gcgaagagaa caatctgcgg atcagtttgc ggaagactcc   600
gagaaacaaa ccgttttgag accaccgcgc ggtcggtcat gcggaaggtt ccgagtaatg   660
gggcgccaca gcggcaatct gtggcacgtc gtacggaagg ttccgagaaa cacaccaagg   720
aggaatccag aaatggcata tcttacggaa gcttccgaaa acaagccac aaacaaagcg   780 caaaacagca cttccaagcg cccataggcg ctgaatacgg tggacaacgg cgaagttatc   840
cacaaattcc aaatcgggat tgcacgacat tcgacactct cctaccgtcg aaagcatgaa   900
gatagattcg caaatcgagc gactcctcga cgagtcccag aacgcacacc gatgcgcggt   960
gacgaccgac                                                         970

<210> SEQ ID NO 26
<211> LENGTH: 836
<212> TYPE: DNA
<213> ORGANISM: Bifidobacterium animalis

<400> SEQUENCE: 26
aatggacgca tgatcgtcgc cgaatacgac ggcatgacga aatacggcaa tgaccgcaag    60
accatcgcaa accacgtgca ccgggagaaa ctgcgcgacg aagcgctgcg gcaacacggc   120
gtcaccgcga tcatccattt cgattatgag gatttgctca atcccaacga actcattgcc   180
aggctcgtcg ccgccggtgt gccgtaccgc cgctgagcat gcagcggatc tggtcgcggc   240
atggtatgcg gaagattctg agaaccgtgc cgcaaacgta gacttttgcg gtcgatcatg   300
cggaagactc cgtaaaccgt gcctcaaaag gcatcccgcg cggcacgtct tacgggaagt   360
tccgagaaac cggccatcgg acagtctgga aactgcactt cctaagggcg cctccatgaa   420
actggctgcg aaaggagctt atgcggcatg gcttacggaa ggttccgaga gtcgtaccgc   480
```

```
aaatggagac ttccgcggtc agtcttacgg aaggttccgt gaaagcgact atattcaggt      540
cactttgcgg tcgaatatac ggacgactcc gaaaaacaga ccacgaaacg gggtctgtgc      600
ggtacagctt acggaagact ccgagagctg tgccgaaaat acacgcgggc gccggattat      660
gtgagagtct gcaatatgcg cagctcgcac tcgccataat gcagcgtgag cgcgaggtct      720
tcgccgacgc tcagatgcac gcgctcgccg gtctgcggat cgaacaccgt gagaggagat      780
tccgtcgcgc gaatgtgggc ggtctgcggg gcatcggcgt tcaatccgac gaacag         836
```

<210> SEQ ID NO 27
<211> LENGTH: 1479
<212> TYPE: DNA
<213> ORGANISM: Bifidobacterium animalis

<400> SEQUENCE: 27

```
tgcttcacaa tgtccaggaa gtctttgtcc tgcacatgca gataggtgct gaaaccatct       60
gttcgccgca ttttcaacat aggcatacca ggacactcct ctggagttag acctggttca      120
cagtagctga aaatccagta tggtccatac tccaccacag agatgatctg gagatgcgat      180
tgcatctcgg ccgccttgcg caatgcttcc tgaatgccca taccacaccg ccccacagca      240
tgaacgctta actacatgga gcgaagtctg cggaacctgt gcgatcttct cttcacaaga      300
agagtcaaaa cacagctccc accgtccctt tttacgcaga agcgatttcg ggagattagc      360
gttcgccgcc gttccgcagc cgcgcaccaa ctgccccgca catcagaact cttcctcgca      420
atcattgcag tgatagctcg gcgtcgggtg gaaaatgtcg atgtcgcagc cgcccagcac      480
caccttgccc tcagcgagct cacgctgcag ttcctcagtg aacgcaggca taccatgcag      540
aatctgcgcc acatgccgcg agccacaccg tgggcacacc acctcgccg attccacatt       600 ttccgcatcc atgtctgcgt aatctcccat attcgccatt ctcgtcgccc tcctcggttc      660
cgcaaacagc ataggcacgc ctttcgcatt ctcagatttc ctcaccgctc ttcccatctt      720
ctcaagtatc tatatttccc ttcctctctg aattttctcg acataacaga gtcaaaatca      780
cacccagtcg tccgctctgc aagaagagcg gtacccgagc cagcgaggca cgtttcacgg      840
aaacatccgc ataaccgacc accaagtcac gcagatgtgg ctcgtcttc ggaagcttcc       900 gaacgatatg tcgtctgcag acttccccgc agcacattcc acggaatctt ccgtaagata      960
tgccattcac agaccattct gcggcacagc tcacggaaac atccgaaggg acgaccgcgc     1020 agacccgtt ccacggcaca acgtacggaa gcttccgtaa gatacgtcat tctcagacca      1080
ctctgcggca cagctcacgg acgcttccgc aaaaccggcc gccaaagcga tatctacggc     1140
acagctcacg gaaacatccg caatctatgc cgcaaaatgc gcacatcgcg acctgattca     1200
tggaagcatc cgcgtaatcg accacagaac cgcggctgta tgcccaacc cgtagcgcac      1260 ctccttatct gcgtaaaaag agtcaaataa tctttctcac cgactctttt tacgcaaaca     1320
aacgccatac acatctcacg ccggagaatg agccaatctc agtcagtcga caacgacgcc     1380
gggtttgcca atctcgtcga gccgataggc aatctccgct ttcgatccct cttccgccac     1440
aattttcacc gtgctgcttt tcgcattcac attgctcat                            1479
```

<210> SEQ ID NO 28
<211> LENGTH: 2001
<212> TYPE: DNA
<213> ORGANISM: Bifidobacterium animalis

<400> SEQUENCE: 28

```
gcggcacgag atgctcggta cgcacgccgg cgcccacctg tgcgcgcacg ccgtcatctc       60
```

```
ccaccgtgta cgcgagcgcg tcccaatcga ttgtcgtcac gaacagctcg ccgttcacgg      120
tgaaggcgac atgattgccc agaccgtcca ccgagtacgc aacgatcccg gtggcgctct      180
ccctcgcacg ttcacgacgc gcacgctcgg cagcaggcac gtcgtcgctg cccagtgtgt      240
tcacgagctc acccgcgttc acgagctcca cttcggcata cgcgtcttcc ccgcagattg      300
ccagccacag cgaattctcg gtgtcctgct cgcccgcgga ccgtaggaac agcatgcgcg      360
atccgtcgcc gatgagcttg ggagagcgcg gcgccccgca tgtgaaccgc accgttttcg      420
ctttgcgcac tgggtattct tcgattgcag attccatccc gcacctctcg tctcatcgga      480
tcatctattc gttcccactc tatcctgctt cacggaacct tccgtaaaac aggtcgcaga      540 ctcccctttcc cgcggcacct cccacggaac cttccgcaat accgaccact ggcgactctc      600
ccggcggcac agctcacgga agctcccgta aatctgacca ctggaagccc atcggcggc      660 acagtttccg gaaccatccg aaaatcagac cacagatgac cttccccgcg gcacattgca      720
cggaaacatc cgaaagactg accacggcga cactgattta cggcacagct tgcggaaaca      780
tccgcagatt cggccacaac ggcacccatt tacggcatgg ttcacggaaa catccgaaaa      840
ccatgccacg gcagcgctga tttacggcac agcatacgga accatccgta agatctgccg      900
cctaaggaca catctgcaga ccactccacg gaaccttccg aaaaccagac catctccaag      960
gctctccgcg gcaccgctca cggaagcatc cgcaatacag accgcaaata catcggccga     1020
acgattgcgg attcctgtgg gtccggcgca tagtaggcaa tgtggaaacc gcgggaacaa     1080
ggtggggccg tatgcgtgca gtgaaacggc aaaccgttgc aatccatacg ctcccagagg     1140
aaaacgcggc ggaccgatgc gcctgaaaat tcacacggtt gatatataag cgtaggatag     1200
gtaaggatag aaagggtaac tatgagcgtt cttgatcgtt ttgagaaaag cgtggagggt     1260
gcggtcaacg gagtgttcgc gaagttcggc tccaaagacc tgcagcccgt cgatctctcc     1320
agcgcgcttg agcgcgaaat cgacgccgag gccatgccgg tcggccgaga ccgcaccgtg     1380
gcgccgaacg agtaccgttt caaactgagc acacccgatt tcgaccgcat cgaaagctgg     1440
ggttccgagg ccatggccaa tgagctggcc gacaatctca cgcagtacgc gaagagccaa     1500
cactatgcat ttgtgggccc ggtcgtcgtt attttcgaag aggacctgca actgaccaaa     1560
ggcaacttca agctcacgtc cgaatccgtg cagggcaacg ccgtaccggt caccactgac     1620
gagcaggcca aggactgccc gatgctcgaa gtcaacaaca accaataccct gctcaccaaa     1680 gacaagacga ttctgggtcg cggctcgggc tgcgacattg tgattgacga ccccggcatc     1740
tcccgcaaac acctggagat cgacatcacg gacaacggtg tgatcgcccg cgacttgggc     1800
tccacgaacg gcacgtatgt ggagggccat caggttcccg ccgcgacgct gctcgatggc     1860
aacacgatca cgatcggccg cacccgcatc ctgtactggg cctcctcaca agaccagagg     1920
tgagcgtagc gggattttc catgattacc gaacttacct ttgcggtact gaaatacgcg     1980
ttcctcattc tgttatggct g                                               2001
```

<210> SEQ ID NO 29
<211> LENGTH: 2001
<212> TYPE: DNA
<213> ORGANISM: Bifidobacterium animalis

<400> SEQUENCE: 29

```
gtcaatctat ctccgcggta atcaatgatc tatggacgaa tgcccggtat tttccaaaag       60
aaacggaggg cgttccaaaa cgcggcaccg ccggtatcca aagatggac gcgatgcggg      120
```

```
cgtgcgtgga gatttcggta agatgagatt tcagttttgg ggacaaaatc tccaacacat    180
agggattaca gacgccaccg cccgagcggg ccaacacggc gcgaccggcg cggcggcaga    240
caacatcaag catgggcatg ggctaggagg cccacgccga acacaaataa aaggagtgtg    300
ccacatggca gcacagatct ggtacgaaga cgacggcgat ctttcggttc tcgacggcaa    360
gaaggtcgca atcatcggtt acggctcgca gggccacgcg catgcgctca acctgcgtga    420
ctccggtgtc gacgtcgtcg tcggcctgcg tccgaactcg aagtccgtgg aattcgccaa    480
ggagcagggt ctggaagtca agagcgttcc ggaagccgct gccgaggccg acgtcatcat    540
gatcctggcc cctgaccagt accagaaggg aatctgggag aacgacatcg agccgaacat    600
caagccgggc gccgccctgg ccttcgcaca cggcttcaac atccactacg gctacatcaa    660
gccgagcgag gacccccgg tcttcatggt cgccccgaag ggcccaggcc acatcgtccg    720
ccgtgagtat gtcgcaggcc gtggcgtccc ggttgtgacc gcagtcgagc aggatccgcg    780
cggcgacggt ggggatctcg cactggctta cgcgaaggcc ctcggtgcac tgcgcgccgg    840
cgccatcaag accacgttca aggaagagac cgaaaccgat ctgttcggcg agcagaacgt    900
gctgctcggc ggcgtgaaca agctcgtcga aatgggcttc gaggtactca ccgacgccgg    960
ctaccagccg gagatcgcct acttcgaggt gtgccacgag ctcaagatga tcgtcgacct   1020
catgaacgaa ggcggcctga acaaggatcg ctggagctgc tccgacaccg ctcagtacgg   1080
cgactacgtc agcaccgtca tcgacgagca tacccgtgag cgcatgcagt accacctgca   1140
gcgcattcag gacggctcct tcgccaagga gttcatggac gaccaggctg ccggcgcccc   1200
gaagttcaag cagctgcagg aggagtactc caacgtccgc atcgaagagg tcggcccgaa   1260
gctgcgcgcc atgttctcct ggaacaacga cgccgcgaag gacgccgacg aagccaactc   1320
cttcaccggc aagatcgccc gcgcccaggt tcagtgagcc gcgtgcggtg cgtccgcgca   1380
tgaagccgtg agcttcgcat ctgtcaaggt ggggcatgca taggcatgcc ccacctttg    1440
cgttctcctg cattgagcgg ccttctgcac tgagcgttct cccgccgtgg cgcagtttgc   1500
ggaagtttcc gtgaaccgcg ccgcaaagca actcgcgcgc ggtagttttc gcggatgctt   1560
ccgtttgttt gaccgcaaat gagggcaaaa gtggtaattc tttcggatga ttccgtaagc   1620
tgtgccgcgg aggtgtctgc aaacggcatg gttttcggat ggttccgtgt gtttggccgc   1680
cgatagacgc agtgacggca tatctttcgg acgcgtccgt gtgctatgcc ggggcgcggg   1740
ctgtacgtag cagatttcgc ggatgcttcc gtaagctgtg ccgcggagcg gtctgcaaac   1800
ggcatatcgt acggaagact ccgtgaaata gaccgcgtat gcccgcatgc atggtggatt   1860
acccggaagt ttccgagaaa cgagccgcag tcatagctgc ggctgcccga gacgcgcgcc   1920
ggtgaccgca gtgatctcgg caaccacggc agccgcggca taaccggga gcataggcgg   1980
caatgaccgg gctacttggc g                                             2001
```

<210> SEQ ID NO 30  
<211> LENGTH: 1001  
<212> TYPE: DNA  
<213> ORGANISM: Bifidobacterium animalis

<400> SEQUENCE: 30

```
aggaatcagg ttatagaact ggaatacgaa gccgatgtcg ttgcgccggt acgtcactag     60
atcatggtga ttaaggtcgg tgatgtcgcg gccgcccacg atcacgcgtc ccgaggtggc    120
ggtatccatg ccgccgagaa tattcagcgc agtcgtcttg ccggcgccgg actggccaag    180
gatcacgctg agctcgcctt cgtcggcggc gaagctcgca ccgtcgagcg cgcggatgga    240
```

-continued

```
ggaggaaccg gcagggtact ccttgaccac atcattgaac tcgatgtatg ccatggccac      300
ctccatctat acaaattgca cgtcatcgca cagcatacat atatagatta tgcgaaaacc      360
aatctggagt acagtggccg ccccgcgtg ctgcccgcca atgcggtgca acatacggaa       420
gcatccgtgg gatgtgccac taaccacccc gccaacggca cagctttcgg aagcatccga      480
gaaacgtgcc acaaaggaat ctaaaatggc acagcctacg gaagcatccg cacaacggac      540
cgcaaaccac ccctgcagcg gcacagcata cggacgcatc cgagagatgg gccagaaacc      600
accccatcag aggcacatct cacggaagca tccgagaacc aaaccgcagg ccgtcttccc      660
cgcagcacag cgtacggaag catccgagaa acgtactgcc agaaggctcc aaaatggcat      720
gcctctcgga ggtatccgag aaacgcgcca cggaatggtc tgaaaacagc atagctttcg      780
gaagcatccg caaaaccgac cgcgaagaag tctgaaaacg gcatgccata cggaagcatc      840
cgcaaaaccg accacacagc ggccgacggc aacgcctact gcgcgtgga gtcgagcacg       900 gtcttcgcgt cgcgcttcgc cgaggcgcgc gaggtgatcg catacgcggc gaacaacacg      960
gcgagccaga tcacaccggc gatgagcgca atgcggtagc t                        1001
```

<210> SEQ ID NO 31
<211> LENGTH: 2001
<212> TYPE: DNA
<213> ORGANISM: Bifidobacterium animalis

<400> SEQUENCE: 31

```
cgctgttctg cgcgctgctt cccgaacgtc gctagcgtac tgcgttatgg gaatggcatg       60
gcgttcggag gcttccgtgg aaaccgccaa tctgtaatct ggaaatggca gtttacgcgg      120
aaatgtctgc gcaaactgcc gttcaatgcg cgcgtgctcg gcgtgaacaa gaaacgcacg      180
ggcgacacgg tgcgcgatac tggaactatg ttagtttccg cagatttcaa caccatcccc      240
gaacagtatg ccaagaacgc gcccgatgac gcgcgcgtgg acggcgtgcc ctgcgtctcg      300
ttcccgttct acatcgacca tctcaacccg gccgccaagt atttgcactg ggaattcagc      360
gacccggatt ccattccggt atgcggattc gaatggatcc actggaccat ggcgaatctg      420
ccggtcgccg cgctcatgtt cgacccgtcc gacgcgcacg ccttgcagat tccgccggat      480
ttctcgcgcc gcgtcaccgc gatgatcccg gaggccgtgc agggccgcaa ttcgcaggcg      540
tcgccgctgt acgggcagga tcagcggaat ctgcagctcg tcgcacacta caccggcccg      600
cagccaccgg acaaggacca cggttatgta ctgcagatct ggggcaccac ctcgccgatc      660 gccgactcg aacagggctt ctggctcaac gagatgctgc acggcctcga gcattcgcag       720
gtcgtcgacg gcggcggcat cacgctgatc ggcaagtgct gagctctgcc tcgcagtccg      780
tttttcggaa gcatccgtgc gttatgccgc agtgaggtcc ctctgcggtc tgttttgcgg      840
agttttccgt atgctgtgcc gcggtgggtc agtttcttgg tcgttctttc ggaagcttcc      900
gtgtaacggt acgcgggagt ggcattccgc ggttcgtttt tcggatgctt ccgtatgact      960
gaccgcagat tagctgattg gcggtccgcc ttacggatgc ttccgtatgc caggccatgg     1020
gggagtcaat ctgtggcgta tctttcggaa ccttccgtgt aatcgaccgc agaagtgctg     1080
cctggcggca tgtcttgcgg aagcatccgc gcgattgacc gcgagggggg cgatttgcgg     1140
cccagctttc ggaaccttcc gcgtaacaga ccgcggggag ggcaatctgc ggcatatttc     1200
acggaagctt ccgtaaaacg ggccgcagat atgtcgtgca gtggttcgtt tcacggagtc     1260
ttccgtataa caggccgtga atggggcgat ctgcaaacca cataggcgcc cgcatattcg     1320
```

-continued

| | |
|---|---|
| cccacatatc cacctacgga ataattggcc gcccagcact gccggtgcgc ggcaaagcgc | 1380 |
| ggtagaacac taaaggagcg aagagaaacc aattcgtgaa atcgaggaag caaaatggca | 1440 |
| tgcactacaa ttctggtggg ccgcggcgcg agttatgacg ggtcgacgat catcgcgcgc | 1500 |
| aatgaagacg acgagcccgg ctcgttcaac aacaagaagc tcatcatcgt gcggcctgaa | 1560 |
| gaccagccgc gcacctacac aagcgtgaac ggtcacctga cgatcgagct gcccgacgat | 1620 |
| ccgctgcagt attccgagac cccgaattcg ttcacgagcg acggcgtgtg gggcgaggcc | 1680 |
| ggtatcaacg aggcgaacgt ggcgatgacg gccaccgaga cgatcacgtc gaacgcgcgc | 1740 |
| gcgctcggcg cagacccgct cgtgccgtac acgccggcga tcggcaagcc cggcgacgcg | 1800 |
| aattacgtgc ccgcagtggc cggcggcatt ggcgaggagg atctcgtcac aatcgtgctg | 1860 |
| ccgtacattc acaccgctcg cgagggcgtg gagcgcttgg gctcgctgct cgaggaatat | 1920 |
| ggcacgtacg aaagcaacgg cattggcttc tccgattcgc atgaggtgtg gtggatcgag | 1980 |
| acggtgggcg gtcatcattg g | 2001 |

```
<210> SEQ ID NO 32
<211> LENGTH: 25
<212> TYPE: DNA
<213> ORGANISM: Bifidobacterium animalis

<400> SEQUENCE: 32
gcggtcacat gcacgggaat cttcg                                         25

<210> SEQ ID NO 33
<211> LENGTH: 25
<212> TYPE: DNA
<213> ORGANISM: Bifidobacterium animalis

<400> SEQUENCE: 33
gcggcatact ttacggaagt ctccg                                         25

<210> SEQ ID NO 34
<211> LENGTH: 25
<212> TYPE: DNA
<213> ORGANISM: Bifidobacterium animalis

<400> SEQUENCE: 34
gcggtcggtc atgcggaagc atccg                                         25

<210> SEQ ID NO 35
<211> LENGTH: 25
<212> TYPE: DNA
<213> ORGANISM: Bifidobacterium animalis

<400> SEQUENCE: 35
atgatgtatc ttacggaacg ctccg                                         25

<210> SEQ ID NO 36
<211> LENGTH: 25
<212> TYPE: DNA
<213> ORGANISM: Bifidobacterium animalis

<400> SEQUENCE: 36
gcggtccgtc tcaaggaaac ttccg                                         25

<210> SEQ ID NO 37
<211> LENGTH: 25
<212> TYPE: DNA
<213> ORGANISM: Bifidobacterium animalis
```

```
<400> SEQUENCE: 37
gcggcgcatc ttacggaagc ttccg                                              25

<210> SEQ ID NO 38
<211> LENGTH: 25
<212> TYPE: DNA
<213> ORGANISM: Bifidobacterium animalis

<400> SEQUENCE: 38
gcggcatatc tcacggaaga ctccg                                              25

<210> SEQ ID NO 39
<211> LENGTH: 25
<212> TYPE: DNA
<213> ORGANISM: Bifidobacterium animalis

<400> SEQUENCE: 39
gcggatcagt ttgcggaaga ctccg                                              25

<210> SEQ ID NO 40
<211> LENGTH: 25
<212> TYPE: DNA
<213> ORGANISM: Bifidobacterium animalis

<400> SEQUENCE: 40
gcggtcggtc atgcggaagg ttccg                                              25

<210> SEQ ID NO 41
<211> LENGTH: 25
<212> TYPE: DNA
<213> ORGANISM: Bifidobacterium animalis

<400> SEQUENCE: 41
gtggcacgtc gtacggaagg ttccg                                              25

<210> SEQ ID NO 42
<211> LENGTH: 25
<212> TYPE: DNA
<213> ORGANISM: Bifidobacterium animalis

<400> SEQUENCE: 42
atggcatatc ttacggaagc ttccg                                              25

<210> SEQ ID NO 43
<211> LENGTH: 26
<212> TYPE: DNA
<213> ORGANISM: Bifidobacterium animalis

<400> SEQUENCE: 43
caaaatcgac catatacggc gtttgc                                             26

<210> SEQ ID NO 44
<211> LENGTH: 27
<212> TYPE: DNA
<213> ORGANISM: Bifidobacterium animalis

<400> SEQUENCE: 44
caaggaatgc catgctggag cctcttt                                            27

<210> SEQ ID NO 45
<211> LENGTH: 27
<212> TYPE: DNA
```

<210> SEQ ID NO 45
<211> LENGTH: 27
<212> TYPE: DNA
<213> ORGANISM: Bifidobacterium animalis

<400> SEQUENCE: 45
taaaccatgc cgcggcggag tctgcaa                                      27

<210> SEQ ID NO 46
<211> LENGTH: 27
<212> TYPE: DNA
<213> ORGANISM: Bifidobacterium animalis

<400> SEQUENCE: 46
agaaccatgc cagcaaaaga cgttttt                                      27

<210> SEQ ID NO 47
<211> LENGTH: 27
<212> TYPE: DNA
<213> ORGANISM: Bifidobacterium animalis

<400> SEQUENCE: 47
aaaaccatgc cacaaagaag cgctatt                                      27

<210> SEQ ID NO 48
<211> LENGTH: 27
<212> TYPE: DNA
<213> ORGANISM: Bifidobacterium animalis

<400> SEQUENCE: 48
aaaaacacgg cgcaaacggg tacccct                                      27

<210> SEQ ID NO 49
<211> LENGTH: 27
<212> TYPE: DNA
<213> ORGANISM: Bifidobacterium animalis

<400> SEQUENCE: 49
cacaatgaac cgcgaagaga acaatct                                      27

<210> SEQ ID NO 50
<211> LENGTH: 27
<212> TYPE: DNA
<213> ORGANISM: Bifidobacterium animalis

<400> SEQUENCE: 50
agaaacaaac cgttttgaga ccaccgc                                      27

<210> SEQ ID NO 51
<211> LENGTH: 27
<212> TYPE: DNA
<213> ORGANISM: Bifidobacterium animalis

<400> SEQUENCE: 51
agtaatgggg cgccacagcg gcaatct                                      27

<210> SEQ ID NO 52
<211> LENGTH: 27
<212> TYPE: DNA
<213> ORGANISM: Bifidobacterium animalis

<400> SEQUENCE: 52
agaaacacac caaggaggaa tccagaa                                      27

<210> SEQ ID NO 53
<211> LENGTH: 25

<212> TYPE: DNA
<213> ORGANISM: Bifidobacterium animalis

<400> SEQUENCE: 53
gcggcatggt atgcggaaga ttctg          25

<210> SEQ ID NO 54
<211> LENGTH: 25
<212> TYPE: DNA
<213> ORGANISM: Bifidobacterium animalis

<400> SEQUENCE: 54
gcggtcgatc atgcggaaga ctccg          25

<210> SEQ ID NO 55
<211> LENGTH: 25
<212> TYPE: DNA
<213> ORGANISM: Bifidobacterium animalis

<400> SEQUENCE: 55
gcggcacgtc ttacgggaag ttccg          25

<210> SEQ ID NO 56
<211> LENGTH: 25
<212> TYPE: DNA
<213> ORGANISM: Bifidobacterium animalis

<400> SEQUENCE: 56
actgcacttc ctaagggcgc ctcca          25

<210> SEQ ID NO 57
<211> LENGTH: 25
<212> TYPE: DNA
<213> ORGANISM: Bifidobacterium animalis

<400> SEQUENCE: 57
gcggcatggc ttacggaagg ttccg          25

<210> SEQ ID NO 58
<211> LENGTH: 25
<212> TYPE: DNA
<213> ORGANISM: Bifidobacterium animalis

<400> SEQUENCE: 58
gcggtcagtc ttacggaagg ttccg          25

<210> SEQ ID NO 59
<211> LENGTH: 25
<212> TYPE: DNA
<213> ORGANISM: Bifidobacterium animalis

<400> SEQUENCE: 59
gcggtcgaat atacggacga ctccg          25

<210> SEQ ID NO 60
<211> LENGTH: 25
<212> TYPE: DNA
<213> ORGANISM: Bifidobacterium animalis

<400> SEQUENCE: 60
gcggtacagc ttacggaaga ctccg          25

<210> SEQ ID NO 61

```
<211> LENGTH: 27
<212> TYPE: DNA
<213> ORGANISM: Bifidobacterium animalis

<400> SEQUENCE: 61
agaaccgtgc cgcaaacgta gactttt                                              27

<210> SEQ ID NO 62
<211> LENGTH: 27
<212> TYPE: DNA
<213> ORGANISM: Bifidobacterium animalis

<400> SEQUENCE: 62
taaaccgtgc ctcaaaaggc atcccgc                                              27

<210> SEQ ID NO 63
<211> LENGTH: 27
<212> TYPE: DNA
<213> ORGANISM: Bifidobacterium animalis

<400> SEQUENCE: 63
agaaaccggc catcggacag tctggaa                                              27

<210> SEQ ID NO 64
<211> LENGTH: 26
<212> TYPE: DNA
<213> ORGANISM: Bifidobacterium animalis

<400> SEQUENCE: 64
tgaaactggc tgcgaaagga gcttat                                               26

<210> SEQ ID NO 65
<211> LENGTH: 27
<212> TYPE: DNA
<213> ORGANISM: Bifidobacterium animalis

<400> SEQUENCE: 65
agagtcgtac cgcaaatgga gacttcc                                              27

<210> SEQ ID NO 66
<211> LENGTH: 27
<212> TYPE: DNA
<213> ORGANISM: Bifidobacterium animalis

<400> SEQUENCE: 66
tgaaagcgac tatattcagg tcacttt                                              27

<210> SEQ ID NO 67
<211> LENGTH: 27
<212> TYPE: DNA
<213> ORGANISM: Bifidobacterium animalis

<400> SEQUENCE: 67
aaaaacagac cacgaaacgg ggtctgt                                              27

<210> SEQ ID NO 68
<211> LENGTH: 25
<212> TYPE: DNA
<213> ORGANISM: Bifidobacterium animalis

<400> SEQUENCE: 68
gaggcacgtt tcacggaaac atccg                                                25
```

```
<210> SEQ ID NO 69
<211> LENGTH: 25
<212> TYPE: DNA
<213> ORGANISM: Bifidobacterium animalis

<400> SEQUENCE: 69
gtggctcgtc tttcggaagc ttccg                                         25

<210> SEQ ID NO 70
<211> LENGTH: 25
<212> TYPE: DNA
<213> ORGANISM: Bifidobacterium animalis

<400> SEQUENCE: 70
gcagcacatt ccacggaatc ttccg                                         25

<210> SEQ ID NO 71
<211> LENGTH: 25
<212> TYPE: DNA
<213> ORGANISM: Bifidobacterium animalis

<400> SEQUENCE: 71
gcggcacagc tcacggaaac atccg                                         25

<210> SEQ ID NO 72
<211> LENGTH: 25
<212> TYPE: DNA
<213> ORGANISM: Bifidobacterium animalis

<400> SEQUENCE: 72
acggcacaac gtacggaagc ttccg                                         25

<210> SEQ ID NO 73
<211> LENGTH: 25
<212> TYPE: DNA
<213> ORGANISM: Bifidobacterium animalis

<400> SEQUENCE: 73
gcggcacagc tcacggacgc ttccg                                         25

<210> SEQ ID NO 74
<211> LENGTH: 25
<212> TYPE: DNA
<213> ORGANISM: Bifidobacterium animalis

<400> SEQUENCE: 74
acggcacagc tcacggaaac atccg                                         25

<210> SEQ ID NO 75
<211> LENGTH: 25
<212> TYPE: DNA
<213> ORGANISM: Bifidobacterium animalis

<400> SEQUENCE: 75
gcgacctgat tcatggaagc atccg                                         25

<210> SEQ ID NO 76
<211> LENGTH: 27
<212> TYPE: DNA
<213> ORGANISM: Bifidobacterium animalis

<400> SEQUENCE: 76
cataaccgac caccaagtca cgcagat                                       27
```

<210> SEQ ID NO 77
<211> LENGTH: 27
<212> TYPE: DNA
<213> ORGANISM: Bifidobacterium animalis

<400> SEQUENCE: 77
aacgatatgt cgtctgcaga cttcccc                                        27

<210> SEQ ID NO 78
<211> LENGTH: 27
<212> TYPE: DNA
<213> ORGANISM: Bifidobacterium animalis

<400> SEQUENCE: 78
taagatatgc cattcacaga ccattct                                        27

<210> SEQ ID NO 79
<211> LENGTH: 27
<212> TYPE: DNA
<213> ORGANISM: Bifidobacterium animalis

<400> SEQUENCE: 79
aagggacgac cgcgcagacc ccgttcc                                        27

<210> SEQ ID NO 80
<211> LENGTH: 27
<212> TYPE: DNA
<213> ORGANISM: Bifidobacterium animalis

<400> SEQUENCE: 80
taagatacgt cattctcaga ccactct                                        27

<210> SEQ ID NO 81
<211> LENGTH: 26
<212> TYPE: DNA
<213> ORGANISM: Bifidobacterium animalis

<400> SEQUENCE: 81
caaaaccggc cgccaaagcg atatct                                         26

<210> SEQ ID NO 82
<211> LENGTH: 27
<212> TYPE: DNA
<213> ORGANISM: Bifidobacterium animalis

<400> SEQUENCE: 82
caatctatgc cgcaaaatgc gcacatc                                        27

<210> SEQ ID NO 83
<211> LENGTH: 25
<212> TYPE: DNA
<213> ORGANISM: Bifidobacterium animalis

<400> SEQUENCE: 83
ctatcctgct tcacggaacc ttccg                                          25

<210> SEQ ID NO 84
<211> LENGTH: 25
<212> TYPE: DNA
<213> ORGANISM: Bifidobacterium animalis

<400> SEQUENCE: 84
gcggcacctc ccacggaacc ttccg                                          25

<210> SEQ ID NO 85
<211> LENGTH: 25
<212> TYPE: DNA
<213> ORGANISM: Bifidobacterium animalis

<400> SEQUENCE: 85
gcggcacagc tcacggaagc tcccg                                    25

<210> SEQ ID NO 86
<211> LENGTH: 25
<212> TYPE: DNA
<213> ORGANISM: Bifidobacterium animalis

<400> SEQUENCE: 86
gcggcacagt ttccggaacc atccg                                    25

<210> SEQ ID NO 87
<211> LENGTH: 25
<212> TYPE: DNA
<213> ORGANISM: Bifidobacterium animalis

<400> SEQUENCE: 87
gcggcacatt gcacggaaac atccg                                    25

<210> SEQ ID NO 88
<211> LENGTH: 25
<212> TYPE: DNA
<213> ORGANISM: Bifidobacterium animalis

<400> SEQUENCE: 88
acggcacagc ttgcggaaac atccg                                    25

<210> SEQ ID NO 89
<211> LENGTH: 25
<212> TYPE: DNA
<213> ORGANISM: Bifidobacterium animalis

<400> SEQUENCE: 89
acggcatggt tcacggaaac atccg                                    25

<210> SEQ ID NO 90
<211> LENGTH: 25
<212> TYPE: DNA
<213> ORGANISM: Bifidobacterium animalis

<400> SEQUENCE: 90
acggcacagc atacggaacc atccg                                    25

<210> SEQ ID NO 91
<211> LENGTH: 25
<212> TYPE: DNA
<213> ORGANISM: Bifidobacterium animalis

<400> SEQUENCE: 91
gcagaccact ccacggaacc ttccg                                    25

<210> SEQ ID NO 92
<211> LENGTH: 25
<212> TYPE: DNA
<213> ORGANISM: Bifidobacterium animalis

<400> SEQUENCE: 92

```
gcggcaccgc tcacggaagc atccg                                          25

<210> SEQ ID NO 93
<211> LENGTH: 27
<212> TYPE: DNA
<213> ORGANISM: Bifidobacterium animalis

<400> SEQUENCE: 93
taaaacaggt cgcagactcc ccttccc                                        27

<210> SEQ ID NO 94
<211> LENGTH: 27
<212> TYPE: DNA
<213> ORGANISM: Bifidobacterium animalis

<400> SEQUENCE: 94
caataccgac cactggcgac tctcccg                                        27

<210> SEQ ID NO 95
<211> LENGTH: 27
<212> TYPE: DNA
<213> ORGANISM: Bifidobacterium animalis

<400> SEQUENCE: 95
taaatctgac cactggaagc cccatcg                                        27

<210> SEQ ID NO 96
<211> LENGTH: 27
<212> TYPE: DNA
<213> ORGANISM: Bifidobacterium animalis

<400> SEQUENCE: 96
aaaatcagac cacagatgac cttcccc                                        27

<210> SEQ ID NO 97
<211> LENGTH: 27
<212> TYPE: DNA
<213> ORGANISM: Bifidobacterium animalis

<400> SEQUENCE: 97
aaagactgac cacggcgaca ctgattt                                        27

<210> SEQ ID NO 98
<211> LENGTH: 27
<212> TYPE: DNA
<213> ORGANISM: Bifidobacterium animalis

<400> SEQUENCE: 98
cagattcggc cacaacggca cccattt                                        27

<210> SEQ ID NO 99
<211> LENGTH: 27
<212> TYPE: DNA
<213> ORGANISM: Bifidobacterium animalis

<400> SEQUENCE: 99
aaaaccatgc cacggcagcg ctgattt                                        27

<210> SEQ ID NO 100
<211> LENGTH: 27
<212> TYPE: DNA
<213> ORGANISM: Bifidobacterium animalis

<400> SEQUENCE: 100
```
taagatctgc cgcctaagga cacatct                                          27

<210> SEQ ID NO 101
<211> LENGTH: 27
<212> TYPE: DNA
<213> ORGANISM: Bifidobacterium animalis

<400> SEQUENCE: 101
aaaaccagac catctccaag gctctcc                                          27

<210> SEQ ID NO 102
<211> LENGTH: 26
<212> TYPE: DNA
<213> ORGANISM: Bifidobacterium animalis

<400> SEQUENCE: 102
gtggcgcagt ttgcggaagt ttccgt                                           26

<210> SEQ ID NO 103
<211> LENGTH: 26
<212> TYPE: DNA
<213> ORGANISM: Bifidobacterium animalis

<400> SEQUENCE: 103
gcggtagttt tcgcggatgc ttccgt                                           26

<210> SEQ ID NO 104
<211> LENGTH: 26
<212> TYPE: DNA
<213> ORGANISM: Bifidobacterium animalis

<400> SEQUENCE: 104
gtggtaattc tttcggatga ttccgt                                           26

<210> SEQ ID NO 105
<211> LENGTH: 26
<212> TYPE: DNA
<213> ORGANISM: Bifidobacterium animalis

<400> SEQUENCE: 105
acggcatggt tttcggatgg ttccgt                                           26

<210> SEQ ID NO 106
<211> LENGTH: 26
<212> TYPE: DNA
<213> ORGANISM: Bifidobacterium animalis

<400> SEQUENCE: 106
acggcatatc tttcggacgc gtccgt                                           26

<210> SEQ ID NO 107
<211> LENGTH: 26
<212> TYPE: DNA
<213> ORGANISM: Bifidobacterium animalis

<400> SEQUENCE: 107
gtagcagatt tcgcggatgc ttccgt                                           26

<210> SEQ ID NO 108
<211> LENGTH: 26
<212> TYPE: DNA
<213> ORGANISM: Bifidobacterium animalis

<400> SEQUENCE: 108
acggcatatc gtacggaaga ctccgt                                              26

<210> SEQ ID NO 109
<211> LENGTH: 26
<212> TYPE: DNA
<213> ORGANISM: Bifidobacterium animalis

<400> SEQUENCE: 109
atggtggatt acccggaagt ttccga                                              26

<210> SEQ ID NO 110
<211> LENGTH: 26
<212> TYPE: DNA
<213> ORGANISM: Bifidobacterium animalis

<400> SEQUENCE: 110
gaaccgcgcc gcaaagcaac tcgcgc                                              26

<210> SEQ ID NO 111
<211> LENGTH: 26
<212> TYPE: DNA
<213> ORGANISM: Bifidobacterium animalis

<400> SEQUENCE: 111
ttgtttgacc gcaaatgagg gcaaaa                                              26

<210> SEQ ID NO 112
<211> LENGTH: 26
<212> TYPE: DNA
<213> ORGANISM: Bifidobacterium animalis

<400> SEQUENCE: 112
aagctgtgcc gcggaggtgt ctgcaa                                              26

<210> SEQ ID NO 113
<211> LENGTH: 26
<212> TYPE: DNA
<213> ORGANISM: Bifidobacterium animalis

<400> SEQUENCE: 113
gtgtttggcc gccgatagac gcagtg                                              26

<210> SEQ ID NO 114
<211> LENGTH: 26
<212> TYPE: DNA
<213> ORGANISM: Bifidobacterium animalis

<400> SEQUENCE: 114
gtgctatgcc ggggcgcggg ctgtac                                              26

<210> SEQ ID NO 115
<211> LENGTH: 26
<212> TYPE: DNA
<213> ORGANISM: Bifidobacterium animalis

<400> SEQUENCE: 115
aagctgtgcc gcggagcggt ctgcaa                                              26

<210> SEQ ID NO 116
<211> LENGTH: 26
<212> TYPE: DNA
<213> ORGANISM: Bifidobacterium animalis

```
<400> SEQUENCE: 116
gaaatagacc gcgtatgccc gcatgc                                          26

<210> SEQ ID NO 117
<211> LENGTH: 25
<212> TYPE: DNA
<213> ORGANISM: Bifidobacterium animalis

<400> SEQUENCE: 117
gcggtgcaac atacggaagc atccg                                           25

<210> SEQ ID NO 118
<211> LENGTH: 25
<212> TYPE: DNA
<213> ORGANISM: Bifidobacterium animalis

<400> SEQUENCE: 118
acggcacagc tttcggaagc atccg                                           25

<210> SEQ ID NO 119
<211> LENGTH: 25
<212> TYPE: DNA
<213> ORGANISM: Bifidobacterium animalis

<400> SEQUENCE: 119
atggcacagc ctacggaagc atccg                                           25

<210> SEQ ID NO 120
<211> LENGTH: 25
<212> TYPE: DNA
<213> ORGANISM: Bifidobacterium animalis

<400> SEQUENCE: 120
gcggcacagc atacggacgc atccg                                           25

<210> SEQ ID NO 121
<211> LENGTH: 25
<212> TYPE: DNA
<213> ORGANISM: Bifidobacterium animalis

<400> SEQUENCE: 121
gaggcacatc tcacggaagc atccg                                           25

<210> SEQ ID NO 122
<211> LENGTH: 25
<212> TYPE: DNA
<213> ORGANISM: Bifidobacterium animalis

<400> SEQUENCE: 122
gcagcacagc gtacggaagc atccg                                           25

<210> SEQ ID NO 123
<211> LENGTH: 25
<212> TYPE: DNA
<213> ORGANISM: Bifidobacterium animalis

<400> SEQUENCE: 123
atggcatgcc tctcggaggt atccg                                           25

<210> SEQ ID NO 124
<211> LENGTH: 25
<212> TYPE: DNA
```

```
<213> ORGANISM: Bifidobacterium animalis

<400> SEQUENCE: 124
acagcatagc tttcggaagc atccg                                          25

<210> SEQ ID NO 125
<211> LENGTH: 25
<212> TYPE: DNA
<213> ORGANISM: Bifidobacterium animalis

<400> SEQUENCE: 125
acggcatgcc atacggaagc atccg                                          25

<210> SEQ ID NO 126
<211> LENGTH: 27
<212> TYPE: DNA
<213> ORGANISM: Bifidobacterium animalis

<400> SEQUENCE: 126
tgggatgtgc cactaaccac cccgcca                                        27

<210> SEQ ID NO 127
<211> LENGTH: 26
<212> TYPE: DNA
<213> ORGANISM: Bifidobacterium animalis

<400> SEQUENCE: 127
agaaacgtgc cacaaaggaa tctaaa                                         26

<210> SEQ ID NO 128
<211> LENGTH: 27
<212> TYPE: DNA
<213> ORGANISM: Bifidobacterium animalis

<400> SEQUENCE: 128
cacaacggac cgcaaaccac ccctgca                                        27

<210> SEQ ID NO 129
<211> LENGTH: 27
<212> TYPE: DNA
<213> ORGANISM: Bifidobacterium animalis

<400> SEQUENCE: 129
agagatgggc cagaaaccac cccatca                                        27

<210> SEQ ID NO 130
<211> LENGTH: 27
<212> TYPE: DNA
<213> ORGANISM: Bifidobacterium animalis

<400> SEQUENCE: 130
agaaccaaac cgcaggccgt cttcccc                                        27

<210> SEQ ID NO 131
<211> LENGTH: 27
<212> TYPE: DNA
<213> ORGANISM: Bifidobacterium animalis

<400> SEQUENCE: 131
agaaacgtac tgccagaagg ctccaaa                                        27

<210> SEQ ID NO 132
<211> LENGTH: 27
```

<212> TYPE: DNA
<213> ORGANISM: Bifidobacterium animalis

<400> SEQUENCE: 132
agaaacgcgc cacggaatgg tctgaaa                                              27

<210> SEQ ID NO 133
<211> LENGTH: 27
<212> TYPE: DNA
<213> ORGANISM: Bifidobacterium animalis

<400> SEQUENCE: 133
caaaaccgac cgcgaagaag tctgaaa                                              27

<210> SEQ ID NO 134
<211> LENGTH: 25
<212> TYPE: DNA
<213> ORGANISM: Bifidobacterium animalis

<400> SEQUENCE: 134
gcagtccgtt tttcggaagc atccg                                                25

<210> SEQ ID NO 135
<211> LENGTH: 25
<212> TYPE: DNA
<213> ORGANISM: Bifidobacterium animalis

<400> SEQUENCE: 135
gcggtctgtt ttgcggagtt ttccg                                                25

<210> SEQ ID NO 136
<211> LENGTH: 25
<212> TYPE: DNA
<213> ORGANISM: Bifidobacterium animalis

<400> SEQUENCE: 136
ttggtcgttc tttcggaagc ttccg                                                25

<210> SEQ ID NO 137
<211> LENGTH: 25
<212> TYPE: DNA
<213> ORGANISM: Bifidobacterium animalis

<400> SEQUENCE: 137
gcggttcgtt tttcggatgc ttccg                                                25

<210> SEQ ID NO 138
<211> LENGTH: 25
<212> TYPE: DNA
<213> ORGANISM: Bifidobacterium animalis

<400> SEQUENCE: 138
gcggtccgcc ttacggatgc ttccg                                                25

<210> SEQ ID NO 139
<211> LENGTH: 25
<212> TYPE: DNA
<213> ORGANISM: Bifidobacterium animalis

<400> SEQUENCE: 139
gtggcgtatc tttcggaacc ttccg                                                25

<210> SEQ ID NO 140

```
<211> LENGTH: 25
<212> TYPE: DNA
<213> ORGANISM: Bifidobacterium animalis

<400> SEQUENCE: 140
gcggcatgtc ttgcggaagc atccg                                          25

<210> SEQ ID NO 141
<211> LENGTH: 25
<212> TYPE: DNA
<213> ORGANISM: Bifidobacterium animalis

<400> SEQUENCE: 141
gcggcccagc tttcggaacc ttccg                                          25

<210> SEQ ID NO 142
<211> LENGTH: 25
<212> TYPE: DNA
<213> ORGANISM: Bifidobacterium animalis

<400> SEQUENCE: 142
gcggcatatt tcacggaagc ttccg                                          25

<210> SEQ ID NO 143
<211> LENGTH: 25
<212> TYPE: DNA
<213> ORGANISM: Bifidobacterium animalis

<400> SEQUENCE: 143
gtggttcgtt tcacggagtc ttccg                                          25

<210> SEQ ID NO 144
<211> LENGTH: 27
<212> TYPE: DNA
<213> ORGANISM: Bifidobacterium animalis

<400> SEQUENCE: 144
tgcgttatgc cgcagtgagg tccctct                                        27

<210> SEQ ID NO 145
<211> LENGTH: 27
<212> TYPE: DNA
<213> ORGANISM: Bifidobacterium animalis

<400> SEQUENCE: 145
tatgctgtgc cgcggtgggt cagtttc                                        27

<210> SEQ ID NO 146
<211> LENGTH: 27
<212> TYPE: DNA
<213> ORGANISM: Bifidobacterium animalis

<400> SEQUENCE: 146
tgtaacggta cgcgggagtg gcattcc                                        27

<210> SEQ ID NO 147
<211> LENGTH: 27
<212> TYPE: DNA
<213> ORGANISM: Bifidobacterium animalis

<400> SEQUENCE: 147
tatgactgac cgcagattag ctgattg                                        27
```

```
<210> SEQ ID NO 148
<211> LENGTH: 27
<212> TYPE: DNA
<213> ORGANISM: Bifidobacterium animalis

<400> SEQUENCE: 148
tatgccaggc catggggag tcaatct                                          27

<210> SEQ ID NO 149
<211> LENGTH: 27
<212> TYPE: DNA
<213> ORGANISM: Bifidobacterium animalis

<400> SEQUENCE: 149
tgtaatcgac cgcagaagtg ctgcctg                                         27

<210> SEQ ID NO 150
<211> LENGTH: 27
<212> TYPE: DNA
<213> ORGANISM: Bifidobacterium animalis

<400> SEQUENCE: 150
cgcgattgac cgcggagggg gcgattt                                         27

<210> SEQ ID NO 151
<211> LENGTH: 27
<212> TYPE: DNA
<213> ORGANISM: Bifidobacterium animalis

<400> SEQUENCE: 151
cgtaacagac cgcggggagg gcaatct                                         27

<210> SEQ ID NO 152
<211> LENGTH: 27
<212> TYPE: DNA
<213> ORGANISM: Bifidobacterium animalis

<400> SEQUENCE: 152
taaaacgggc cgcagatatg tcgtgca                                         27

<210> SEQ ID NO 153
<211> LENGTH: 24
<212> TYPE: DNA
<213> ORGANISM: Artificial
<220> FEATURE:
<223> OTHER INFORMATION: synthetic primer

<400> SEQUENCE: 153
tgagggaagc cgaactcaat caca                                            24

<210> SEQ ID NO 154
<211> LENGTH: 24
<212> TYPE: DNA
<213> ORGANISM: Artificial
<220> FEATURE:
<223> OTHER INFORMATION: synthetic primer

<400> SEQUENCE: 154
ttggatgcaa gccctcaatg aagc                                            24

<210> SEQ ID NO 155
<211> LENGTH: 543
<212> TYPE: PRT
<213> ORGANISM: Bifidobacterium animalis
```

<400> SEQUENCE: 155

```
Met Lys Tyr Ala Glu Asn Asn Ala Met Lys Arg Gly Glu Gly Leu Glu
1               5                   10                  15

Asp Thr Leu Pro Ile Ser Leu Ile Cys Asp Phe Ile Phe Cys Pro Arg
            20                  25                  30

Arg Ala Trp Leu Glu Ile Gln Gly Glu Lys Ile Glu Ser Leu Gln Met
        35                  40                  45

Glu Arg Gly Phe His Asp His Arg Ala Val Asp Ala Asn Gly Gly
    50                  55                  60

Arg Gly Asp Thr Asp Tyr Arg Ala Val Asn Val Asn His Gln Gly Trp
65                  70                  75                  80

Gly Leu Ser Gly Arg Leu Asp Ala Val Arg Leu Asn Glu Asp Asn Gly
                85                  90                  95

Val Ile Ile Arg Glu Tyr Lys Ala Thr Pro Val Arg Arg Ser Met Asp
                100                 105                 110

Val Thr His Ala Met Arg Ile Gln Leu Ala Leu Gln Ala Ala Cys Met
            115                 120                 125

Glu Asp Met Gly Tyr Arg Val Asp Gly Thr Glu Ile Phe Phe Thr Ser
130                 135                 140

His His Arg Ile Val Pro Val Glu Leu Arg Lys Ser Asp Tyr Glu Glu
145                 150                 155                 160

Ala Tyr Gly Ser Val Gln Glu Val Arg Lys Leu Ile Glu Cys Glu Thr
                165                 170                 175

Ala Pro Leu Pro Phe Glu Asp Asp Pro Arg Cys Met Arg Cys Ser His
            180                 185                 190

Ala Gly Ile Cys Leu Pro Glu Glu Arg Ala His Asn Ile Pro Glu His
        195                 200                 205

Arg Ile Met Val Lys Val Pro Asp His Ala Val Thr His Leu Ala Thr
210                 215                 220

Pro Gly Ala Arg Ala Tyr Leu Lys Ser Gly Arg Met His Val Ser Lys
225                 230                 235                 240

Asn Gly Asp Glu Ile Thr Ser Val Pro Leu Asp Ser Ile Gln Ala Leu
                245                 250                 255

Gln Ile His Gly Asn Val Asp Val Ser Ser Gly Leu Met Arg Glu Leu
            260                 265                 270

Met Trp Arg Asn Ile Pro Ile Leu Trp Cys Ser Gly Thr Gly Arg Leu
        275                 280                 285

Met Gly Trp Ser Val Ser Ser Tyr Gly Pro Asn Gly Glu Thr Arg Val
    290                 295                 300

Ala Gln His Val Ala Ser His Glu Gly Arg Leu Asp Leu Ala Arg Glu
305                 310                 315                 320

Phe Ile Ser Ala Lys Ile His Asn Gln Ile Val Leu Leu Arg Arg Ser
                325                 330                 335

Asp Lys Asn Asn Asn Val Leu Phe Asp Met Lys His Ile Glu Lys Ser
            340                 345                 350

Val Val Asn Ala Asn Arg Ile Gln Asp Ile Leu Ser Leu Glu Gly Gln
        355                 360                 365

Ala Ala Ala Leu Tyr Phe Ser Gln Phe His His Leu Ile Ser Val Asn
    370                 375                 380

Lys Arg Asn Glu Trp Pro Trp Leu Glu Arg Met Arg His Pro Ala Pro
385                 390                 395                 400

Asp Pro Leu Asn Ala Leu Leu Asp Tyr Thr Tyr Ser Leu Leu Leu Ser
                405                 410                 415
```

```
Asp Cys Ile Arg Ala Ile Val Ser Cys Gly Leu Asp Ala His Ala Gly
            420                 425                 430

Phe Leu His Ser Ser Lys Arg Asn Lys Pro Ala Leu Ala Leu Asp Leu
            435                 440                 445

Met Glu Glu Phe Arg Ala Pro Ile Ala Asp Ser Val Val Gln Thr Val
450                 455                 460

Val Asn Asn Gly Glu Ile Lys Arg Asn Gly Phe Ala Asn Val Met Gly
465                 470                 475                 480

Ser Val Arg Leu Arg Asp Glu Thr Arg Lys Thr Leu Ile Gly Ala Tyr
                485                 490                 495

Glu Arg Arg Met Ala Thr Glu Leu Lys His Pro Val Tyr Ala Tyr Arg
            500                 505                 510

Ala Ser Trp Arg Arg Ile Val Glu Ile Gln Ala Arg Met Val Leu Gly
            515                 520                 525

Arg Leu Glu Gly Ser Leu Glu Arg Tyr Arg Gly Ile Arg Val Arg
            530                 535                 540

<210> SEQ ID NO 156
<211> LENGTH: 97
<212> TYPE: PRT
<213> ORGANISM: Bifidobacterium animalis

<400> SEQUENCE: 156

Met Asn Asn Leu Met Gln Arg Tyr Ile Ile Ala Tyr Asp Ile Lys Asp
1               5                   10                  15

Asp Ser Arg Arg Ile Arg Val Ser Lys Leu Leu Gln Ser Tyr Gly Asn
            20                  25                  30

Arg Leu Gln Tyr Ser Val Phe Leu Met Glu Met Arg Glu Val Arg Leu
        35                  40                  45

Val Arg Met Glu Glu Arg Leu His Thr Leu Ile Asn Gly Ala Glu Asp
50                  55                  60

Ser Val Val Ile Ala Arg Leu Asp Asp Ala Lys Thr Ser Glu Ser Ile
65                  70                  75                  80

Val Phe Ile Gly Ser Arg Asn Tyr Glu Asp Val Arg Val Pro Thr Val
                85                  90                  95

Ile

<210> SEQ ID NO 157
<211> LENGTH: 397
<212> TYPE: PRT
<213> ORGANISM: Bifidobacterium animalis

<400> SEQUENCE: 157

Met Arg Lys Leu Thr Val Gln Asp Leu Asn Glu Ala Ala Lys Ile Gly
1               5                   10                  15

Gly Ser Asn Ala Leu Thr Glu Val Thr Ser Leu Ala Pro Ala Ala Gly
            20                  25                  30

Met Gly Ser Ile Val Ala Pro Ala Lys Tyr Thr Ala Gly Asn Gly Ser
        35                  40                  45

Thr Tyr Val Tyr Glu Lys Arg Trp Val Asn Asp Glu Cys Val Asp Thr
    50                  55                  60

Val Leu Ile Asp Ser Arg Thr Ser Gln Ala Asn Arg Leu Glu Asp Tyr
65                  70                  75                  80

Ile Ser Arg Ala Ile Glu Val Gly His Pro Ile Phe Ser Lys Met Pro
                85                  90                  95
```

```
Gln Val Arg Val Arg Tyr Glu Met Ile Pro Gly Asp Glu Ser Ser Val
             100                 105                 110

Arg Tyr Phe Asp Asp Val Gln Leu Pro His Arg Ala Val Asp Ala His
             115                 120                 125

Ile Arg Ile Ala Glu Phe Ser Glu Ser Asp Lys Val Lys Tyr Met Ala
         130                 135                 140

Ala Arg Asn Ser Ser Leu Glu Asp Leu Ser Ala Met Leu Ala Ile Ser
145                 150                 155                 160

Pro Val Thr Val Met Phe Gly Cys Trp Asp Ser Thr Arg Asn Lys Asn
                 165                 170                 175

Gln Leu Arg Ile Pro Ala Ser Phe Asn Gly Glu Ile Tyr Ala Val Leu
             180                 185                 190

Ala Asp Gln Thr His Glu Ser Pro Ile His Arg Ala Gly Ala Arg Ile
             195                 200                 205

Asp Pro Val Ala Ala Gly Val His Leu Thr Lys Asn Glu Ala Lys Lys
             210                 215                 220

Ile Ala Glu Arg Ile Lys Gly Thr Met Asn Asp Lys Lys Leu Ser Lys
225                 230                 235                 240

Phe Ala Ser Ser Gly Asp Gly Ser Thr Ile Val Ile Gly Ala Ile Pro
                 245                 250                 255

Pro Ser Thr Asp Ala Asn Ala Leu Asp Gly Ile Ala Val Arg Ser Ile
             260                 265                 270

Thr Arg Thr His Val Leu Ser Phe Ser Met Leu Arg Ala Met Arg Phe
             275                 280                 285

Gly Lys Gly Pro Glu Gly Asp Glu Ala Ile Arg Val Leu Leu Ala Ala
             290                 295                 300

Ala Leu Ile Asn Ala Met Val Gly Ser Asn Ala Glu Leu His Leu Arg
305                 310                 315                 320

Glu Asn Cys Phe Leu Val Gly Ala Asp Glu Pro Lys Thr Val Leu Asp
                 325                 330                 335

Arg Arg Gly Gly Lys His Asp Asp Leu Glu Met Leu Thr Leu Glu Asp
             340                 345                 350

Ala Asp Glu Leu Leu Ala Gln Ala Tyr Ala Gln Ala Gln Lys Lys Ala
             355                 360                 365

Gly Ile Asp Trp His Gly Gln Ile Ile Thr Val Gln Gly Asp Pro Ala
             370                 375                 380

Val Ile Glu Ser Ala Ser Ala Ala Asp Asp Asp Arg
385                 390                 395

<210> SEQ ID NO 158
<211> LENGTH: 545
<212> TYPE: PRT
<213> ORGANISM: Bifidobacterium animalis

<400> SEQUENCE: 158

Met Thr Phe Ala Ile Arg Ile His Phe Leu Leu Ala Ser Tyr Gln Gly
1               5                   10                  15

Ala Ser Glu Tyr Gly Glu Lys Glu Ser Phe Pro Thr Pro Met Arg Leu
             20                  25                  30

Tyr Gln Ala Met Val Ser Ala Ala His Thr Val Phe Ser Ser Glu Asn
         35                  40                  45

Ser Gln Gly Met Leu Asp Lys Arg Leu Asn Ala Ala Leu Glu Trp Leu
     50                  55                  60

Glu Ser Asn Pro Pro Glu Ala Ile Arg Phe Pro Glu Ile Val Ser Gln
65                  70                  75                  80
```

```
Ser Pro Thr Ser His Asn Ala Ile Ala Tyr Arg Arg Lys Ala Asp Lys
                 85                  90                  95

Ala Pro Lys Ala Glu Arg Ala Arg Ser Ala Val Met Tyr Arg Thr Asp
            100                 105                 110

Glu Gln Gly Asp Met Ile Leu Glu Trp Lys Asn Gly Pro Asp Asp Glu
        115                 120                 125

Glu Cys Ser Thr Ile Ala Asp Leu Cys Trp Glu Ile Pro Phe Leu Gly
    130                 135                 140

Gly Ala Gly Ser Pro Val Arg Ile Thr Val Glu Gly Phe Asp Phe
145                 150                 155                 160

Pro Leu Pro Asp Ser Tyr Met Leu Arg Pro Glu Ser Gln Ser Leu Met
                165                 170                 175

Glu Val Glu Arg Ala Arg Glu Leu Pro Cys Pro Ala Pro Gly Leu His
            180                 185                 190

Gln Glu Leu Met Glu His Tyr Thr Gln Ala Asn Pro His Pro Ala Ser
        195                 200                 205

Lys Ile Pro Lys Asp Ser Ser Thr Lys Lys Asp Thr Glu Val Arg Ser
210                 215                 220

Glu Lys Arg Leu Gln Cys Val His Arg Ser Thr Tyr Ser Pro Gln Lys
225                 230                 235                 240

Gln Ala Lys Ser Ala Val Gln Leu Pro Trp Thr Arg Met Ile Ile Ile
            245                 250                 255

Pro Ala Arg Val Glu Ser Asn Ala Ser Ala Trp Asn Pro Arg Asp Asp
                260                 265                 270

Glu Leu Thr Ala Trp Cys Val Ala Leu His Arg Leu Leu Val Arg Arg
            275                 280                 285

Trp Gly Thr Asp Val Ser Pro Tyr Leu Thr Gly Arg Trp Ser Thr Asp
    290                 295                 300

Ser Met Val Lys Arg Pro Ala Asn Asn Ile Ala Ile Gln Val Leu Arg
305                 310                 315                 320

Lys Asp Tyr Ala Ser Leu Ile Ala Asp Gln Arg Ile Ala Glu Ser Leu
                325                 330                 335

Pro Ala Phe Ile Leu Met Ile Pro Ser Glu Met Asp Ala Gly Glu Leu
            340                 345                 350

Arg Lys Leu Gly Thr Leu Val Arg Ser Leu Ala Asn Ser Arg Ile Tyr
        355                 360                 365

Tyr Ser His Ser Lys Pro Ala Leu Arg Leu Gly Asn Pro Ile Pro Gly
    370                 375                 380

Glu Gly Val His Leu Trp Ser Lys Pro Arg Asp Gly Met His Arg Ile
385                 390                 395                 400

Trp Ser Pro Met Pro Phe Ser Val Asn Glu Thr Gln Ala Glu Lys Ser
                405                 410                 415

Pro Ala Gly Gln Ser Arg Ser Trp Thr Ala Glu Cys Asn Leu Ala Val
            420                 425                 430

Ser Ile Gly His Val Phe Arg Asn Val Phe Arg Gly Gln Ile Ala Glu
        435                 440                 445

Lys Arg Gly Arg Gly Lys Tyr Trp Asp Leu Ile Asp Ala Val Thr Ala
450                 455                 460

Gly Asp Ser Phe Val Arg Ile Leu Ala Ala Arg Thr Val Ala Arg Pro
465                 470                 475                 480

Asp Met Gly Asp Tyr Val His Arg Met Arg Glu Gly Phe Met Ile Thr
                485                 490                 495
```

```
Ala Ser Thr Gly Leu Ile Ala Phe Glu Asn Val Ile Lys Asp Glu Ile
            500                 505                 510

Leu Ala Ile Gly Gln Ser Arg His Phe Gly Gly Gly Leu Leu Ile Pro
            515                 520                 525

Met Asp Cys Pro Glu Ser Cys Phe Thr Thr Lys Gly Gln Pro Lys Trp
            530                 535                 540

Arg
545

<210> SEQ ID NO 159
<211> LENGTH: 1017
<212> TYPE: PRT
<213> ORGANISM: Bifidobacterium animalis

<400> SEQUENCE: 159

Met Glu Met Asn Ala Thr Thr Pro Asn Glu Met Leu Val Glu Leu Tyr
1               5                   10                  15

Asp Leu Phe Val Glu Ser Leu His Gln Gly Arg Lys Pro Tyr Leu Trp
            20                  25                  30

Gln Thr Arg Leu Met Arg Glu Val Val Asn Asn Gly Gln Trp Met Lys
        35                  40                  45

Leu Ile Ser Ala Pro Thr Gly Ser Gly Lys Thr Ala Val Ile Asp Val
50                  55                  60

His Leu Phe Val Asn Ala Leu Ala Gly Leu Ala Ala Leu Asp Asp Ile
65                  70                  75                  80

Pro Leu Pro Lys Glu Leu Asn His Leu Leu Lys Ser Leu Ser Leu Asp
                85                  90                  95

Ala Val Pro Arg Arg Met Ala Val Thr Val Asn Arg Arg Gly Ile Val
            100                 105                 110

Asp Asp Gln Tyr Leu Glu Ala Ser Ala Ala Cys Ala Arg Ile Asn Asp
            115                 120                 125

Val Ala Ser Leu Asp Asp Thr Glu Ser Glu Ile Leu Lys Leu Ile
            130                 135                 140

Ala Val Gly Leu Tyr Ala Arg Gln Tyr Ser Glu Leu Met Asp Arg Gln
145                 150                 155                 160

Trp Thr Phe Asp Gln Leu Ala Phe Gln Cys Gln Glu Gln Gly Lys Val
                165                 170                 175

Val Cys Ser Ala Gln Arg Leu Arg Gly Gly Leu Asp Asp Lys Ala Asp
            180                 185                 190

Met Arg Val Trp Arg Tyr Lys Pro Leu Glu Cys Gln Ile Leu Cys Gly
            195                 200                 205

Thr Pro Asp Met Ile Gly Ser Arg Leu Leu Phe Ser Gly Tyr Gly Val
            210                 215                 220

Ser Asp Ala Ala Lys Pro Ile Glu Ala Ala Leu Ala Tyr Asp Ala
225                 230                 235                 240

Val Ile Val Val Asp Glu Ala Gln Leu Ser Arg Gln Phe Ala Tyr Thr
                245                 250                 255

Ala Gln Gln Ile Pro Arg Ile Glu Ala Cys Ile Arg Gln Gly Glu Pro
            260                 265                 270

Leu Pro Val Ser Pro Leu Gln Val Val Thr Thr Ala Thr Pro Ser
            275                 280                 285

Gly Glu Asn Ile Ser Asn Leu Gln Asp Glu Gly Ser Ile Cys Gly Val
        290                 295                 300

Glu Glu Ala Asp Phe Lys Ile Asp Leu Glu Leu Arg Arg Arg Leu Arg
305                 310                 315                 320
```

```
Thr Pro Arg Pro Ile Gln Val Leu Ser Val Asp Asp Lys Gln Ile Ala
            325                 330                 335
Thr Cys Met Ala Lys Glu Ser Ile Ala Leu Gln Glu Arg Leu Gly Gly
            340                 345                 350
Val Val Val Cys Phe Val Asn Thr Val Pro Arg Ala Ser Glu Val Val
            355                 360                 365
Arg Arg Leu Arg Glu Ala Leu Gly Lys Asp Ala Gly Asp Asn Ala Val
    370                 375                 380
Arg Ala Phe Val Gly Pro Met Arg Asp Tyr Glu Arg Asp Gln Phe Val
385                 390                 395                 400
Gln Arg Leu Asp Ser Thr Glu Pro Leu Tyr Asp Ala Ile Arg Gly Asp
                405                 410                 415
Gln Ser Ala Ile Thr Gln Thr Gly Leu Lys Phe Val Ala Thr Gln
                420                 425                 430
Thr Leu Glu Ala Gly Ile Asp Ala Asp Phe Ser Gly Met Ile Ser Glu
            435                 440                 445
Leu Ala Pro Ala Ala Ser Leu Val Gln Arg Ala Gly Arg Val Asn Arg
    450                 455                 460
Arg Gly Leu Arg Pro Glu Gly Pro Val Val Ile Cys Cys Gln Asn Ser
465                 470                 475                 480
Gly Lys Ile Arg Gly Pro Tyr Met Lys Glu Asp Leu Thr Ala Ala Gln
                485                 490                 495
Met Trp Leu Glu Ser Leu Pro Val Glu Gly Leu Thr Ala Trp Ser Ser
            500                 505                 510
Val Leu Gln Pro Pro Ala Pro Ala Gln Leu Glu Arg Met Val Leu Gln
    515                 520                 525
Arg Leu Glu Trp Trp Asp Val Glu Asn Leu Ser His Thr Ser Glu Asp
530                 535                 540
Val Phe Ala Glu His Arg Ala Ala Gly Arg Pro Tyr Pro Ala Asp Val
545                 550                 555                 560
Asp Leu Trp Leu Arg Asp Asp Leu Ala Asp Arg Val Thr Pro Asp Val
                565                 570                 575
Ala Val Val Ile Arg Thr Leu Pro Gln Asp Asp Tyr Leu Ala Gln Arg
                580                 585                 590
Leu Leu Ala Thr Thr Pro Pro Asp Ser Arg Glu Leu Phe Pro Val Thr
            595                 600                 605
Ser Tyr Ala Met Leu Asp Ala Leu Gln Asn Lys Leu Lys Gly Arg Arg
    610                 615                 620
Ala Phe Ile Met Arg Thr Asn Ser Ser Glu Asn Gly Asn Ala Val His
625                 630                 635                 640
Leu Leu Asp Gly Gln Ala Asp Ser Asp Pro Thr Leu Arg Ser Gly Asp
                645                 650                 655
Val Leu Ile Val Asp Asp Gly Ala Arg Val Phe Ser Glu Gly Ile Pro
                660                 665                 670
Met Leu Asp Pro Phe Ser Lys Asp Lys His Ser Lys Leu Gln
            675                 680                 685
Asp Glu Ile Thr Ser Pro Gly Asp Val Phe Asn Lys Cys Gln Gln Ser
            690                 695                 700
Met Ala Val Leu His Ala Asn Arg Glu Lys Gln Pro Ala Leu Tyr Glu
705                 710                 715                 720
Glu Leu Ser Glu Val Leu Arg Ala Glu Thr Asp Thr Asp Glu Thr Val
                725                 730                 735
```

Glu Ala Glu Tyr Gln Gly Ile Asp Val Ser Lys Tyr Pro Asn Leu Gln
                740                 745                 750

Glu Ala Leu Asn Ser Cys Ala Ile Asn Asn His Gly Phe Arg Ile Ala
                755                 760                 765

Phe Val Asp Gly Phe Ile Asp Gly Asp Ser Ser Asp Ser Ser Val Phe
            770                 775                 780

Ile Val Leu Gln Ser Ser Asp Ala Ala Asp Gly Asp Gln Leu Gln Glu
785                 790                 795                 800

Ile Gly Arg Phe Asn Arg Gln Gly Pro Val Leu Leu Asp Gly Pro Gly
                805                 810                 815

Ser His Gln Glu Ser Val Gly Ser Arg Ala Glu Leu Phe Ala Ala Lys
                820                 825                 830

Leu Gly Phe Asp Ser Arg Leu Val Ala Asp Ile Arg Thr Ala Gly Leu
            835                 840                 845

His His Asp Asp Gly Lys Lys Asp Pro Arg Phe Gln Thr Leu Leu Arg
        850                 855                 860

Tyr Arg Met Pro Asn Val Pro Ala Glu Pro Leu Ala Lys Ser Met Tyr
865                 870                 875                 880

Arg Ser Ser Ser Trp Glu Arg Ala Lys Arg Ile Glu Leu Arg Leu Asp
                885                 890                 895

Gly Trp Arg His Glu Gln Arg Ser Ala Ala Glu Cys Trp Ala Leu Asp
            900                 905                 910

Ser Glu Ser Leu Gln Ala His Asp Lys Glu Leu Val Thr Arg Leu Ala
        915                 920                 925

Gly Thr Ser His Gly His Gly Arg Ser Met Phe Pro Met Asn Ala Gln
    930                 935                 940

Gln Val Ile Pro Asp Ala Ile Ile Gln Thr Val Ser Glu Glu Asn Gly
945                 950                 955                 960

Asp Gly Ser Gln Thr Ile His Ala Ile Arg Ser Ala Ala Glu Glu Leu
                965                 970                 975

Phe Asp Ala Gly Tyr Trp Gln Ser Ile Met Glu Arg Thr Asn Glu Arg
            980                 985                 990

Tyr Gly Leu Trp Gly Ile Ala Phe Leu Glu Thr Leu Leu Arg Ala Ala
        995                 1000                1005

Asp Val Thr Ile Ser Met Glu Gly Arg
    1010                1015

<210> SEQ ID NO 160
<211> LENGTH: 348
<212> TYPE: PRT
<213> ORGANISM: Bifidobacterium animalis

<400> SEQUENCE: 160

Met Ser Val Leu Arg Ile Pro Ala Asp Tyr Asp Asp Ala Phe Ser His
1               5                   10                  15

Met Leu Gly Phe Gly Leu Ala Ser Ile Leu Glu Asp Ala Val Glu Asp
            20                  25                  30

Arg Ile Cys Arg Leu Trp Trp Ser Gly Arg His Thr Leu Met Val Glu
        35                  40                  45

Thr Asn Asp Glu Ile Thr Glu Met Glu Cys Ala His Ile Val Arg Ala
    50                  55                  60

His Ala Glu Arg Trp His Lys Ser Gln Trp Leu Asn Ala Arg Gly Ser
65                  70                  75                  80

Tyr Ala Gly Lys Gly Lys Thr Val Ala Thr Leu Ser Pro Arg Ile Gly
                85                  90                  95

```
Thr Val Ala Gly Arg Glu Glu Trp Val Ala Leu Glu Arg Asp Arg Arg
                100                 105                 110

Asp Ala Ile Asp Ser Leu Arg Thr Leu Asp Glu Arg Tyr Ile Gly
            115                 120                 125

Ala Leu Gly Glu Pro Ser Tyr Trp Ser Leu Asn Arg Thr Lys Ala Thr
        130                 135                 140

Pro Glu Ile Gln Gln Lys Phe Gly Ala Ser Leu Trp Glu Met Thr Pro
145                 150                 155                 160

Arg Asn Arg Gly Asn Glu Phe Val Thr Met Arg Leu Leu Lys Leu Ala
                165                 170                 175

Ser Ile Ile Thr Ala Arg Thr Ala Glu Lys Val His Ser Gly Leu Phe
            180                 185                 190

Gly Leu Thr Asn Val Asp Glu Leu Ala Gly Thr Glu Asp Ser His Thr
        195                 200                 205

Pro Thr Gly Leu Lys Val Pro Ser Arg Thr Asp Asn Ala Arg Ala Trp
210                 215                 220

Cys Ala Leu Phe Gly Phe Ser Asn Cys Pro Val Tyr Arg Ser Val His
225                 230                 235                 240

Tyr Glu Thr Ser Pro Thr Ala Gly Phe Ile Arg His Asp Ser Gly Gly
                245                 250                 255

Gly Pro Ser Trp His Val Val Leu Pro Leu Thr Glu Lys Ser Trp Thr
            260                 265                 270

Leu Ala Lys Tyr Arg Ser Val Ile Arg Ser Tyr Ala Leu Asp Tyr Val
        275                 280                 285

Gly Glu Asn Ala Leu His Leu Asp Gln Asp Ser Leu Ser Asp Ser Thr
290                 295                 300

Val Ala Leu Tyr Ala Glu Leu Cys Arg Trp Leu Arg Asp Gln Gly Leu
305                 310                 315                 320

Arg Tyr Cys Met Leu Phe Gln Arg His Gly Thr Gln Ala Lys Ser Pro
                325                 330                 335

Glu Tyr Trp Leu Leu Arg Gly Gln Leu Ile Arg Leu
            340                 345

<210> SEQ ID NO 161
<211> LENGTH: 36
<212> TYPE: DNA
<213> ORGANISM: Bifidobacterium animalis

<400> SEQUENCE: 161
atctccgaag tctcggcttc ggagcttcat tgagga                              36

<210> SEQ ID NO 162
<211> LENGTH: 36
<212> TYPE: DNA
<213> ORGANISM: Bifidobacterium animalis

<400> SEQUENCE: 162
atctccgaag ttttggcttc ggagcttcat tgagga                              36
```